(12) United States Patent
Lingam et al.

(10) Patent No.: US 8,487,121 B2
(45) Date of Patent: Jul. 16, 2013

(54) CHROMANE DERIVATIVES AS TRPV3 MODULATORS

(75) Inventors: V S Prasadarao Lingam, Koparkhairane (IN); Abraham Thomas, Sanpada (IN); Laxmikant Atmaram Gharat, Majiwada (IN); Deepak Vitthal Ukirde, Pune District (IN); Shantaram Kashinath Phatangare, Kharghar (IN); Ajit Shankar Mindhe, Pune District (IN); Neelima Khairatkar-Joshi, Pachpakhadi (IN); Vidya Ganapati Kattige, Thane (IN)

(73) Assignee: Glenmark Pharmaceuticals S.A., La Chaux-de-Fonds (CH)

( * ) Notice: Subject to any disclaimer, the term of this patent is extended or adjusted under 35 U.S.C. 154(b) by 431 days.

(21) Appl. No.: 12/808,937

(22) PCT Filed: Dec. 16, 2008

(86) PCT No.: PCT/IN2008/000838
§ 371 (c)(1),
(2), (4) Date: Jun. 17, 2010

(87) PCT Pub. No.: WO2009/084034
PCT Pub. Date: Jul. 9, 2009

(65) Prior Publication Data
US 2010/0311778 A1    Dec. 9, 2010

Related U.S. Application Data

(60) Provisional application No. 61/019,995, filed on Jan. 9, 2008, provisional application No. 61/043,931, filed on Apr. 10, 2008.

(30) Foreign Application Priority Data

Dec. 18, 2007 (IN) .......................... 2481/MUM/2007
Mar. 26, 2008 (IN) ........................... 647/MUM/2008

(51) Int. Cl.
*C07D 311/56* (2006.01)
*C07D 305/00* (2006.01)
*A61K 31/34* (2006.01)

(52) U.S. Cl.
USPC ........................... 549/331; 549/332; 514/462

(58) Field of Classification Search
USPC ................... 549/331, 332; 514/462
See application file for complete search history.

(56) References Cited

U.S. PATENT DOCUMENTS

| 4,537,962 | A | 8/1985 | Doria et al. |
| 5,418,245 | A | 5/1995 | Spada et al. |
| 6,610,749 | B2 | 8/2003 | Liao et al. |
| 6,734,208 | B2 | 5/2004 | Grainger et al. |
| 6,797,819 | B1 | 9/2004 | Shair et al. |
| 7,576,094 | B2 | 8/2009 | Chu et al. |
| 7,842,703 | B2 | 11/2010 | Gharat et al. |
| 7,872,009 | B2 * | 1/2011 | Albrecht et al. ......... 514/252.01 |
| 8,227,511 | B2 * | 7/2012 | Schmeck et al. .............. 514/456 |
| 2004/0009537 | A1 | 1/2004 | Roos et al. |
| 2005/0239899 | A1 | 10/2005 | Fecke et al. |
| 2007/0179164 | A1 | 8/2007 | Chong et al. |
| 2007/0219187 | A1 | 9/2007 | Bessis et al. |
| 2008/0096892 | A1 | 4/2008 | Cheng et al. |
| 2008/0131367 | A1 | 6/2008 | Mori et al. |
| 2010/0101733 | A1 | 4/2010 | Yu Chen et al. |

FOREIGN PATENT DOCUMENTS

| EP | 0339562 A1 | 11/1989 |
| JP | 07242666 | 9/1995 |
| WO | 0204444 A2 | 1/2002 |
| WO | 2007/042906 A1 | 4/2007 |

OTHER PUBLICATIONS

Andreani et al., Potential Antitumor Agents-Synthesis of imidazo[2,1-b]thiazole guanylhydrazones Bioorganic & Med. Chem., 2000, 8(9), 2359-2366.

Hu, H. Z. et al., Potentiation of TRPV3 Channel Function by Unsaturated Fatty Acids, J. of Cellular Phys., 2006, 208, 201-212.

Supplemental European Search Report dated Oct. 2, 2012 for corresponding International Patent Application No. PCT/IN2008/000838.

\* cited by examiner

*Primary Examiner* — Andrew D Kosar
*Assistant Examiner* — Raymond Covington
(74) *Attorney, Agent, or Firm* — Pergament Gilman & Cepeda LLP; Milagros A. Cepeda; Edward D. Pergament

(57) ABSTRACT

The present invention provides transient receptor potential vanilloid (TRPV) modulators. In particular, compounds described herein are useful for treating or preventing diseases, conditions and/or disorders modulated by TRPV3. Also provided herein are processes for preparing compounds described herein, intermediates used in their synthesis, pharmaceutical compositions thereof, and methods for treating or preventing diseases, conditions and/or disorders modulated by TRPV3.

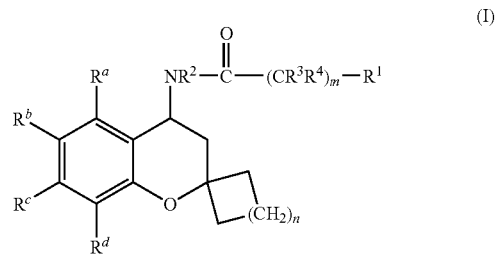

(I)

47 Claims, No Drawings

CHROMANE DERIVATIVES AS TRPV3 MODULATORS

This application claims the benefit of Indian Patent Application No. 2481/MUM/2007 filed on Dec. 18, 2007, and 647/MUM/2008 filed on Mar. 26, 2008, and U.S. Provisional Application No. 61/019,995, filed on Jan. 9, 2008, and 61/043,931, filed on Apr. 10, 2008 all of which are hereby incorporated by reference.

TECHNICAL FIELD

The present patent application relates to chromane derivatives with, Transient Receptor Potential Vanilloid 3 (TRPV3) activity.

BACKGROUND

Movement of ions across cellular membranes is carried out by specialized proteins. TRP channels are one large family of non-selective cation channels that function to help regulate ion flux and membrane potential. TRP channels are subdivided into 6 sub-families including the TRPV family. TRPV3 is a member of the TRPV class of TRP channels.

TRPV3 is a calcium permeable channel, specifically a calcium permeable nonselective cation channel. In addition to calcium ions, TRPV3 channels are permeable to other cations, for example sodium. Thus, TRPV3 channels modulate membrane potential by modulating the flux of cations such as calcium and sodium ions. TRPV3 receptors are mechanistically distinct from voltage-gated calcium channels. Generally, voltage-gated calcium channels respond to membrane depolarization and open to permit an influx of calcium from the extracellular medium that result in an increase in intracellular calcium levels or concentrations. In contrast, TRP channels which are non-selective cation channels are generally ligand gated (such as 2-aminoethoxydiphenyl borate [2-APB], heat, and vanilloids), long lasting, and produce more prolonged changes in ion concentration. These mechanistic differences are accompanied by structural differences among voltage-gated and TRP channels. Thus, although many diverse channels act to regulate ion flux and membrane potential in various cell types and in response to numerous stimuli, it is important to recognize the significant structural, functional, and mechanistic differences among different classes of ion channels.

TRPV3 proteins are thermosensitive channels expressed in skin cells (Peier et al. *Science* (2002), 296, 2046-2049) and dorsal root ganglion, trigeminal ganglion, spinal cord and brain (Xu et al. *Nature* (2002), 418, 181-185; Smith et al. *Nature* (2002), 418, 186-188). TRPV3 is also highly expressed in skin. In a keratinocyte cell line, stimulation of TRPV3 leads to release of inflammatory mediators including interleukin-1. Thus TRPV3 may also play an important role in regulating inflammation and pain that results from the release of inflammatory stimuli. Particular TRPV3 proteins that may be used in screening assays, as described herein, to identity compounds that modulate a function of TRPV3 include, but are not limited to human TRPV3, mouse TRPV3, rat TRPV3 and Drosophila TRPV3. US 2004/0009537 (the '537 application) disclosed sequences corresponding to human, mouse, and Drosophila TRPV3. For example, SEQ ID Nos 106 and 107 of the '537 application correspond to the human nucleic acid and amino acid sequences, respectively. SEQ ID Nos 108 and 109 of the '537 application correspond to the mouse nucleic acid and amino acid sequences, respectively.

TRPV3 function has been basically implicated in the reception and transduction of pain. Accordingly, it would be desirable to identify and make compounds that can modulate one or more functions of TRPV3.

WO 2007/056124 and WO 2006/017995 discloses TRPV3 modulators, in particular antagonists, for treatment of various diseases mediated TRPV3.

WO 2006/065686 and WO 2007/042906 disclose benzopyran derivatives.

In efforts to discover better analgesics, there still exists a need for therapeutic treatment of diseases, conditions and/or disorders modulated by TRPV3.

SUMMARY

The present patent application is directed to chromane compounds with TRP channel modulating activity, particularly, TRPV3 modulating activity. The present patent application relates to compounds of the formula (I)

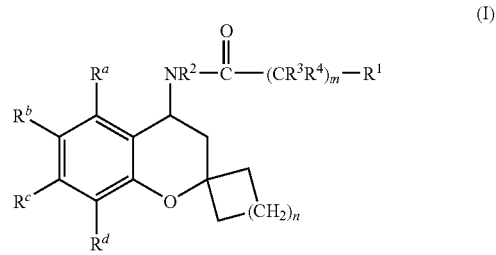

wherein, $R^1$ is selected from substituted or unsubstituted aryl, substituted or unsubstituted heteroaryl, substituted or unsubstituted heterocyclic group or substituted or unsubstituted cycloalkyl; in which aryl, heteroaryl and heterocyclic ring are mono, bi or tricyclic; and fully or partially aromatic;

wherein substituents on aryl, heteroaryl, heterocyclic ring and cycloalkyl are independently selected from the group consisting of halogen, hydroxy, nitro, cyano, substituted or unsubstituted amino, substituted or unsubstituted alkyl, linear or branched chain alkyl, linear or branched chain alkoxy, substituted or unsubstituted alkenyl, substituted or unsubstituted alkoxy, substituted or unsubstituted haloalkyl, fully or partially substituted haloalkyl, substituted or unsubstituted haloalkyloxy, fully or partially substituted haloalkyloxy, substituted or unsubstituted cycloalkyl, substituted or unsubstituted cycloalkoxy, substituted or unsubstituted cycloalkylalkyl, substituted or unsubstituted cycloalkylalkoxy, substituted or unsubstituted aryl, substituted or unsubstituted aryloxy, substituted or unsubstituted arylalkyl, substituted or unsubstituted arylalkoxy, substituted or unsubstituted heterocyclic group, substituted or unsubstituted heteroaryl, —S(O)$_p$R$^a$, —NHS(O)$_p$R$^a$, —O(CH$_2$)$_m$NR$^a$R$^b$, —C(O)—R$^a$ or —C(O)NR$^a$R$^b$;

$R^2$ is selected from the group consisting of hydrogen, substituted or unsubstituted alkyl, substituted or unsubstituted cycloalkyl, substituted or unsubstituted aryl, substituted or unsubstituted arylalkyl, substituted or unsubstituted heteroaryl, or substituted or unsubstituted heterocyclic group;

each occurrence of $R^a$, $R^b$, $R^c$ and $R^d$ are independently selected from hydrogen, nitro, cyano, halogen, —OR$^e$, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclic group;

$R^e$ is selected from the group consisting of hydrogen, substituted or unsubstituted alkyl, substituted or unsubstituted alkenyl, substituted or unsubstituted cycloalkyl, substituted or unsubstituted aryl, substituted or unsubstituted heteroaryl, or substituted or unsubstituted heterocyclic group;

$R^3$ and $R^4$ are independently selected from hydrogen, halogen, substituted or unsubstituted amino, substituted or unsubstituted alkyl, linear or branched chain alkyl, linear or branched chain alkoxy, substituted or unsubstituted alkenyl, substituted or unsubstituted alkoxy, substituted or unsubstituted haloalkyl, fully or partially substituted haloalkyl, substituted or unsubstituted haloalkyloxy, fully or partially substituted haloalkyloxy, substituted or unsubstituted cycloalkyl, substituted or unsubstituted cycloalkoxy, substituted or unsubstituted cycloalkylalkyl, substituted or unsubstituted cycloalkylalkoxy, substituted or unsubstituted aryl;

'm' is an integer selected from 1 to 4;
'n' is an integer selected from 0 to 3;
'p' is an integer selected from 0 to 2;
with proviso that $R^b$ is not a group selected from —$OR^e$, —$NR^aR^b$ or $C(O)NR^aR^b$.

It should be understood that the formula (I) structurally encompasses all stereoisomers, enantiomers and diastereomers and pharmaceutically acceptable salt that may be contemplated from the chemical structure of the genus described herein.

According to one embodiment of the invention, 'n' is an integer 1.

According to another embodiment of the invention, 'n' is an integer 2.

According to another embodiment of the invention, 'n' is an integer 3.

According to another embodiment of the invention, $R^1$ is substituted or unsubstituted monocyclic aryl, preferably phenyl. In this embodiment substituents one or more and are independently selected from halogen (for eg., F, Cl or Br), hydroxyl, alkyl (for eg., methyl), alkoxy (for eg., methoxy, ethoxy, n-propoxy, n-butoxy iso-propoxy), cycloalkyloxy (for eg., cyclopentyloxy), and 'm' is 1, 2 or 3, preferably 2.

According to another embodiment of the invention, $R^b$ is halogen (for eg., F, Cl or Br).

According to another embodiment of the invention, $R^a$, $R^c$ and $R^d$ are independently selected from hydrogen or hydroxy.

According to another embodiment of the invention, $R^3$ and $R^4$ are hydrogen.

Another preferred embodiment of the present invention is a compound of Formula (II),

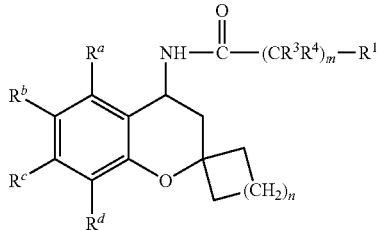

(II)

wherein, $R^1$ is selected from substituted or unsubstituted aryl, substituted or unsubstituted heteroaryl, substituted or unsubstituted heterocyclic group or substituted or unsubstituted cycloalkyl; in which aryl, heteroaryl and heterocyclic ring are mono, bi or tricyclic; and fully or partially aromatic;

wherein substituents on aryl, heteroaryl, heterocyclic ring and cycloalkyl are independently selected from the group consisting of halogen, hydroxyl, nitro, cyano, amino, substituted or unsubstituted alkyl, linear or branched chain alkyl, linear or branched chain alkoxy, substituted or unsubstituted alkenyl, substituted or unsubstituted alkoxy, substituted or unsubstituted haloalkyl, fully or partially substituted haloalkyl, substituted or unsubstituted haloalkyloxy, fully or partially substituted haloalkyloxy, substituted or unsubstituted cycloalkyl, substituted or unsubstituted cycloalkoxy, substituted or unsubstituted cycloalkylalkyl, substituted or unsubstituted cycloalkylalkoxy, substituted or unsubstituted aryl, substituted or unsubstituted aryloxy, substituted or unsubstituted arylalkyl, substituted or unsubstituted arylalkoxy, substituted or unsubstituted heterocyclic group, substituted or unsubstituted heteroaryl, —$S(O)_pR^a$, —$NHS(O)_pR^a$, —$O(CH_2)_mNR^aR^b$, —$C(O)$—$R^a$ or —$C(O)NR^aR^b$;

each occurrence of $R^a$, $R^b$, $R^c$ and $R^d$ are independently selected from hydrogen, nitro, cyano, halogen, —$OR^e$, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclic group;

$R^e$ is selected from the group consisting of hydrogen, substituted or unsubstituted alkyl, substituted or unsubstituted alkenyl, substituted or unsubstituted cycloalkyl, substituted or unsubstituted aryl, substituted or unsubstituted heteroaryl, or substituted or unsubstituted heterocyclic group;

$R^3$ and $R^4$ are independently selected from hydrogen, halogen, substituted or unsubstituted amino, substituted or unsubstituted alkyl, linear or branched chain alkyl, linear or branched chain alkoxy, substituted or unsubstituted alkenyl, substituted or unsubstituted alkoxy, substituted or unsubstituted haloalkyl, fully or partially substituted haloalkyl, substituted or unsubstituted haloalkyloxy, fully or partially substituted haloalkyloxy, substituted or unsubstituted cycloalkyl, substituted or unsubstituted cycloalkoxy, substituted or unsubstituted cycloalkylalkyl, substituted or unsubstituted cycloalkylalkoxy, substituted or unsubstituted aryl;

'm' is an integer selected from 1 to 4;
'n' is an integer selected from 0 to 3;
'p' is an integer selected from 0 to 2;
with proviso that $R^b$ is not a group selected from —$OR^e$, —$NR^aR^b$ or $C(O)NR^aR^b$.

It should be understood that the formula (II) structurally encompasses all stereoisomers, enantiomers, diastereomers and pharmaceutically acceptable salt that may be contemplated from the chemical structure of the genus described herein.

According to one embodiment of the invention, 'n' is an integer 1.

According to one embodiment of the invention, $R^1$ is substituted or unsubstituted aryl, wherein aryl is monocyclic, bicyclic or tricyclic ring system, preferably mono or bicyclic rings. In this embodiment 'm' is 1, 2 or 3.

According to another embodiment of the invention, $R^1$ is substituted or unsubstituted monocyclic aryl, preferably phenyl. In this embodiment one or more substituents are independently selected from halogen (for eg., F, Cl or Br), hydroxyl, alkyl (for eg., methyl), alkoxy (for eg., methoxy, ethoxy, n-propoxy, n-butoxy iso-propoxy), cycloalkyloxy (for eg., cyclopentyloxy), cycloalkylalkoxy (for eg., cyclopropylmethoxy), alkyl sulfonyl amino (for eg., —$NHS(O)_2$ CH₃, —NHS(O)₂CH(CH₃)₂), alkylaminoalkoxy (for eg., —OCH₂CH₂N(CH₃)₂), arylalkyloxy (for eg., benzyloxy) or heteroaryl (for eg., pyridine or pyrimidine); and 'm' is 1, 2 or 3.

According to another embodiment of the invention, R¹ is substituted or unsubstituted bicyclic aryl, preferably naphthyl. In this embodiment one or more substituents are independently selected from alkoxy (for eg., methoxy, ethoxy, or iso-propoxy) or fully or partially substituted haloalkoxy (OCHF₂); and 'm' is 1, 2 or 3.

According to another embodiment of the invention, R¹ is substituted or unsubstituted bicyclic aryl. In this embodiment aryl is partially aromatic ring, preferably tetrahydronaphthalene; and 'm' is 1, 2 or 3.

According to another embodiment of the invention, R¹ is substituted or unsubstituted heterocyclic group, wherein heterocyclic group is mono, bi or tricyclic system and fully or partially aromatic.

According to another embodiment of the invention, R¹ is substituted or unsubstituted heteroaryl, wherein heteroaryl is monocyclic, bicyclic or tricyclic ring system. In this embodiment 'm' is 1, 2 or 3.

According to another embodiment of the invention, R¹ is substituted or unsubstituted monocyclic heteroaryl, preferably pyridine. In this embodiment 'm' is 1, 2 or 3.

According to another embodiment of the invention, R¹ is substituted or unsubstituted bicyclic heteroaryl, preferably indole, benzodioxole, benzisoxazole, benzofuran, quinoline or benzodioxin. In this embodiment one or more substituent are independently selected from halogen (for eg., F, Cl or Br), alkyl (for eg., methyl) or alkoxy (for eg., methoxy, ethoxy, n-propoxy, n-butoxy iso-propoxy); and 'm' is 1, 2 or 3.

According to another embodiment of the invention, R¹ is substituted or unsubstituted tricyclic heteroaryl, preferably dibenzofuran. In this embodiment 'm' is 1, 2 or 3.

According to another embodiment of the invention, R$^b$ is selected from hydrogen or halogen (for eg., Fluorine, chlorine or bromine).

According to another embodiment of the invention, R$^a$, R$^c$ and R$^d$ are independently selected from hydrogen, halogen (for eg., Fluorine, chlorine or bromine), substituted or unsubstituted alkyl (for eg., methyl).

According to another embodiment of the invention, R$^a$, R$^c$ and R$^d$ are independently selected from hydrogen or —OR$^e$, wherein R$^e$ is hydrogen, substituted or unsubstituted alkyl (for eg., methyl) or substituted or unsubstituted aryl (for eg., phenyl) or substituted or unsubstituted arylalkyl (for eg., benzyl).

According to another embodiment of the invention, R³ and R⁴ are independently hydrogen, hydroxyl or alkyl (methyl). In this embodiment 'm' is 1, 2 or 3.

Below are the representative compounds, which are illustrative in nature only and are not intended to limit to the scope of the invention.

N-(8-Chloro-3,4-dihydrospiro[chromene-2,1'-cyclobutan]-4-yl)-2-phenylacetamide (Compound No. 1), N-(6-Chloro-3,4-dihydrospiro[chromene-2,1'-cyclobutan]-4-yl)-2-(2-methoxyphenyl)acetamide (Compound No. 2), N-(6-chloro-3,4-dihydrospiro[chromene-2,1'-cyclobutan]-4-yl)-2-{2-[(methylsulfonyl)amino]phenyl}acetamide (Compound No. 3), N-(6-Chloro-3,4-dihydrospiro[chromene-2,1'-cyclobutan]-4-yl)-2-(2-(cyclopentyloxy)-3-methoxyphenyl)acetamide (Compound No. 4), N-[(4R)-8-Chloro-3,4-dihydrospiro[chromene-2,1'-cyclobutan]-4-yl]-2-(2-cyclopentyloxy-3-methoxy)phenylacetamide (Compound No. 5), N-[(4R)-8-Chloro-3,4-dihydrospiro[chromene-2,1'-cyclobutan]-4-yl]-2-(2-cyclopentyloxy-3-methoxy)phenylacetamide (Compound No. 6), N-(6-Chloro-3,4-dihydrospiro[chromene-2,1'-cyclobutan]-4-yl)-2-(3,4-dimethoxyphenyl)acetamide (Compound No. 7), N-(6-Chloro-3,4-dihydrospiro[chromene-2,1'-cyclobutan]-4-yl)-2-pyridin-2-ylacetamide (Compound No. 8), N-(3,4-Dihydrospiro[chromene-2,1'-cyclobutan]-4-yl)-2-(1-naphthyl)acetamide (Compound No. 9), N-(6-Fluoro-(3,4-dihydrospiro[chromene-2,1'-cyclobutan]-4-yl)-2-(1-naphthyl)acetamide (Compound No. 10), N-[(4R)-6,8-Difluoro-3,4-dihydrospiro[chromene-2,1'-cyclobutan]-4-yl]-2-(1-naphthyl)acetamide (Compound No. 11), N-[(4R)-6-Chloro-3,4-dihydrospiro[chromene-2,1'-cyclobutan]-4-yl]-2-(1-naphthyl)acetamide (Compound No. 12), N-[(4R)-6-Chloro-3,4-dihydrospiro[chromene-2,1'-cyclobutan]-4-yl]-2-(1-naphthyl)acetamide (Compound No. 13), N-(7-Chloro-3,4-dihydrospiro[chromene-2,1'-cyclobutan]-4-yl)-2-(1-naphthyl)acetamide (Compound No. 14), N-[(4R)-8-Chloro-3,4-dihydrospiro[chromene-2,1'-cyclobutan]-4-yl]-2-(1-naphthyl)acetamide (Compound No. 15), N-[(4S)-8-Chloro-3,4-dihydrospiro[chromene-2,1'-cyclobutan]-4-yl]-2-(1-naphthyl)acetamide (Compound No. 16), N-(5-Hydroxy-3,4-dihydrospiro[chromene-2,1'-cyclobutan]-4-yl)-2-(1-naphthyl)acetamide (Compound No. 17), N-(6-Chloro-3,4-dihydrospiro[chromene-2,1'-cyclobutan]-4-yl)-2-(2-naphthyl)acetamide (Compound No. 18), (2S)—N-[(4R)-6-Chloro-3,4-dihydrospiro[chromene-2,1'-cyclobutan]-4-yl]-2-(6-methoxy-2-naphthyl)propanamide (Compound No. 19), (2S)—N-[(4S)-6-Chloro-3,4-dihydrospiro[chromene-2,1'-cyclobutan]-4-yl]-2-(6-methoxy-2-naphthyl)propanamide (Compound No. 20), N-(6-Chloro-3,4-dihydrospiro[chromene-2,1'-cyclobutan]-4-yl)-2-(1,2,3,4-tetrahydronaphthalen-1-yl)acetamide (Compound No. 21), N-[(6-Chloro-3,4-dihydrospiro[chromene-2,1'-cyclobutan]-4-yl)]-2-(1,2,3,4-tetrahydronaphthalen-2-yl)acetamide (Compound No. 22), 2-(1,3-Benzodioxol-5-yl)-N-(6-chloro-3,4-dihydrospiro[chromene-2,1'-cyclobutan]-4-yl)acetamide (Compound No. 23), N-(6-Fluoro-3,4-dihydrospiro[chromene-2,1'-cyclobutan]-4-yl)-2-(5-fluoro-3-methyl-1H-indol-2-yl)acetamide (Compound No. 24), N-(6-Chloro-3,4-dihydrospiro[chromene-2,1'-cyclobutan]-4-yl)-2-(5-methoxy-2-methyl-1H-indol-3-yl)acetamide (Compound No. 25), 2-(1,2-Benzisoxazol-3-yl)-N-[(4R)-(6-chloro-3,4-dihydrospiro[chromene-2,1'-cyclobutan]-4-yl)acetamide (Compound No. 26), 2-(1,2-Benzisoxazol-3-yl)-N-[(4S)-(6-chloro-3,4-dihydrospiro[chromene-2,1'-cyclobutan]-4-yl)acetamide (Compound No. 27), N-(6-Chloro-3,4-dihydrospiro[chromene-2,1'-cyclobutan]-4-yl)-3-(2-cyclopentyloxyphenyl)propanamide (Compound No. 28), N-[(4R)-6-Chloro-3,4-dihydrospiro[chromene-2,1'-cyclobutan]-4-yl]-3-(3-cyclopentyloxy)phenylpropanamide (Compound No. 29), N-[(4S)-6-Chloro-3,4-dihydrospiro[chromene-2,1'-cyclobutan]-4-yl]-3-(3-cyclopentyloxy)phenylpropanamide (Compound No. 30), N-[(4R)-(8-Chloro-3,4-dihydrospiro[chromene-2,1'-cyclobutan]-4-yl)-3-(2-cyclopentyloxy)phenyl propanamide (Compound No. 31), N-[(4S)-8-chloro-3,4-dihydrospiro[chromene-2,1'-cyclobutan-4-yl]-3-[2-(cyclopentyloxy)phenylproanamide (Compound No. 32), 7-Benzyloxy-N-(3,4-dihydrospiro[chromene-2,1'-cyclobutan]-4-yl)-3-(2-cyclopentylxoyphenyl)propanamide (Compound No. 33), N-(6-Chloro-3,4-dihydrospiro[chromene-2,1'-cyclobutan]-4-yl)-3-{2-[(isopropylsulfonyl)amino]phenyl}propanamide (Compound No. 34), N-(6-Chloro-3,4-dihydrospiro[chromene-2,1'-cyclobutan]-4-yl)-3-(2-pyridin-2-ylphenyl)propanamide (Compound No. 35), N-(6,8-Dichloro-3,4-dihydrospiro[chromene-2,1'-cyclobutan]-4-yl)-3-(2-pyridin-3-ylphenyl)propanamide (Compound No. 36), N-(3,4-Dihydrospiro[chromene-2,1'-cyclobutan]-4-yl)-3-(2-cyclopentyloxy-3-methoxy)phenylpropanamide (Compound No. 37), N-(6-Chloro-3,4-dihydrospiro[chromene-2,1'-cyclobutan]-4-yl)-3-(2,3-dimethoxy)phenylpropanamide (Compound No. 38), N-(6-Chloro-3,4-dihydrospiro[chromene-2,1'-cyclobutan]-4-yl)-3-(2-isopropoxy-3-methoxy)phenylpropanamide (Compound No. 39), N-(6-Chloro-3,4-dihydrospiro[chromene-2,1'-cyclobutan]-4-yl)-3-(3-chloro-4-methoxy)phenylpropanamide (Compound No. 40), N-(6-Chloro-3,4-dihydrospiro[chromene-2,1'-cyclobutan]-4-yl)-3-(2-cyclopropylmethoxy-3-methoxy)phenylpropanamide (Compound No. 41), N-[(4R)-6-Chloro-3,4-dihydrospiro[chromene-2,1'-cyclobutan]-4-yl)]-3-(2-cyclopentyloxy-3-methoxy)phenylpropanamide (Compound No. 42), N-[(4S)-6-Chloro-3,4-dihydrospiro[chromene-2,1'-cyclobutan]-4-yl)]-3-(2-cyclopentyloxy-3-methoxy)phenylpropanamide (Compound No. 43), N-(6-Chloro-3,4-dihydrospiro[chromene-2,1'-cyclobutan]-4-yl)-3-(2-cyclopentyloxy-3-ethoxy)phenylpropanamide (Compound No. 44), N-(7-Chloro-3,4-dihydrospiro[chromene-2,1'-cyclobutan]-4-yl)-3-(2-cyclopentyloxy-3-methoxy)phenylpropanamide (Compound No. 45), N-(8-Chloro-3,4-dihydrospiro[chromene-2,1'-cyclobutan]-4-yl)-3-(2-ethoxy-3-methoxy)phenylpropanamide (Compound No. 46), N-[(4R)-8-Chloro-3,4-dihydrospiro[chromene-2,1'-cyclobutan]-4-yl)]-3-(2-cyclopentyloxy-3-methoxy)phenylpropanamide (Compound No. 47), N-[(4S)-(8-Chloro-3,4-dihydrospiro[chromene-2,1'-cyclobutan]-4-yl)-3-(2-cyclopentyloxy-3-methoxy)phenylpropanamide (Compound No. 48), N-(6-Chloro-7-methyl-3,4-dihydrospiro[chromene-2,1'-cyclobutan]-4-yl)-3-(2-cyclopentyloxy-3-methoxy)phenylpropanamide (Compound No. 49), N-(5-Benzyloxy-3,4-dihydrospiro[chromene-2,1'-cyclobutan]-4-yl)-3-(2-cyclopentyloxy-3-methoxy)phenylpropanamide (Compound No. 50), N-(5-Hydroxy-3,4-dihydrospiro[chromene-2,1'-cyclobutan]-4-yl)-3-(2-cyclopentyloxy-3-methoxy)phenylpropanamide (Compound No. 51), N-(3,4-Dihydrospiro[chromene-2,1'-cyclobutan]-5-methoxy-4-yl)-3-(2-cyclopentyloxy-3-methoxy)phenylpropanamide (Compound No. 52), (4R)-6-Chloro-N-(3,4-dihydrospiro[chromene-2,1'-cyclobutan]-4-yl)-3-(2-cyclopentyloxy-3-methyl)phenylpropanamide (Compound No. 53), (4S)-6-Chloro-N-(3,4-dihydrospiro[chromene-2,1'-cyclobutan]-4-yl)-3-(2-cyclopentyloxy-3-methyl)phenylpropanamide (Compound No. 54), N-6-Chloro-3,4-dihydrospiro[chromene-2,1'-cyclobutan]-4-yl-3-(2-hydroxy-3-methoxyphenyl)propanamide (Compound No. 55), N-(6-Chloro-3,4-dihydrospiro[chromene-2,1'-cyclobutan]-4-yl)-3-(2-benzyloxy-3-methoxy)phenylpropanamide (Compound No. 56), N-(6 Chloro-3,4-dihydrospiro[chromene-2,1'-cyclobutan]-4-yl)-3-{2-isopropoxy-3-[(methylsulfonyl)amino]phenyl}propanamide (Compound No. 57), N-(8 Chloro-3,4-dihydrospiro[chromene-2,1'-cyclobutan]-4-yl)-3-{2-isopropoxy-3-[(methylsulfonyl)amino]phenyl}propanamide (Compound No. 58), N-(6,8-Dichloro-3,4-dihydrospiro[chromene-2,1'-cyclobutan]-4-yl)-3-(2-cyclopentyloxy-3-methoxy)phenylpropanamide (Compound No. 59), N-(6,8-Dichloro-3,4-dihydrospiro[chromene-2,1'-cyclobutan]-4-yl)-3-{[2-(dimethylamino)ethoxy-3-methoxy]phenyl}propanamide (Compound No. 60), N-(6,8-Dichloro-3,4-dihydrospiro[chromene-2,1'-cyclobutan]-4-yl)-3-{2-propoxy-3-[(methylsulfonyl)amino]phenyl}propanamide (Compound No. 61), N-(6,8-Dichloro-3,4-dihydrospiro[chromene-2,1'-cyclobutan]-4-yl)-3-{2-isopropoxy-5-[(methylsulfonyl)amino]phenyl}propanamide (Compound No. 62), N-(6,8-Dichloro-3,4-dihydrospiro[chromene-2,1'-cyclobutan]-4-yl)-3-{2-butoxy-3-[(methylsulfonyl)amino]phenyl}propanamide (Compound No. 63), N-(6,8-Dichloro-3,4-dihydrospiro[chromene-2,1'-cyclobutan]-4-yl)-3-{2-(cyclopropylmethoxy)-3-[(methylsulfonyl)amino]phenyl}propanamide (Compound No. 64), N-(6,8-Dichloro-3,4-dihydrospiro[chromene-2,1'-cyclobutan]-4-yl)-3-{2-isopropoxy-3-[(methylsulfonyl)amino]phenyl}propanamide (Compound No. 65), N-(6-Chloro-3,4-dihydrospiro[chromene-2,1'-cyclobutan]-4-yl)-3-(1-naphthyl)propanamide (Compound No. 66), N-[4(S)-(6-Chloro-3,4-dihydrospiro[chromene-2,1'-cyclobutan]-4-yl)-3-(2-methoxy)-1-naphthylpropanamide (Compound No. 67), N-[(4R)-6-Chloro-3,4-dihydrospiro[chromene-2,1'-cyclobutan]-4-yl)-3-(4-methoxy)-1-naphthylpropanamide (Compound No. 69), N-[(4S)-6-Chloro-3,4-dihydrospiro[chromene-2,1'-cyclobutan]-4-yl)-3-(4-methoxy)-1-naphthylpropanamide (Compound No. 70), (4R)-6-Chloro-N-(3,4-dihydrospiro[chromene-2,1'-cyclobutan]-4-yl)-3-(4-difluoromethoxy-1-naphthyl)propanamide (Compound No. 71), (4S)-6-Chloro-N-(3,4-dihydrospiro[chromene-2,1'-cyclobutan]-4-yl)-3-(4-difluoromethoxy-1-naphthyl)propanamide (Compound No. 72), N-(6-Chloro-3,4-dihydrospiro[chromene-2,1'-cyclobutan]-4-yl)-3-(2-naphthyl)propanamide (Compound No. 73), N-[4R-(6-Chloro-3,4-dihydrospiro[chromene-2,1'-cyclobutan]-4-yl)-3-(6-methoxy-2-naphthyl)propanamide (Compound No. 74), N-[4S-(6-Chloro-3,4-dihydrospiro[chromene-2,1'-cyclobutan]-4-yl)-3-(6-methoxy-2-naphthyl)propanamide (Compound No. 75), N-(6-Chloro-3,4-dihydrospiro[chromene-2,1'-cyclobutan]-4-yl)-3-(quinolin-2-yl)Propanamide (Compound No. 76), N-(6-Chloro-3,4-dihydrospiro[chromene-2,1'-cyclobutan]-4-yl)-3-(1H-indol-3-yl) propanamide (Compound No. 77), N-(6-Chloro-3,4-dihydrospiro[chromene-2,1'-cyclobutan]-4-yl)-3-(2-methyl, 7-methoxy-1-benzofuran-4-yl)propanamide (Compound No. 78), N-[(4R)-6-Chloro-3,4-dihydrospiro[chromene-2,1'-cyclobutan]-4-yl]-3-(7-methoxy-2-methyl-1-benzofuran-5-yl)propanamide (Compound No. 79), N-[(4S)-6-Chloro-3,4-dihydrospiro[chromene-2,1'-cyclobutan]-4-yl]-3-(7-methoxy-2-methyl-1-benzofuran-5-yl) propanamide (Compound No. 80), 3-(1,4-Benzodioxin-6-yl)-N-(6-fluoro-3,4-dihydrospiro [chromene-2,1'-cyclobutan]-4-yl)propanamide (Compound No. 81), 3-(1,3-Benzodioxol-4-yl)-N-[6-chloro-3,4-dihydrospiro [chromene-2,1'-cyclobutan]-4-yl]propanamide (Compound No. 82), 3-(1,3-Benzodioxol-4-yl)-N-(8-chloro-3,4-dihydrospiro [chromene-2,1'-cyclobutan]-4-yl)propanamide (Compound No. 83), 3-(1,4-Benzodioxin-5-yl)-N-(6-chloro-3,4-dihydrospiro [chromene-2,1'-cyclobutan]-4-yl)propanamide (Compound No. 84), N-(6-Chloro-3,4-dihydrospiro[chromene-2,1'-cyclobutan]-4-yl)-3-(dibenzo[b,d]furan-4-yl)propanamide (Compound No. 85), N-(6-Chloro-3,4-dihydrospiro[chromene-2,1'-cyclopentan]-4-yl)-3-(2-cyclopentyloxy-3-methoxy)propanamide (Compound No. 86), N-(6-Chloro-3,4-dihydrospiro[chromene-2,1'-cyclohexan]-4-yl)-3-(2-cyclopentyloxy-3-methoxy)phenylpropanamide (Compound No. 87), N-(2,2-Dimethyl-3,4-dihydro-2H-chromen-4-yl)-3-(2-cyclopentyloxy-3-methoxy)phenylpropanamide (Compound No. 88), N-(6 Chloro-3,4-dihydro-2H-thiochromen-4-yl)-3-(2-cyclopentyloxy-3-methoxyphenyl)propanamide (Compound No. 89), N-(6-Chloro-3,4-dihydro-2H-thiochromen-4-yl)-3-(2-methoxy-1-naphthyl)propanamide (Compound No. 90), N-(6-Chloro-3,4-dihydrospiro[chromene-2,1'-cyclobutan]-4-yl)-4-(2-cyclopentyloxyphenyl)butanamide (Compound No. 91), N-(6-Chloro-3,4-dihydrospiro[chromene-2,1'-cyclobutan]-4-yl)-4-[2-(cyclopentyloxy)-3-methoxyphenyl]butanamide (Compound No. 92), N-(4R)-6-Chloro-3,4-dihydrospiro[chromene-2,1'-cyclobutan]-4-yl-4-(2-cyclopentyloxy-3-methoxyphenyl)butanamide (Compound No. 93), N-{(4S)-6-Chloro-3,4-dihydrospiro[chromene-2,1'-cyclobutan]-4-yl}-4-[(2-(cyclopentyloxy)-3-methoxyphenyl]butanamide (Compound No. 94), (4R)—N-(8-Chloro-3,4-dihydrospiro[chromene-2,1'-cyclobutan]-4-yl)-4-(2-cyclopentyloxy-3-methoxyphenyl) butanamide (Compound No. 95), (4S)—N-(8-Chloro-3,4-dihydrospiro[chromene-2,1'-cyclobutan]-4-yl)-4-(2-cyclopentyloxy-3-methoxyphenyl) butanamide (Compound No. 96), N-(8-Chloro-6-fluoro-3,4-dihydrospiro[chromene-2,1'-cyclobutan]-4-yl)-4-(2-cyclopentyloxy-3-methoxyphenyl) butanamide (Compound No. 97), N-(6,8-Dichloro-3,4-dihydrospiro[chromene-2,1'-cyclobutan]-4-yl)-4-(2-cyclopentyloxy-3-methoxyphenyl)butanamide (Compound No. 98), N-(7-Benzyloxy-3,4-dihydrospiro[chromene-2,1'-cyclobutan]-4-yl)-4-(2-cyclopentyloxy-3-methoxyphenyl)butanamide (Compound No. 99), N-(7-Hydroxy-3,4-dihydrospiro[chromene-2,1'-cyclobutan]-4-yl)-4-(2-cyclopentyloxy-3-methoxyphenyl)butanamide (Compound No. 100), N-(6-Chloro-3,4-dihydrospiro[chromene-2,1'-cyclobutan]-4-yl)-4-oxo-4-(4-methoxynaphthyl)butanamide (Compound No. 101), N-(6-Chloro-3,4-dihydrospiro[chromene-2,1'-cyclobutan]-4-yl)-4-hydroxy-4-(4-methoxynaphthyl)butanamide (Compound No. 102), N-(6-Chloro-2,2-dimethyl-3,4-dihydro-2H-chromen-4-yl)-4-(2-cyclopentyloxy-3-methoxy)phenylbutanamide (Compound No. 103), N-(6-Chloro-3,4-dihydro-2H-thiochromen-4-yl)-4-(2-cyclopentyloxy-3-methoxyphenyl)butanamide (Compound No. 104) and stereoisomers, enantiomers, diastereomers and pharmaceutically acceptable salts of compounds 1 to 104 are also contemplated.

The present patent application also provides a pharmaceutical composition that includes at least one compound of described herein and at least one pharmaceutically acceptable excipient (such as a pharmaceutically acceptable carrier or diluent). Preferably, the pharmaceutical composition comprises a therapeutically effective amount of at least one compound described herein. The compound of the present invention may be associated with a pharmaceutically acceptable excipient (such as a carrier or a diluent) or be diluted by a carrier, or enclosed within a carrier which may be in the form of a capsule, sachet, paper or other container.

The compounds and pharmaceutical compositions described herein are useful in the treatment of diseases, conditions and/or disorders modulated by TRPV3 receptors.

The present invention further provides a method of treating a disease, condition and/or disorder modulated by TRPV3 receptors in a subject in need thereof by administering to the subject one or more compounds described herein in the amount effective to cause inhibition of such receptor.

Also provided herein are processes for preparing compounds described herein.

DETAILED DESCRIPTION

The present a patent application provides chromane derivatives, which may be used as TRPV3 modulators, and processes for the synthesis of these compounds. Pharmaceutically acceptable salts, enantiomers, diastereomers, of these compounds that may have the same type of activity are also provided. Pharmaceutical compositions containing the described compounds together with pharmaceutically acceptable carriers, excipients or diluents, which can be used for the treatment of diseases, condition and/or disorders mediated by TRPV3 are further provided.

The following definitions apply to the terms as used herein:

The terms "halogen" or "halo" includes fluorine, chlorine, bromine, or iodine

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl). The term "$C_{1-6}$ alkyl" refers to an alkyl chain having 1 to 6 carbon atoms.

The term "alkenyl" refers to an aliphatic hydrocarbon group containing a carbon-carbon double bond and which may be a straight or branched chain having 2 to about 10 carbon atoms, e.g., ethenyl, 1-propenyl, 2-propenyl (allyl), iso-propenyl, 2-methyl-1-propenyl, 1-butenyl, and 2-butenyl.

The term "alkynyl" refers to a straight or branched chain hydrocarbyl radical having at least one carbon-carbon triple bond, and having 2 to about 12 carbon atoms (with radicals having 2 to about 10 carbon atoms being preferred), e.g., ethynyl, propynyl, and butynyl.

The term "alkoxy" denotes an alkyl group attached via an oxygen linkage to the rest of the molecule. Representative examples of such groups are —$OCH_3$ and —$OC_2H_5$.

The term "cycloalkyl" denotes a non-aromatic mono or multicyclic ring system of 3 to about 12 carbon atoms, such as cyclopropyl, cyclobutyl, cyclopentyl, and cyclohexyl. Examples of multicyclic cycloalkyl groups include, but are not limited to, perhydronapthyl, adamantyl and norbornyl groups, bridged cyclic groups or sprirobicyclic groups, e.g., sprio(4,4)non-2-yl.

The term "cycloalkylalkyl" refers to a cyclic ring-containing radical having 3 to about 8 carbon atoms directly attached to an alkyl group. The cycloalkylalkyl group may be attached to the main structure at any carbon atom in the alkyl group that results in the creation of a stable structure. Non-limiting examples of such groups include cyclopropylmethyl, cyclobutylethyl, and cyclopentylethyl.

The term "cycloalkenyl" refers to a cyclic ring-containing radical having 3 to about 8 carbon atoms with at least one carbon-carbon double bond, such as cyclopropenyl, cyclobutenyl, and cyclopentenyl.

The term "aryl" refers to an aromatic radical having 6 to 14 carbon atoms such as phenyl, naphthyl, tetrahydronapthyl, indanyl, and biphenyl.

The term "arylalkyl" refers to an aryl group as defined above directly bonded to an alkyl group as defined above, e.g., —$CH_2C_6H_5$ and —$C_2H_4C_6H_5$.

The term "heterocyclyl" and "heterocyclic ring" refers to a stable 3- to 15-membered ring radical which consists of carbon atoms and from one to five heteroatoms selected from nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heterocyclic or heteroaryl). Examples of such heterocyclic ring radicals include, but are not limited to, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazolyl, imidazolyl, tetrahydroisoquinolinyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxazolidinyl, triazolyl, indanyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofuranyl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, and isochromanyl. The heterocyclic ring radical may be attached to the main structure at any heteroatom or carbon atom that results in the creation of a stable structure.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure.

The term "heteroaryl" refers to an aromatic heterocyclic ring radical. The heteroaryl ring radical may be attached to the main structure at any heteroatom or carbon atom that results in the creation of a stable structure.

The term "heteroarylalkyl" refers to a heteroaryl ring radical directly bonded to an alkyl group. The heteroarylalkyl radical may be attached to the main structure at any carbon atom in the alkyl group that results in the creation of a stable structure.

Unless otherwise specified, the term "substituted" as used herein refers to one or more of the substituents comprising of hydroxy, halogen, carboxyl, cyano, nitro, oxo (═O), thio (═S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenylalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstituted heterocyclic ring, substituted or unsubstituted guanidine, —$COOR^x$, —$C(O)R^x$, —$C(S)R^x$, —$C(O)NR^xR^y$, —$C(O)ONR^xR^3$, —$NR^xCONR^yR^z$, —$N(R^x)SOR^y$, —$N(R^x)SO_2R^y$, —(═N—$N(R^x)R^3$), —$NR^xC(O)OR^3$, —$NR^xR^y$, —$NR^xC(O)R^3$, —$NR^xC(S)R^y$, —$NR^xC(S)NR^yR^z$, —$SONR^xR^y$, —$SO_2NR^xR^y$, —$OR^x$, —$OR^xC(O)NR^yR^z$, —$OR^xC(O)OR^3$, —$OC(O)R^x$, —$OC(O)NR^xR^3$, —$R^xNR^yC(O)R^z$, —$R^xOR^3$, —$R^xC(O)OR^3$, —$R^xC(O)NR^yR^z$, —$R^xC(O)R^3$, —$R^xOC(O)R^3$, —$SR^x$, —$SOR^x$, —$SO_2R^x$, and —$ONO_2$, wherein $R^x$, $R^y$ and $R^z$ are independently selected from hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, or substituted or unsubstituted heterocyclic ring. The substituents in the aforementioned "substituted" groups cannot be further substituted. For example, when the substituent on "substituted alkyl" is "substituted aryl", the substituent on "substituted aryl" cannot be "substituted alkenyl".

The term "treating" or "treatment" of a state, disorder or condition includes:

(1) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition;

(2) inhibiting the state, disorder or condition, i.e., arresting or reducing the development of the disease or at least one clinical or subclinical symptom thereof; or (3) relieving the disease, i.e., causing regression of the state, disorder or condition or at least one of its clinical or subclinical symptoms.

The benefit to a subject to be treated is either statistically significant or at least perceptible to the subject or to the physician.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disorder or condition, is sufficient to effect such treatment. The "therapeutically effective amount" will vary depending on the compound, the disease and its severity and the age, weight, physical condition and responsiveness of the subject to be treated.

The compound described in the present patent application may form salts. Non-limiting examples of pharmaceutically acceptable salts forming part of this patent application include salts derived from inorganic bases, salts of organic bases, salts of chiral bases, salts of natural amino acids and salts of non-natural amino acids. Certain compounds of present patent application are capable of existing in stereoisomeric forms (e.g. diastereomers and enantiomers). With respect to the overall compounds described by the Formula (I), the present patent application extends to these stereoisomeric forms and to mixtures thereof. To the extent prior art teaches synthesis or separation of particular stereoisomers, the different stereoisomeric forms of the present patent application may be separated from one another by the method known in the art, or a given isomer may be obtained by stereospecific or asymmetric synthesis. Tautomeric forms and mixtures of compounds described herein are also contemplated.

Pharmaceutical Compositions

The pharmaceutical composition provided in the present invention include at least one compound described herein and at least one pharmaceutically acceptable excipient (such as a pharmaceutically acceptable carrier or diluent). Preferably, the contemplated pharmaceutical compositions include the compound(s) described herein in an amount sufficient to inhibit TRPV3 receptor in a subject.

The subjects contemplated include, for example, a living cell and a mammal, including human mammal. The compound of the present invention may be associated with a pharmaceutically acceptable excipient (such as a carrier or a diluent) or be diluted by a carrier, or enclosed within a carrier which can be in the form of a capsule, sachet, paper or other container.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone.

The carrier or diluent may include a sustained release material, such as glyceryl monostearate or glyceryl distearate, alone or mixed with a wax.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared by conventional techniques, e.g., as described in Remington: The Science and Practice of Pharmacy, 20$^{th}$ Ed., 2003 (Lippincott Williams & Wilkins). For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be in conventional forms, for example, capsules, tablets, aerosols, solutions, suspensions or products for topical application.

The route of administration may be any route which effectively transports the active compound of the invention to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment). The oral route is preferred.

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Preferable carriers for tablets, dragees, or capsules include lactose, cornstarch, and/or potato starch. A syrup or elixir can be used in cases where a sweetened vehicle can be employed.

A typical tablet that may be prepared by conventional tabletting techniques may contain: (1) Core: Active compound (as free compound or salt thereof), 250 mg colloidal silicon dioxide (Aerosil®), 1.5 mg microcrystalline cellulose (Avicel®), 70 mg modified cellulose gum (Ac-Di-Sol®), and 7.5 mg magnesium stearate; (2) Coating: HPMC, approx. 9 mg Mywacett 9-40 T and approx. 0.9 mg acylated monoglyceride Liquid formulations include, but are not limited to, syrups, emulsions, soft gelatin and sterile injectable liquids, such as aqueous or non-aqueous liquid suspensions or solutions.

For parenteral application, particularly suitable are injectable solutions or suspensions, preferably aqueous solutions with the active compound dissolved in polyhydroxylated castor oil.

Methods of Treatment

The present invention provides compounds and pharmaceutical formulations thereof that are useful in the treatment of diseases, conditions and/or disorders modulated by TRPV3. The connection between therapeutic effect and inhibition of TRPV3 is illustrated, for example in WO2007/056124; Wissenbach, U. et al, *Biology of the cell* (2004), 96, 47-54; Nilius, B. et al., *Physiol Rev* (2007), 87, 165-217; Okuhara, D. Y. et al, *Expert Opinion on Therapeutic Targets*

(2007), 11, 391-401; Hu, H. Z. et al, *Journal of Cellular Physiology*, (2006), 208, 201-212 and references cited therein, all of which are incorporated herein by reference in their entirety and for the purpose stated The present patent application further provides a method of treating a disease, condition and/or disorder modulated by TRPV3 in a subject in need thereof by administering to the subject a therapeutically effective amount of a compound or a pharmaceutical composition of the present invention.

Diseases, conditions, and/or disorders that are modulated by TRPV3 are believed to include, but are not limited to, migraine, arthralgia, cardiac pain arising from an ischemic myocardium, acute pain, chronic pain, neuropathic pain, post-operative pain, pain due to neuralgia (e.g., post-herpetic neuralgia or trigeminal neuralgia), pain due to diabetic neuropathy, dental pain and cancer pain, inflammatory pain conditions (e.g. arthritis and osteoarthritis).

Also Diseases, conditions, and/or disorders that are modulated by TRPV3 are believed to include, but are not limited to pain, nociceptive pain, dental pain, cardiac pain arising from an ischemic myocardium, pain due to migraine, arthralgia, neuropathies, neurodegeneration, retinopathy, neurotic skin disorder, stroke, urinary bladder hypersensitiveness, urinary incontinence, vulvodynia, gastrointestinal disorders such as irritable bowel syndrome, gastro-esophageal reflux disease, enteritis, ileitis, stomach-duodenal ulcer, inflammatory bowel disease, Crohn's disease, celiac disease, an inflammatory disease such as pancreatitis, a respiratory disorder such as allergic and non-allergic rhinitis, asthma or chronic obstructive pulmonary disease, irritation of skin, eye or mucous membrane, dermatitis, pruritic conditions such as uremic pruritus, fervescence, muscle spasms, emesis, dyskinesias, depression, Huntington's disease, memory deficits, restricted brain function, amyotrophic lateral sclerosis (ALS), dementia, arthritis, osteoarthritis, diabetes, obesity, urticaria, actinic keratosis, keratocanthoma, alopecia, Meniere's disease, tinnitus, hyperacusis, anxiety disorders and benign prostate hyperplasia.

General Methods of Preparation

The compounds described herein, including compounds of general formula (I) and (II) and specific examples, are prepared using techniques known to one of ordinary skill in the art. The compounds described herein are prepared through the reaction sequences as depicted in Schemes 1 and 2. All possible stereoisomers are also envisioned within the scope of this invention.

The starting materials for the below reaction schemes are commercially available or can be prepared according to methods known to one skilled in the art or by methods disclosed herein. In general, the compounds according to the present invention may be prepared in the above reaction scheme as follows, wherein all symbols are as defined above.

Compounds of general formula (I), where $R^1$, $R^3$, $R^4$ $R^a$, $R^b$, $R^c$, $R^d$, n, m are as defined above and $R^2$ is an H can be prepared according to Synthetic Scheme 1. Thus, spirocyclic amine of formula (1) is coupled with an aryl substituted carboxylic acid of formula (2) to form an amide of the formula (I). The amide bond formation can be effected by using an appropriate coupling agent such as dicyclohexylcarbodiimide (DCC) or 1-(3-dimethylaminopropyl)-3-ethylcarbodiimide hydrochloride (EDCI) in the presence of an activating agent such as 1-hydroxybenzotriazole (HOBt) and a base in a suitable solvent by following known reaction conditions.

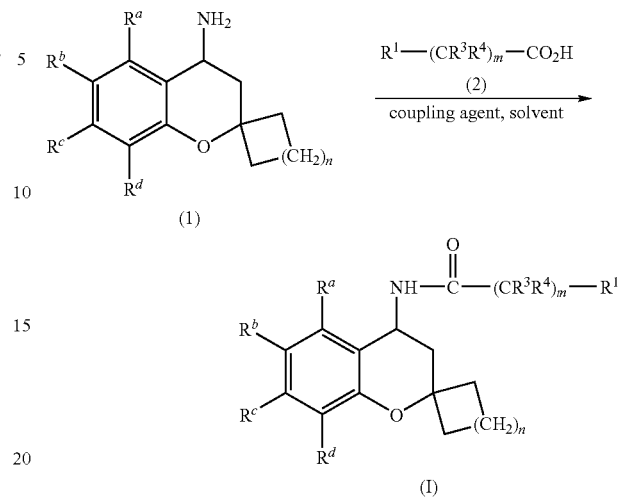

Alternatively, compounds of general formula (I) where $R^1$, $R^3$, $R^4$ $R^a$, $R^b$, $R^c$, $R^d$, n, m are as defined above and $R^2$ is an H, may be prepared from spirocyclic amine of the formula (1) and an acyl halide of the formula (3), where X is a halogen in the presence of a suitable base such as triethylamine and in a suitable solvent such as tetrahydrofuran to give compound of the formula (I).

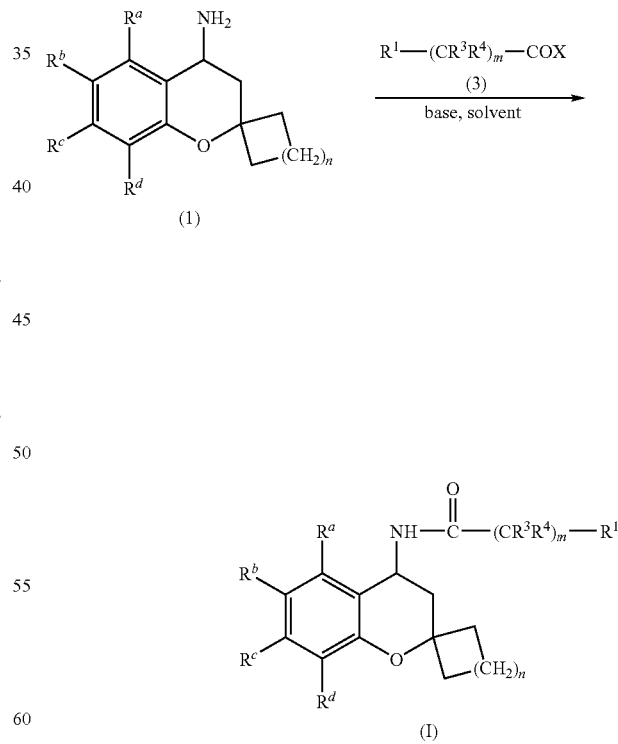

The starting material, 3,4-dihydrospiro[chromene-2,1'-cyclobutan]-4-ones were either commercially available or prepared by the reaction of appropriately substituted 2-hydroxy acetophenones with cyclic ketones in the presence of a base as described in Kabbe, H-J. et al. *Angewandte Chemie* (1982), 94, 254-262. All unsubstituted and substituted 3,4-dihydrospiro[chromene-2,1'-cyclobutan]-4-amines were prepared from 3,4-dihydrospiro[chromene-2,1'-cyclobutan]-4-ones in two steps via its oxime intermediate as described in Ram, P. et al. *Indian J. Chem. Sec B*, (1981), 12, 1063-1067. The optically pure or enriched isomers of 3,4-dihydrospiro[chromene-2,1'-cyclobutan]-4-amines were prepared by resolution of the corresponding amines using appropriate chiral acids as resolving agents. Best results were obtained when optically pure N-tosylprolines were used as resolving agent. Both enantiomers of N-tosyl prolines were prepared as described in Izumiya, N. et al. *Bull. Chem. Soc. Japan.* (1953), 26, 53-56.

Some of the phenylacetic acid derivatives used for the study were commercially available. Commercially unavailable derivatives were prepared by homologation of appropriate benzaldehydes. Tetrahydronaphthalene acetic acids were prepared from the corresponding tetralones by a Wittig-Horner reaction followed by catalytic hydrogenation and ester hydrolysis. Indole-3-acetic acids were prepared from substituted phenyl hydrazines and γ-keto acids by a Fischer indole synthesis as described in Fox, S. S. et al., *J. Am. Chem. Soc.* (1951), 73, 756-2758 and Jackson et al., *Canadian J. Res. Sec. B*, (1935), 13, 170-172. Benzisoxazole acetic acids were prepared from 4-hydroxy coumarin as described in Casini, G. et al. *J. Heterocyclic Chemistry*, (1969), 6, 279-283.

Aryl propanoic acids were prepared from aromatic aldehydes and malonic acid by using a Knoevenagel condensation reaction as the key reaction as described in Rubenstein et al. *J. Chem. Soc.*, (1926), 650. Biaryl propanoic acids were prepared by Suzuki coupling reaction of 2-formyl boronic acids with aryl halides followed by homologation of the resultant aldehyde through malonic acid condensation.

All aryl butanoic acids were prepared from aryl aldehydes by sequential Wittig homolation approach. Thus, substituted benzaldehyde on one carbon homologation using methoxymethylene(triphenyl)phosphorane chloride afforded the corresponding phenyl acetaldehyde derivative, which on further two carbon homologation using methyl(triphenylphosphoranylidene)acetate gave substituted methyl phenyl butenoate. This, on catalytic hydrogenation followed by hydrolysis gave the required aryl butanoic acid derivatives.

EXPERIMENTAL PROCEDURES 3,4-dihydrospiro[chromene-2,1'-cyclobutan]-4-ones

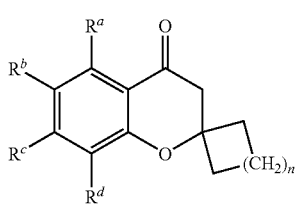

All starting spirochromene-4-ones required for the synthesis of 3,4-dihydrospirochromen-4-amine were prepared by the reaction of commercially available 2-hydroxy acetophenones (1 equivalent) and cycloalkanones (1 equivalent) in presence of excess triethylamine (2-3 equivalents) in refluxing methanol.

3,4-dihydrospiro[chromene-2,1'-cyclobutan]-4-amine

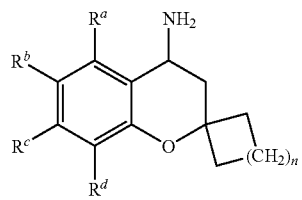

3,4-dihydrospiro[chromene-2,1'-cyclobutan]-4(3H)-one (1.0 equivalent) in ethanol (10 V) was reacted with hydroxylamine hydrochloride (1.5 equivalents) in the presence of aqueous NaOH (3 equivalents) to give (4E)-6-chlorospiro[chromene-2,1'-cyclobutan]-4(3H)-one oximes in good yield. The oxime intermediate (1.0 equivalent) was reduced with Zinc dust (2-3 equivalents) in glacial acetic acid (10 volumes) to give the free amine. All the 4-amino chromene intermediates (Table 1) prepared by this method were characterised by spectral and analytical methods.

General Procedure for the Preparation of Levo Rotatory Amines:

A stirred solution of (±) 3,4-dihydrospiro[chromene-2,1'-cyclobutan]-4-amine derivative (1.0 eq.) in isopropanol (10-12 ml) was refluxed for 10 min to result in a clear solution. L-proline tosylate (0.5 eq.) in isopropanol (10 ml) was then added over 15 min and further stirred at the same temperature for 30 min. The mixture was allowed to cool to room temperature and the diastereomeric salt precipitated out was collected by filtration. The precipitate was dissolved in isopropanol (10 volumes) under reflux and slowly allowed to cool to room temperature. The mixture was further stirred for 18 h. The precipitated salt was collected by filtration. A suspension of the salt in water was basified to pH 8.0 by addition of aqueous $K_2CO_3$ solution. The solution was extracted with ethyl acetate (3×50 ml). The combined organic extracts were dried over $K_2CO_3$ and evaporated under vacuum to give 30-38% of the pure enantiomer. The enantiomeric purity of material was analysed by 250×4.6 mm CHIRALPAK-I A column using n-hexane:isopropanol:diethylamine (98:2:0.1) as mobile phase.

General Procedure for the Preparation of Dextro Rotatory Amines

Optical resolution of (±) 3,4-dihydrospiro[chromene-2,1'-cyclobutan]-4-amine derivative (1.0 eq.) with D-proline tosylate (0.5 eq.) as described above gave the dextro rotatory amines in 30-38% isolated yield. The enantiomeric purity of the material was measured by 250×4.6 mm CHIRALPAK-I A column using n-hexane:isopropanol:diethylamine (98:2:0.1) as mobile phase.

All the intermediates prepared were characterised by spectral and analytical methods before using them for the preparation of compounds of invention. Structural details and selected physicochemical details of 3,4-dihydrospiro[chromene-2,1'-cyclobutan]-4-amines are given in Table 1.

TABLE 1

3,4-dihydrospiro[chromene-2,1'-cyclobutan]-4-amines

| Sr. No. | Structure | Chirality | Mol. Formula | $[\alpha]_D$ (MeOH) |
|---|---|---|---|---|
| Intermediate 1 | 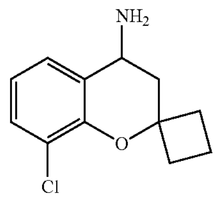 [SMILES: NC1CC2(CCC2)Oc2c(Cl)cccc21] | Racemic | $C_{12}H_{14}ClNO$ | — |
| Intermediate 2 | 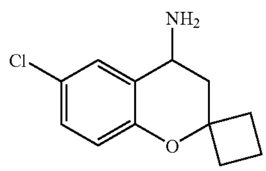 [SMILES: NC1CC2(CCC2)Oc2ccc(Cl)cc21] | Racemic | $C_{12}H_{14}ClNO$ | — |
| Intermediate 3 | 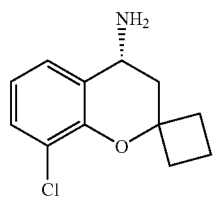 | R-isomer | $C_{12}H_{14}ClNO$ | −6.63° |
| Intermediate 4 | 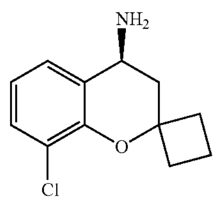 [SMILES: N[C@H]1CC2(CCC2)Oc2c(Cl)cccc21] | S-isomer | $C_{12}H_{14}ClNO$ | +6.30° |
| Intermediate 5 | 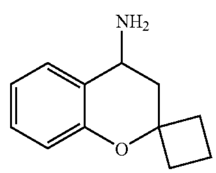 [SMILES: NC1CC2(CCC2)Oc2ccccc21] | Racemic | $C_{12}H_{15}NO$ | |
| Intermediate 6 | 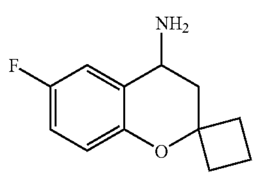 [SMILES: NC1CC2(CCC2)Oc2ccc(F)cc21] | Racemic | $C_{12}H_{14}FNO$ | — |
| Intermediate 7 | 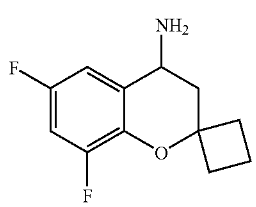 [SMILES: NC1CC2(CCC2)Oc2c(F)cc(F)cc21] | Racemic | $C_{12}H_{13}F2NO$ | — |
| Intermediate 8 | 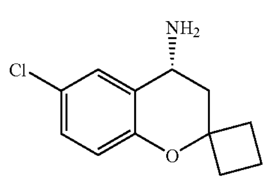 [SMILES: N[C@@H]1CC2(CCC2)Oc2ccc(Cl)cc21] | R-isomer | $C_{12}H_{14}ClNO$ | +8.64° |

TABLE 1-continued 3,4-dihydrospiro[chromene-2,1'-cyclobutan]-4-amines

| Sr. No. | Structure | Chirality | Mol. Formula | $[\alpha]_D$ (MeOH) |
|---|---|---|---|---|
| Intermediate 9 | 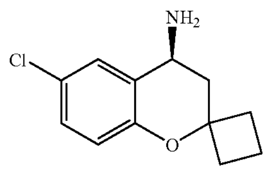 [SMILES: N[C@H]1CC2(CCC2)Oc2ccc(Cl)cc21] | S-isomer | $C_{12}H_{14}ClNO$ | −8.19°, |
| Intermediate 10 | 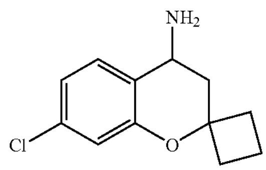 [SMILES: NC1CC2(CCC2)Oc2cc(Cl)ccc21] | Racemic | $C_{12}H_{14}ClNO$ | — |
| Intermediate 11 | 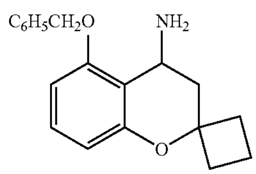 | Racemic | $C_{19}H_{21}NO_2$ | — |
| Intermediate 12 | 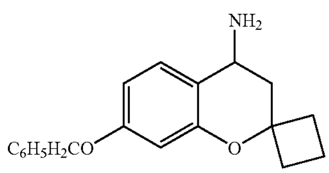 | Racemic | $C_{19}H_{21}NO_2$ | — |
| Intermediate 13 | 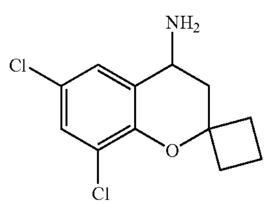 [SMILES: NC1CC2(CCC2)Oc2c(Cl)cc(Cl)cc21] | Racemic | $C_{12}H_{13}Cl_{12}NO$ | — |
| Intermediate 14 | 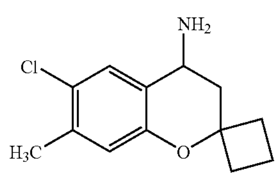 [SMILES: Cc1cc2c(cc1Cl)C(N)CC1(CCC1)O2] | Racemic | $C_{13}H_{16}ClNO$ | — |
| Intermediate 15 | 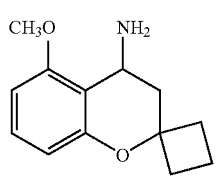 | Racemic | $C_{13}H_{17}NO_2$ | — |
| Intermediate 16 | 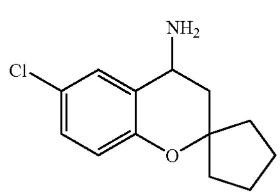 [SMILES: NC1CC2(CCCC2)Oc2ccc(Cl)cc21] | Racemic | $C_{13}H_{16}ClNO$ | — |

TABLE 1-continued 3,4-dihydrospiro[chromene-2,1'-cyclobutan]-4-amines

| Sr. No. | Structure | Chirality | Mol. Formula | $[\alpha]_D$ (MeOH) |
|---|---|---|---|---|
| Intermediate 17 | (6-chloro-spiro[chroman-2,1'-cyclohexan]-4-amine) | Racemic | $C_{14}H_{18}ClNO$ | — |
| Intermediate 18 | (2,2-dimethyl-chroman-4-amine) | Racemic | $C_{11}H_{15}NO$ | — |
| Intermediate 19 | (6-chloro-thiochroman-4-amine) | Racemic | $C_9H_{10}ClNS$ | — |
| Intermediate 20 | (8-chloro-6-fluoro-spiro[chroman-2,1'-cyclobutan]-4-amine) | Racemic | $C_{12}H_{13}ClFNO$ | — |
| Intermediate 21 | (6-chloro-2,2-dimethyl-chroman-4-amine) | Racemic | $C_{11}H_{14}ClNO$ | — |

Selected spectral and analytical data for 3,4-dihydrospiro[chromene-2,1'-cyclobutan]-4-amines have been given below.

Intermediate 1

8-Chloro-3,4-dihydrospiro[chromene-2,1'-cyclobutan]-4-amine $^1$H NMR (300 MHz, CDCl$_3$) δ 1.68-1.77 (m, 4H), 1.74-1.82 (m, 1H), 1.88-1.93 (m, 3H), 2.35-2.57 (m, 2H), 3.99-4.04 (m, 1H), 6.69 (d, J=7.2 Hz, 1H), 7.04 (dd J=2.4, 6.3 Hz, 1H), 7.36 (s, 1H).

Intermediate 2

6-Chloro-3,4-dihydrospiro[chromene-2,1'-cyclobutan]-4-amine $^1$H NMR (300 MHz, CDCl$_3$) δ 1.68-1.77 (m, 4H), 1.85-1.94 (m, 1H), 2.10-2.20 (m, 3H), 2.35-2.45 (m, 2H), 3.93-3.99 (m, 1H), 6.69 (d, J=7.5 Hz, 1H), 7.04 (dd J=2.4, 6.9 Hz, 1H), 7.36 (s, 1H).

Intermediate 3

(4R)-8-Chloro-3,4-dihydrospiro[chromene-2,1'-cyclobutan]-4-amine $^1$H NMR (300 MHz, CDCl$_3$) δ 1.68-1.77 (m, 2H), 1.74-1.82 (m, 2H), 1.88-1.93 (m, 2H), 1.97-2.05 (m, 1H), 2.10-2.19 (m, 1H), 2.23-2.39 (m, 1H), 2.35-2.57 (m, 1H), 3.99-4.04 (m, 1H), 6.80 (t, J=7.2 Hz, 1H), 7.18 (d, J=7.8 Hz, 1H), 7.28 (d, J=7.8 Hz, 1H); HPLC: Retention time of major enantiomer: 26.23 min; ee=96.06%; Specific optical rotation: $[\alpha]_D$=−6.63°, c=1% in methanol.

Intermediate 4

(4S)-8-chloro-3,4-dihydrospiro[chromene-2,1'-cyclobutan]-4-amine $^1$H NMR (300 MHz, CDCl$_3$) δ 1.68-1.77 (m, 2H), 1.74-1.82 (m, 2H), 1.88-1.93 (m, 2H), 1.97-2.05 (m, 1H), 2.10-2.19 (m, 1H), 2.23-2.39 (m, 1H), 2.35-2.57 (m, 1H), 3.99-4.04 (m, 1H), 6.80 (t, J=7.2 Hz, 1H), 7.18 (d, J=7.8 Hz, 1H), 7.28 (d, J=7.8 Hz, 1H); HPLC: Retention time of major enantiomer: 30.57 min; ee=97.14%; Specific optical rotation: [α]$_D$=+6.30°, c=1% in methanol.

Intermediate 5

3,4-dihydrospiro[chromene-2,1'-cyclobutan]-4-amine $^1$H NMR (300 MHz, CDCl$_3$) δ 1.65-1.75 (m, 3H), 1.90-2.00 (m, 3H), 2.30-2.36 (m, 2H), 3.94-4.05 (m, 1H), 5.60-5.66 (m, 2H), 6.80-6.90 (m, 2H), 7.08-7.25 (m, 2H).

Intermediate 6

6-Fluoro-3,4-dihydrospiro[chromene-2,1'-cyclobutan]-4-amine $^1$H NMR (300 MHz, CDCl$_3$) δ 1.67-1.76 (m, 2H), 1.90-2.00 (m, 2H), 2.10-2.20 (m, 2H), 2.28-2.39 (m, 2H), 3.90-4.00 (m, 1H), 5.70-5.76 (m, 1H), 6.70-6.99 (m, 3H), 7.08 (dd, J=2.4, 9.0 Hz, 1H).

Intermediate 7

6,8-Difluoro-3,4-dihydrospiro[chromene-2,1'-cyclobutan]-4-amine $^1$H NMR (300 MHz, CDCl$_3$) δ 1.69-1.82 (m, 5H), 2.05-2.22 (m, 3H), 2.36-2.55 (m, 2H), 3.99-4.06 (m, 1H), 6.69-6.76 (m, 1H), 6.96 (d, J=9.0 Hz, 1H).

Intermediate 8

(4R)-6-Chloro-3,4-dihydrospiro[chromene-2,1'-cyclobutan]-4-amine $^1$H NMR (300 MHz, CDCl$_3$) δ 1.68-1.77 (m, 4H), 1.74-1.82 (m, 1H), 1.88-1.93 (m, 3H), 2.35-2.57 (m, 2H), 3.99-4.04 (m, 1H), 6.69 (d, J=7.2 Hz, 1H), 7.04 (dd J=2.4, 6.3 Hz, 1H), 7.36 (s, 1H); HPLC: Retention time of major enantiomer: 26.57 min; ee=98.03%; Specific Optical Rotation: [α]$_D$=+8.64°, c=1% in methanol.

Intermediate 9

(4S)-6-chloro-3,4-dihydrospiro[chromene-2,1'-cyclobutan]-4-amine $^1$H NMR (300 MHz, CDCl$_3$) δ 1.68-1.77 (m, 4H), 1.74-1.82 (m, 1H), 1.88-1.93 (m, 3H), 2.35-2.57 (m, 2H), 3.99-4.04 (m, 1H), 6.69 (d, J=7.2 Hz, 1H), 7.04 (dd J=2.4, 6.3 Hz, 1H), 7.36 (s, 1H); HPLC: Retention time of major enantiomer: 27.26 min; ee=99.88%; Specific optical rotation: [α]$_D$=−8.19°, c=1% in methanol.

Intermediate 10

7-Chloro-3,4-dihydrospiro[chromene-2,1'-cyclobutan]-4-amine $^1$H NMR (300 MHz, CDCl$_3$) δ 1.59-1.78 (m, 2H), 1.85-1.95 (m, 2H), 2.00-2.10 (m, 2H), 2.16-2.26 (m, 2H), 2.33-2.40 (m, 1H), 2.47-2.57 (m, 1H), 3.99-4.05 (m, 1H), 6.80 (t, J=7.8 Hz, 1H), 7.19 (d, J=7.8 Hz, 1H), 7.28 (d, J=7.8 Hz, 1H).

Intermediate 11

5-Benzyloxy-3,4-dihydrospiro[chromene-2,1'-cyclobutan]-4-amine $^1$H NMR (300 MHz, CDCl$_3$) δ 2.00-2.14 (m, 6H), 2.25-2.40 (m, 2H), 3.73 (br s, 2H), 4.29 (t, J=6.9 Hz, 1H), 5.03-5.12 (m, 2H), 6.50 (dd, J=2.4, 8.4 Hz, 2H), 7.07 (t, J=8.4 Hz, 1H), 7.33-7.40 (m, 5H).

Intermediate 12

7-(Benzyloxy)-3,4-dihydrospiro[chromene-2,1'-cyclobutan]-4-amine $^1$H NMR (300 MHz, CDCl$_3$) δ 1.64-1.71 (m, 1H), 1.84-1.91 (m, 3H), 2.10-2.18 (m, 2H), 2.26-2.34 (m, 1H), 4.45 (br s, 1H), 5.07 (s, 2H), 6.45 (s, 1H), 6.62 (d, J=7.8 Hz, 1H), 7.09 (s, 1H), 7.26-7.37 (m, 5H), 8.69 (br s, 3H).

Intermediate 13

(6,8-Dichloro)-3,4-dihydrospiro[chromene-2,1'-cyclobutan]-4-amine

IR (KBr) 3426, 2920, 1519, 1458, 1243, 1153, 865 cm$^{-1}$; $^1$H NMR (300 MHz, CD$_3$OD) δ 1.74-1.90 (m, 3H), 2.14-2.30 (m, 3H), 2.50-2.57 (m, 2H), 2.62-2.69 (m, 1H), 4.65-4.71 (m, 1H), 6.90-6.96 (m, 1H), 7.43 (s, 2H); ESI-MS (m/z) 258.20 (M+H)$^+$.

Intermediate 14

(6-Chloro-7-methyl)-3,4-dihydrospiro[chromene-2,1'-cyclobutan]-4-amine $^1$H NMR (300 MHz, CDCl$_3$) δ 1.85-1.93 (m, 4H), 2.05-2.19 (m, 4H), 2.72 (s, 3H), 4.15-4.22 (m, 1H), 4.76 (br s, 2H, exchangeable with D$_2$O), 6.67 (s, 1H), 7.45 (s, 1H).

Intermediate 15

5-Methoxy-3,4-dihydrospiro[chromene-2,1'-cyclobutan]-4-amine $^1$H NMR (300 MHz, CDCl$_3$) δ 1.65-1.80 (m, 1H), 1.90-2.08 (m, 3H), 2.20-2.30 (m, 4H), 2.36 (br s, 2H, exchangeable with D$_2$O), 3.83 (s, 3H), 4.15 (t, J=6.3 Hz, 1H), 6.41 (d, J=8.1 Hz, 1H), 6.47 (d, J=8.1 Hz, 1H), 7.06 (t, J=8.4 Hz, 1H).

Intermediate 16

6-Chloro-3,4-dihydrospiro[chromene-2,1'-cyclopentan]-4-amine $^1$H NMR (300 MHz, CDCl$_3$) δ 1.30-1.45 (m, 4H), 1.68-1.78 (m, 4H), 2.05-2.12 (m, 2H), 3.90-4.01 (m, 1H), 6.76 (d, J=8.4 Hz, 1H), 7.02 (dd, J=2.4, 8.4 Hz, 1H), 7.35 (s, 1H).

Intermediate 17

6-Chloro-3,4-dihydrospiro[chromene-2,1'-cyclohexane]-4-amine $^1$H NMR (300 MHz, CDCl$_3$) δ 1.35-1.55 (m, 7H), 1.70-1.78 (m, 3H), 2.07-2.17 (m, 2H), 3.93-3.98 (s, 1H), 6.71 (d, J=8.7 Hz, 1H), 7.04 (dd, J=2.4, 8.7 Hz, 1H), 7.38 (s, 1H).

Intermediate 18

2,2-Dimethylchroman-4-amine $^1$H NMR (300 MHz, DMSO-d$_6$) δ 1.23 (s, 3H), 1.34 (s, 3H), 1.48-1.56 (m, 1H), 1.97-2.03 (m, 3H), 3.80-3.86 (m, 1H), 6.64 (d, J=6.9 Hz, 1H), 6.83 (t, J=7.5 Hz, 1H), 7.05 (t, J=6.9 Hz, 1H), 7.53 (d, J=7.8 Hz, 1H).

Intermediate 19

6-Chlorothiochroman-4-amine $^1$H NMR (300 MHz, CD$_3$OD) δ 2.20-2.26 (m, 1H), 2.32-2.40 (m, 1H), 3.00-3.10 (m, 2H), 4.51 (br s, 1H), 7.07 (d, J=8.4 Hz, 1H), 7.17 (dd, J=2.4, 9.0 Hz, 1H), 7.34 (s, 1H).

Intermediate 20

(8-Chloro-6-fluoro)-3,4-dihydrospiro[chromene-2,1'-cyclobutan]-4-amine $^1$H NMR (300 MHz, CDCl$_3$) δ 1.74-1.86 (m, 1H), 1.92-2.05 (m, 2H), 2.15-2.29 (m, 3H), 2.45-2.55 (m, 1H), 2.63-2.69 (m, 1H), 4.66-4.72 (m, 1H), 7.17-7.26 (m, 2H).

Intermediate 21

(6-Chloro)-2,2-Dimethylchroman-4-amine

IR (KBr) 2977, 2924, 1522, 1482, 1223, 1150, 815 cm$^{-1}$; $^1$H NMR (300 MHz, CDCl$_3$) δ 1.29 (s, 3H), 1.48 (s, 3H), 1.84-1.92 (m, 1H), 2.31-2.37 (m, 1H), 4.57-4.64 (m, 1H), 6.82 (d, J=8.7 Hz, 1H), 7.23 (dd J=2.1, 8.4 Hz, 1H), 7.47 (s, 1H).

EXAMPLES

The present invention is further illustrated by the following examples, which are not to be construed in any way as imposing limitations upon the scope of this disclosure, but rather are intended to be illustrative only.

Example 1

N-(8-Chloro-3,4-dihydrospiro[chromene-2,1'-cyclobutan]-4-yl)-2-phenylacetamide

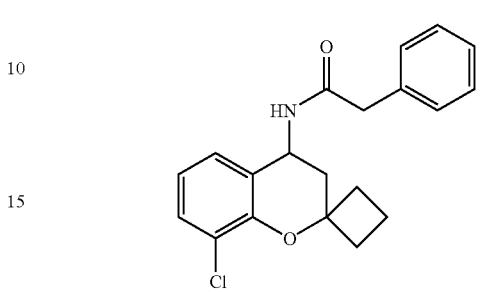

To a well stirred solution of Intermediate 1 (200 mg, 0.898 mmol) in dichloromethane (10 ml) was added EDCI.HCl (258 mg, 1.348 mmol), HOBt (206 mg, 1.348 mmol), phenylacetic acid (183 mg, 1.348 mmol) and triethylamine (375 μl, 2.696 mmol) at room temperature. The reaction mixture was stirred at room temperature under nitrogen for 16 h. The reaction mixture was diluted with water (10 ml) and the layers were separated. The aqueous layer was extracted with chloroform (2×10 ml) and the combined organic layers were washed with water (2×30 ml), brine (30 ml) and dried over Na$_2$SO$_4$. The crude product obtained after evaporation of the solvent under reduced pressure was purified by silica gel column chromatography using 10% acetone in petroleum ether to give 210 mg of the product as an off-white solid; IR (KBr) 3294, 2943, 1647, 1448, 1243, 704 cm$^{-1}$; $^1$H NMR (300 MHz, CDCl$_3$) δ 1.63-1.77 (m, 2H), 1.88-1.92 (m, 1H), 2.01-2.08 (m, 1H), 2.17-2.28 (m, 2H), 2.34-2.41 (m, 2H), 3.64 (s, 2H), 5.26 (q, J=9.3 Hz, 1H), 5.48 (d, J=9.0 Hz, 1H), 6.72 (t, J=7.8 Hz, 1H), 6.89 (d, J=7.8 Hz, 1H), 7.27-7.35 (m, 6H); ESI-MS (m/z) 342.50 (M+H)$^+$.

Example 2

N-(6-Chloro-3,4-dihydrospiro[chromene-2,1'-cyclobutan]-4-yl)-2-(2-methoxyphenyl)-acetamide

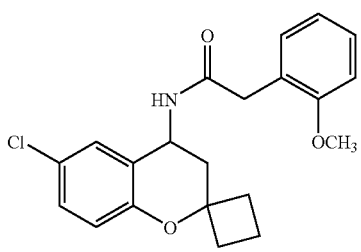 [SMILES: COc1ccccc1CC(=O)NC1CC2(CCC2)Oc2ccc(Cl)cc21]

The title compound was prepared from Intermediate 2 (200 mg, 0.763 mmol) and 2-methoxyphenylacetic acid (190 mg, 1.148 mmol) in presence of EDCI.HCl (219 mg, 1.148 mmol), HOBt (175 mg, 1.148 mmol) and triethylamine (318 μl, 2.289 mmol) in dichloromethane (10 ml) as described in Example 1 for 6 h to give 206 mg of the product as a white solid; IR (KBr) 3272, 2979, 1634, 1475, 1248, 753 cm$^{-1}$; $^1$H NMR (300 MHz, CDCl$_3$) δ 1.65-1.74 (m, 2H), 1.85-2.04 (m, 2H), 2.12-2.20 (m, 2H), 2.24-2.38 (m, 2H), 3.62 (q, J=14.7 Hz, 2H), 3.85 (s, 3H), 5.19 (q, J=9.3 Hz, 1H), 5.78 (d, J=8.4 Hz, 1H), 6.67 (d, J=8.7 Hz, 1H), 6.87-6.94 (m, 3H), 7.02 (d, J=8.4 Hz, 1H), 7.26-7.30 (m, 2H); ESI-MS (m/z) 372.50 (M+H)$^+$.

Example 3

N-(6-chloro-3,4-dihydrospiro[chromene-2,1'cyclobutan]-4-yl)-2-{2-[(methylsulfonyl)-amino]phenyl}acetamide

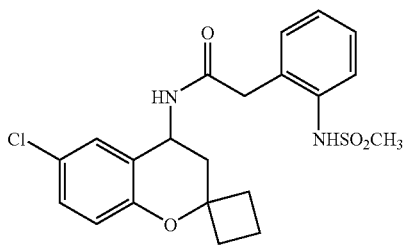

Step 1: N-(6-chloro-3,4-dihydrospiro[chromene-2,1'-cyclobutan]-4-yl)-2-(2-nitrophenyl)acetamide This compound was prepared from Intermediate 2 (500 mg, 1.923 mmol) and 2-nitrophenylacetic acid (348 mg, 1.923 mmol) in presence of EDCI.HCl (191 mg, 1.789 mmol), HOBt (153 mg, 1.789 mmol) and triethylamine (802 μl, 2.289 mmol) in dichloromethane (10 ml) as described in Example 1 for 6 h to give 550 mg of the product as a white solid. $^1$H NMR (300 MHz, CDCl$_3$) δ 1.67-1.84 (m, 5H), 2.10-2.18 (m, 2H), 2.32-2.43 (m, 2H), 3.91 (s, 2H), 5.19-5.27 (m, 1H), 5.92-5.98 (m, 1H), 6.71 (d, J=9.3 Hz, 1H), 7.00-7.08 (m, 1H), 7.45-7.53 (m, 2H), 7.64 (d, J=7.5 Hz, 1H), 8.05 (d, J=8.9 Hz, 1H).

Step 2: 2-(2-aminophenyl)-N-(6-chloro-3,4-dihydrospiro[chromene-2,1'-cyclobutan]-4-yl)acetamide To a well stirred solution of step 1 intermediate (200 mg, 0.512 mmol) in ethanol (5 ml) was added NH$_4$Cl (276 mg, 5.102 mmol) in water (3 ml) at room temperature. The reaction mixture was stirred for 15 min at the same temperature and then heated to 80° C. for 15 min. Iron (86 mg, 1.552 mmol) was added at that same temperature. The reaction mixture was refluxed further for 2 h. The residue obtained after the evaporation of the solvent was extracted with chloroform (2×50 ml). This chloroform layer was passed through celite. The layers were separated. Organic layers were washed with water (2×30 ml), brine (30 ml) and dried over Na$_2$SO$_4$. Solvent was evaporated to give 150 mg of the product.

Step 3: N-(6-chloro-3,4-dihydrospiro[chromene-2,1'-cyclopropan]-4-yl)-2-{2-[(methyl-sulfonyl)amino]phenyl}acetamide To a well stirred solution of step 2 intermediate (150 mg, 0.420 mmol) in dichloromethane (5 ml) was added pyridine (1 ml) at 0° C. Methanesulfonyl chloride (52 mg, 0.462 mmol) was added dropwise at the same temperature. The reaction mixture was stirred at room temperature under nitrogen overnight. The reaction mixture was diluted with water (20 ml) and the layers were separated. The aqueous layer was extracted with chloroform (2×20 ml) and the combined organic layers were washed with water (2×30 ml), brine (30 ml) and dried over Na$_2$SO$_4$. The crude product obtained after evaporation of the solvent under reduced pressure was purified by silica gel column chromatography using 10% acetone in petroleum ether to give 210 mg of the product as an off-white solid; IR (KBr) 3348, 3299, 2937, 1646, 1477, 1153, 976 cm$^{-1}$; $^1$H NMR (300 MHz, CDCl$_3$) δ 1.67-1.79 (m, 3H), 2.10-2.18 (m, 3H), 2.34-2.40 (m, 2H), 3.10 (s, 3H), 3.66 (d, J=6.0 Hz, 2H), 5.16 (q, J=6.9 Hz, 1H), 6.10 (d, J=9.0 Hz, 1H), 6.72 (d, J=8.7 Hz, 1H), 6.97 (s, 1H), 7.06 (d, J=9.0 Hz, 1H), 7.17 (d, J=7.5 Hz, 1H), 7.20 (s, 1H), 7.31 (t, J=6.6 Hz, 1H), 7.49 (d, J=8.4 Hz, 1H), 9.09 (s, 1H); ESI-MS (m/z) 433.38 (M−H)$^−$.

Example 4

N-(6-Chloro-3,4-dihydrospiro[chromene-2,1'-cyclobutan]-4-yl)-2-(2-(cyclopentyloxy)-3-methoxyphenyl)acetamide The title compound was prepared from Intermediate 2 (200 mg, 0.763 mmol) in dichloromethane (10 ml) and [2-(cyclopentyloxy)-3-methoxyphenyl]acetic acid (283 mg, 1.153 mmol) in presence of EDCI.HCl (221 mg, 1.153 mmol), HOBt (178 mg, 1.153 mmol) and triethylamine (321 μl, 2.307 mmol) as described in Example 1 to give 236 mg of the product as a white solid; IR (KBr) 3311, 2963, 1653, 1529, 1476, 1266, 813 cm$^{-1}$; $^1$H NMR (300 MHz, CDCl$_3$) δ 1.58-1.64 (m, 6H), 1.70-1.80 (m, 6H), 1.97-2.04 (m, 1H), 2.13 (t, J=7.8 Hz, 2H), 2.26-2.33 (m, 2H), 3.58 (q, J=14.4 Hz, 2H), 3.81 (s, 3H), 4.99 (br s, 1H), 5.09-5.17 (m, 1H), 6.31 (d, J=8.1 Hz, 1H), 6.66 (t, J=8.4 Hz, 1H), 6.81-7.02 (m, 4H).

Example 5

N-[(4R)-8-Chloro-3,4-dihydrospiro[chromene-2,1'-cyclobutan]-4-yl]-2-(2-cyclopentyloxy-3-methoxy)phenylacetamide

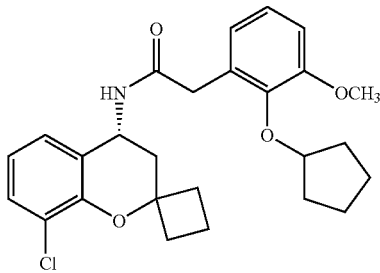 [SMILES: COc1cccc(CC(=O)N[C@@H]2CC3(CCC3)Oc3c(Cl)cccc32)c1OC1CCCC1]

The title compound was prepared from Intermediate 3 (150 mg, 0.675 mmol) and 2-(2-cyclopentyloxy-3-methoxyphenyl)acetic acid (167 mg, 0.675 mmol) in presence of EDCI.HCl (192 mg, 1.047 mmol), HOBt (154 mg, 1.047 mmol) and triethylamine (275 μl, 2.008 mmol) in dichloromethane (10 ml) as described in Example 1 for 5 h to give 181 mg of the product as a white solid; IR (KBr) 3309, 2934, 1654, 1451, 1074, 968 cm$^{-1}$; $^1$H NMR (300 MHz, CDCl$_3$) δ 1.60-1.74 (m, 11H), 1.84-1.95 (m, 1H), 2.04-2.10 (m, 1H), 2.16-2.24 (m, 2H), 2.31-2.44 (m, 2H), 3.62 (d, J=7.8 Hz, 2H), 3.80 (s, 3H), 4.96 (br s, 1H), 5.18 (d, J=8.7 Hz, 1H), 6.28 (d, J=8.7 Hz, 1H), 6.68 (t, J=7.8 Hz, 1H), 6.79-6.88 (m, 2H), 6.96 (t, J=7.8 Hz, 1H), 7.15 (d, J=7.8 Hz, 1H); APCI-MS (m/z) 454.72 (M–H)$^-$.

Example 6

N-[(4S)-8-Chloro-3,4-dihydrospiro[chromene-2,1'-cyclobutan]-4-yl]-2-(2-cyclopentyl-oxy-3-methoxy)phenylacetamide

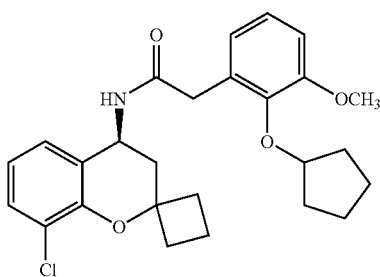 [SMILES: COc1cccc(CC(=O)N[C@H]2CC3(CCC3)Oc3c(Cl)cccc32)c1OC1CCCC1]

The title compound was prepared from Intermediate 4 (150 mg, 0.675 mmol) and 2-(2-cyclopentyloxy-3-methoxyphenyl)acetic acid (167 mg, 0.675 mmol) in presence of EDCI.HCl (192 mg, 1.047 mmol), HOBt (154 mg, 1.047 mmol) and triethylamine (275 μl, 2.008 mmol) in dichloromethane (10 ml) as described in Example 1 to give 200 mg of the product as a white solid; IR (KBr) 3308, 2934, 1654, 1527, 1451, 1074, 968 cm$^{-1}$; $^1$H NMR (300 MHz, CDCl$_3$) δ 1.60-1.74 (m, 11H), 1.83-1.93 (m, 1H), 2.00-2.10 (m, 1H), 2.16-2.24 (m, 2H), 2.31-2.44 (m, 2H), 3.62 (d, J=7.8 Hz, 2H), 3.79 (s, 3H), 4.96 (br s, 1H), 5.18 (d, J=8.7 Hz, 1H), 6.28 (d, J=8.7 Hz, 1H), 6.68 (t, J=7.8 Hz, 1H), 6.79-6.88 (m, 2H), 6.97 (t, J=7.8 Hz, 1H), 7.16 (d, J=7.8 Hz, 1H); APCI-MS (m/z) 454.72 (M–H)$^-$.

Example 7

N-(6-Chloro-3,4-dihydrospiro[chromene-2,1'-cyclobutan]-4-yl)-2-(3,4-dimethoxyphenyl)acetamide

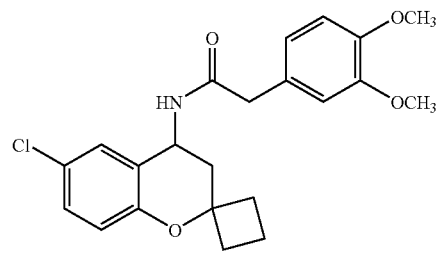 [SMILES: COc1ccc(CC(=O)NC2CC3(CCC3)Oc3ccc(Cl)cc32)cc1OC]

The title compound was prepared from Intermediate 2 (200 mg, 0.763 mmol) and 3,4-dimethoxyphenylacetic acid (224 mg, 1.145 mmol) in presence of EDCI.HCl (219 mg, 1.145 mmol), HOBt (175 mg, 1.145 mmol) and triethylamine (425 μl, 3.053 mmol) in dichloromethane (10 ml) as described in Example 1 to give 217 mg of the product as a white solid; IR (KBr) 3232, 2938, 1634, 1478, 1241, 813 cm$^{-1}$; $^1$H NMR (300 MHz, CDCl$_3$) δ 1.62-1.70 (m, 2H), 1.87-1.90 (m, 2H), 1.99-2.15 (m, 2H), 2.18-2.37 (m, 2H), 3.60 (q, J=16.2 Hz, 2H), 3.85 (s, 6H), 5.23 (q, J=9.6 Hz, 1H), 5.48 (d, J=9.0 Hz, 1H), 6.68 (d, J=9.0 Hz, 1H), 6.77-6.84 (m, 3H), 6.96 (s, 1H), 7.04 (d, J=8.4 Hz, 1H); ESI-MS (m/z) 401.27 (100%).

Example 8

N-(6-Chloro-3,4-dihydrospiro[chromene-2,1'-cyclobutan]-4-yl)-2-pyridin-2-ylacetamide

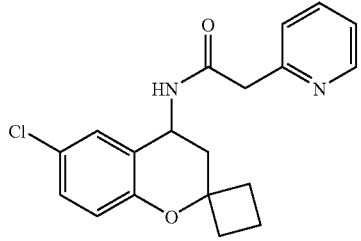 [SMILES: O=C(Cc1ccccn1)NC1CC2(CCC2)Oc2ccc(Cl)cc21]

The title compound was prepared from Intermediate 2 (200 mg, 0.898 mmol) and 2-pyridylacetic acid (234 mg, 1.348 mmol) in presence of EDCI.HCl (258 mg, 1.348 mmol), HOBt (206 mg, 1.348 mmol) and triethylamine (375 μl, 2.696 mmol) in dichloromethane (10 ml) as described in Example 1 to give 151 mg of the product as a white solid; IR (KBr) 3272, 2936, 1644, 1477, 1265, 812 cm$^{-1}$; $^1$H NMR (300 MHz, DMSO-d$_6$) δ 1.65-1.88 (m, 3H), 2.02-2.20 (m, 3H), 2.25-2.35 (m, 2H), 3.71 (q, J=12.0 Hz, 2H), 5.00-5.15 (m, 1H), 6.73 (t, J=7.8 Hz, 1H), 6.76 (d, J=8.4 Hz, 1H), 7.10-7.20 (m, 2H), 7.22-7.30 (m, 1H), 7.70-7.80 (m, 1H), 8.49 (s, 1H), 8.62 (d, J=8.4 Hz, 1H); ESI-MS (m/z) 343.21 (M+H)⁺.

Example 9

N-(3,4-dihydrospiro[chromene-2,1'-cyclobutan]-4-yl)-2-(1-naphthyl)acetamide

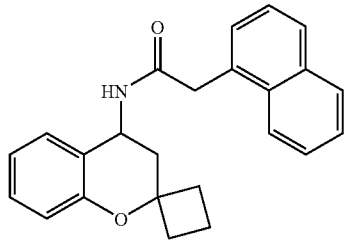 [SMILES: O=C(Cc1cccc2ccccc12)NC1CC2(CCC2)Oc2ccccc21]

The title compound was prepared from Intermediate 5 (150 mg, 0.806 mmol) and 1-naphthylacetic acid (150 mg, 0.806 mmol) in presence of EDCI.HCl (230 mg, 1.209 mmol), HOBt (185 mg, 1.209 mmol) and triethylamine (336 μl, 2.418 mmol) in dichloromethane (10 ml) as described in Example 1 for 3 h to give 151 mg of the product as a white solid; IR (KBr) 3278, 2932, 1635, 1551, 1229, 771 cm⁻¹; ¹H NMR (300 MHz, CDCl₃) δ 1.50-1.60 (m, 2H), 1.70-1.80 (m, 2H), 2.05-2.13 (m, 3H), 2.25 (dd, J=5.7, 13.5 Hz, 1H), 4.10 (s, 2H), 5.18-5.24 (m, 1H), 5.35-5.42 (m, 1H), 6.58-6.70 (s, 3H), 7.00 (t, J=7.8 Hz, 1H), 7.30-7.39 (m, 2H), 7.48-7.59 (m, 2H), 7.70-7.77 (m, 1H), 7.84 (d, J=8.4 Hz, 1H), 8.00 (d, J=7.8 Hz, 1H); APCI-MS (m/z) 358.36 (M+H)⁺.

Example 10

N-(6-Fluoro-(3,4-dihydrospiro[chromene-2,1'-cyclobutan]-4-yl)-2-(1-naphthyl)acetamide

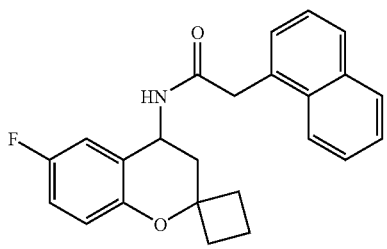 [SMILES: O=C(Cc1cccc2ccccc12)NC1CC2(CCC2)Oc2ccc(F)cc21]

The title compound was prepared from Intermediate 6 (300 mg, 1.611 mmol) and 1-naphthylacetic acid (400 mg, 1.933 mmol) in presence of EDCI.HCl (463 mg, 2.455 mmol), HOBt (246 mg, 1.611 mmol) and triethylamine (926 μl, 4.835 mmol) in dichloromethane (10 ml) as described in Example 1 to give 310 mg of the product as a white solid; IR (KBr) 3280, 2933, 1643, 1485, 1202, 795 cm⁻¹; ¹H NMR (300 MHz, CDCl₃) δ 1.44-1.54 (m, 2H), 1.75-1.80 (m, 2H), 2.02-2.10 (m, 3H), 2.13-2.26 (m, 1H), 4.11 (q, J=16.5 Hz, 2H), 5.19 (q, J=9.0 Hz, 1H), 5.32 (d, J=8.4 Hz, 1H), 6.42 (dd, J=3.0, 6.3 Hz, 1H), 6.60-6.68 (m, 1H), 6.69-6.73 (m, 1H), 7.39-7.50 (m, 2H), 7.52-7.61 (m, 2H), 7.77-7.87 (m, 2H), 7.99 (d, J=8.1 Hz, 1H); ESI-MS (m/z) 376.32 (M+H)⁺.

Example 11

N-[(4R)-6,8-difluoro-3,4-dihydrospiro[chromene-2,1'-cyclobutan]-4-yl]-2-(1-naphthyl)acetamide

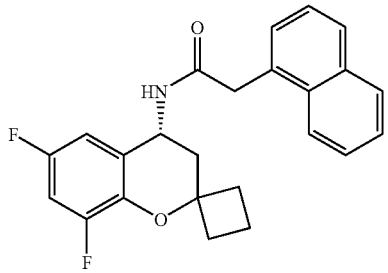 [SMILES: O=C(Cc1cccc2ccccc12)N[C@@H]1CC2(CCC2)Oc2c(F)cc(F)cc21]

The title compound was prepared from Intermediate 7 (95 mg, 0.421 mmol) and 1-naphthylacetic acid (117 mg, 0.632 mmol) in presence of EDCI.HCl (121 mg, 0.632 mmol), HOBt (96 mg, 0.632 mmol) and triethylamine (176 μl, 1.265 mmol) in dichloromethane (10 ml) as described in Example 1 to give 91 mg of the product as an off-white solid; IR (KBr) 3272, 2936, 1645, 1565, 1484, 1226, 794 cm⁻¹; ¹H NMR (300 MHz, CDCl₃) δ 1.59-1.61 (m, 2H), 1.77-1.87 (m, 2H), 2.10-2.18 (m, 2H), 2.24-2.30 (m, 2H), 4.12 (q, J=16.5 Hz, 2H), 5.16-5.24 (m, 1H), 5.30-5.36 (m, 1H), 6.22 (d, J=8.7 Hz, 1H), 6.55-6.62 (m, 1H), 7.39-7.44 (m, 2H), 7.54-7.61 (m, 2H), 7.79 (d, J=6.9 Hz, 1H), 7.85 (d, J=8.1 Hz, 1H), 7.98 (d, J=7.8 Hz, 1H); ESI-MS (m/z) 409.19 (M)⁺.

Example 12

N-[(4R)-6-Chloro-3,4-dihydrospiro[chromene-2,1'-cyclobutan]-4-yl]-2-(1-naphthyl)acetamide

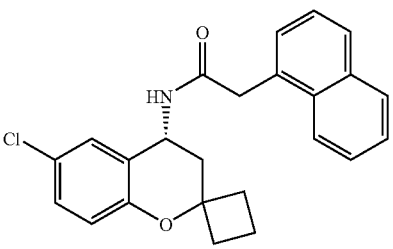 [SMILES: O=C(Cc1cccc2ccccc12)N[C@@H]1CC2(CCC2)Oc2ccc(Cl)cc21]

The title compound was prepared from Intermediate 8 (150 mg, 0.674 mmol) and 1-naphthylacetic acid (188 mg, 1.011 mmol) in presence of EDCI.HCl (193 mg, 1.011 mmol), HOBt (154 mg, 1.011 mmol) and triethylamine (281 μl, 2.022 mmol) in dichloromethane (10 ml) as described in Example 1 to give 123 mg of the product as a white solid; IR (KBr) 3277, 2952, 1640, 1478, 1236, 751 cm⁻¹; ¹H NMR (300 MHz, CDCl₃) δ 1.46-1.53 (m, 2H), 1.75-1.81 (m, 2H), 2.07-2.16 (m, 3H), 2.22-2.39 (m, 1H), 4.12 (q, J=16.5 Hz, 2H), 5.19 (q, J=9.6 Hz, 1H), 5.33 (d, J=8.4 Hz, 1H), 6.58 (d, J=8.7 Hz, 1H), 6.66 (s, 1H), 6.93 (d, J=7.2 Hz, 1H), 7.23-7.42 (m, 2H), 7.54

(t, J=14.1 Hz, 1H), 7.62 (t, J=7.5 Hz, 1H), 7.82 (dd, J=8.4, 10.2 Hz, 2H), 7.99 (d, J=8.7 Hz, 1H); ESI-MS (m/z) 392.49 (M+H)+.

Example 13

N-[(4S)-6-Chloro-3,4-dihydrospiro[chromene-2,1'-cyclobutan]-4-yl]-2-(1-naphthyl)-acetamide

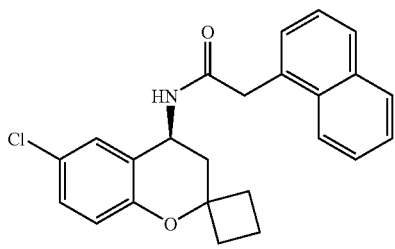 [SMILES: O=C(Cc1cccc2ccccc12)N[C@H]1CC2(CCC2)Oc2ccc(Cl)cc21]

The title compound was prepared from Intermediate 9 (200 mg, 0.896 mmol) and 1-naphthylacetic acid (200 mg, 1.076 mmol) in presence of EDCI.HCl (257 mg, 1.345 mmol), HOBt (206 mg, 1.341 mmol) and triethylamine (374 µl, 2.692 mmol) in dichloromethane (10 ml) as described in Example 1 to give 169 mg of the product as a white solid; IR (KBr) 3272, 2942, 1642, 1473, 1266, 776 cm⁻¹; ¹H NMR (300 MHz, CDCl₃) δ 1.45-1.53 (m, 2H), 1.74-1.82 (m, 2H), 2.06-2.12 (m, 3H), 2.14-2.28 (m, 1H), 4.11 (q, J=16.5 Hz, 2H), 5.19 (q, J=9.6 Hz, 1H), 5.33 (d, J=9.0 Hz, 1H), 6.57 (d, J=8.7 Hz, 1H), 6.66 (s, 1H), 6.93 (d, J=6.3 Hz, 1H), 7.39-7.43 (m, 2H), 7.51 (t, J=6.9 Hz, 1H), 7.61 (t, J=6.9 Hz, 1H), 7.70 (dd, J=1.8, 5.1 Hz, 1H), 7.85 (d, J=7.8 Hz, 1H), 7.99 (d, J=8.1 Hz, 1H); ESI-MS (m/z) 392.45 (M+H)+.

Example 14

N-(7-Chloro-3,4-dihydrospiro[chromene-2,1'-cyclobutan]-4-yl)-2-(1-naphthyl)acetamide

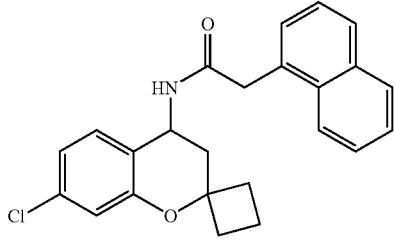 [SMILES: O=C(Cc1cccc2ccccc12)NC1CC2(CCC2)Oc2cc(Cl)ccc21]

The title compound was prepared from Intermediate 10 (200 mg, 0.761 mmol) and 1-naphthylacetic acid (171 mg, 0.913 mmol) in presence of EDCI.HCl (221 mg, 1.141 mmol), HOBt (176 mg, 1.141 mmol) and triethylamine (317 µl, 2.283 mmol) in THF (5 ml) as described in Example 1 to give 250 mg of the product as a white solid; IR (KBr) 3236, 2945, 1638, 1412, 1223, 788 cm⁻¹; ¹H NMR (300 MHz, CDCl₃) δ 1.47-1.55 (m, 2H), 1.72-1.78 (m, 2H), 2.09 (t, J=7.8 Hz, 3H), 2.16-2.26 (m, 1H), 4.09 (q, J=6.9 Hz, 2H), 5.11-5.19 (m, 1H), 5.29 (d, J=8.4 Hz, 1H), 6.55 (s, 2H), 6.66 (s, 1H), 7.35-7.42 (m, 2H), 7.49-7.59 (m, 2H), 7.77 (d, J=7.2 Hz, 1H), 7.82 (d, J=7.8 Hz, 1H), 7.98 (d, J=7.8 Hz, 1H); APCI-MS (m/z) 392.12 (M+H)+.

Example 15

N-[(4R)-8-Chloro-3,4-dihydrospiro[chromene-2,1'-cyclobutan]-4-yl]-2-(1-naphthyl)-acetamide

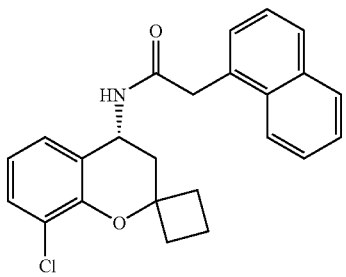 [SMILES: O=C(Cc1cccc2ccccc12)N[C@@H]1CC2(CCC2)Oc2c(Cl)cccc21]

The title compound was prepared from Intermediate 3 (100 mg, 0.448 mmol) and 1-naphthylacetic acid (99 mg, 0.531 mmol) in presence of EDCI.HCl (128 mg, 0.672 mmol), HOBt (102 mg, 0.672 mmol) and triethylamine (185 µl, 2.022 mmol) in dichloromethane (10 ml) as described in Example 1 to give 100 mg of the product as a white solid; IR (KBr) 3271, 2938, 1636, 1449, 1244, 778 cm⁻¹; ¹H NMR (300 MHz, CDCl₃) δ 1.62-1.78 (m, 5H), 2.11-2.30 (m, 3H), 4.09 (q, J=16.8 Hz, 2H), 5.23 (q, J=9.3 Hz, 1H), 5.46 (d, J=7.8 Hz, 1H), 6.52 (t, J=7.2 Hz, 1H), 6.60 (d, J=7.2 Hz, 1H), 7.07 (d, J=7.8 Hz, 1H), 7.37-7.42 (m, 2H), 7.48-7.59 (m, 2H), 7.77 (t, J=6.3 Hz, 1H), 7.84 (d, J=7.8 Hz, 1H), 7.99 (d, J=8.1 Hz, 1H); ESI-MS (m/z) 392.59 (M+H)+.

Example 16

N-[(4S)-8-Chloro-3,4-dihydrospiro[chromene-2,1'-cyclobutan]-4-yl]-2-(1-naphthyl)-acetamide

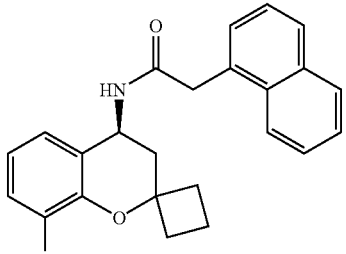

The title compound was prepared from Intermediate 4 (150 mg, 0.668 mmol) and 1-naphthylacetic acid (149 mg, 0.801 mmol) in presence of EDCI.HCl (193 mg, 1.008 mmol), HOBt (154 mg, 1.008 mmol) and triethylamine (279 µl, 2.004 mmol) in dichloromethane (10 ml) as described in Example 1 to give 150 mg of the product as an off-white solid; IR (KBr) 3275, 2939, 1636, 1244, 778 cm⁻¹; ¹H NMR (300 MHz, CDCl₃) δ 1.61-1.79 (m, 5H), 2.10-2.30 (m, 3H), 4.08 (q, J=16.5 Hz, 2H), 5.22 (q, J=8.7 Hz, 1H), 5.43 (d, J=8.1 Hz, 1H), 6.52 (t, J=7.2 Hz, 1H), 6.60 (d, J=7.2 Hz, 1H), 7.07 (d, J=7.8 Hz, 1H), 7.35-7.42 (m, 2H), 7.48-7.60 (m, 2H), 7.77 (t, J=6.3 Hz, 1H), 7.84 (d, J=7.8 Hz, 1H), 7.98 (d, J=8.1 Hz, 1H); ESI-MS (m/z) 392.63 (M+H)⁺.

Example 17

N-(5-Hydroxy-3,4-dihydrospiro[chromene-2,1'-cyclobutan]-4-yl)-2-(1-naphthyl)-acetamide

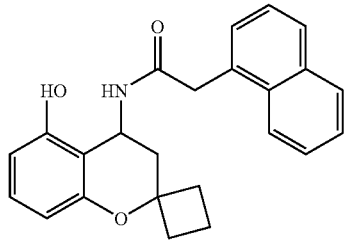 [SMILES: O=C(Cc1cccc2ccccc12)NC1CC2(CCC2)Oc2cccc(O)c21]

Step 1: N-(5-Benzyloxy-3,4-dihydrospiro[chromene-2,1'-cyclobutan]-4-yl)-2-(1-naphthyl)acetamide This compound was prepared from Intermediate 11 (872 mg, 2.954 mmol) and 1-naphthylacetic acid (500 mg, 2.685 mmol) in presence of EDCI.HCl (772 mg, 4.027 mmol), HOBt (411 mg, 2.685 mmol) and triethylamine (1.123 ml, 2.274 mmol) in dichloromethane (10 ml) as described in Example 1 to give 420 mg of the product as a white solid; IR (KBr) 3293, 2929, 1638, 1466, 1120, 778 cm⁻¹; ¹H NMR (300 MHz, CDCl₃) δ 1.25-1.35 (m, 2H), 1.45-1.52 (m, 1H), 1.58-1.64 (m, 1H), 1.94-2.00 (m, 2H), 2.15-2.25 (m, 2H), 3.64-3.70 (m, 1H), 3.98-4.04 (m, 1H), 4.87-5.02 (m, 2H), 5.23-5.30 (m, 2H), 6.34-6.40 (m, 2H), 7.00-7.07 (m, 3H), 7.28-7.39 (m, 7H), 7.67-7.75 (m, 2H), 7.85-7.91 (m, 1H); APCI-MS (m/z) 464.5 (M+H)⁺.

Step 2: N-(5-Hydroxy-3,4-dihydrospiro[chromene-2,1'-cyclobutan]-4-yl)-2-(1-naphthyl)acetamide Deprotection of step 1 intermediate (400 mg, 0.863 mmol) was accomplished using 50% Pd/C (80 mg) in methanol (70 ml) at 65 psi pressure for 8 h in Paar apparatus. The reaction mixture was filtered through a celite bed. The filtrate was concentrated under reduced pressure to afford a crude residue which was purified by silica gel column chromatography to give 115 mg of the product as a white solid; IR (KBr) 3293, 2972, 1608, 1469, 1120, 775 cm⁻¹; ¹H NMR (300 MHz, CDCl₃) δ 1.26-1.35 (m, 1H), 1.89-1.96 (m, 2H), 2.12-2.22 (m, 2H), 3.64-3.70 (m, 1H), 3.98-4.04 (m, 1H), 4.85-4.91 (m, 1H), 5.00-5.08 (m, 1H), 5.20-2.30 (m, 2H), 6.33-6.42 (m, 2H), 6.99-7.07 (m, 2H), 7.28-7.42 (m, 5H), 7.68 (d, J=7.5 Hz, 1H), 7.75-7.86 (m, 1H), 10.02 (br s 1H); ESI-MS (m/z) 374.37 (M+H)⁺.

Example 18

N-(6-Chloro-3,4-dihydrospiro[chromene-2,1'-cyclobutan]-4-yl)-2-(2-naphthyl)acetamide

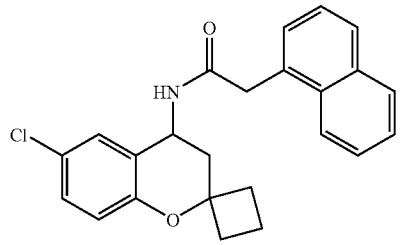 [SMILES: O=C(Cc1cccc2ccccc12)NC1CC2(CCC2)Oc2ccc(Cl)cc21]

The title compound was prepared from Intermediate 2 (200 mg, 0.764 mmol) and 2-naphthylacetic acid (213 mg, 1.141 mmol) in presence of EDCI.HCl (213 mg, 1.145 mmol), HOBt (176 mg, 1.145 mmol) and triethylamine (425 µl, 3.052 mmol) in dichloromethane (10 ml) as described in Example 1 to give 193 mg of the product as a white solid; IR (KBr) 3262, 2933, 1643, 1474, 1230, 816 cm⁻¹; ¹H NMR (300 MHz, CDCl₃) δ 1.63-1.77 (m, 2H), 1.84-1.92 (m, 2H), 1.95-2.02 (m, 2H), 2.16-2.36 (m, 2H), 3.82 (s, 2H), 5.24 (q, J=9.6 Hz, 1H), 5.50 (d, J=8.7 Hz, 1H), 6.65 (d, J=8.4 Hz, 1H), 7.00 (d, J=9.3 Hz, 2H), 7.39 (d, J=8.4 Hz, 1H), 7.45-7.50 (m, 2H), 7.73 (s, 1H), 7.78-7.86 (m, 3H); ESI-MS (m/z) 392.58 (M+H)⁺.

Example 19

(2S)—N-[(4R)-6-Chloro-3,4-dihydrospiro[chromene-2,1'-cyclobutan]-4-yl]-2-(6-methoxy-2-naphthyl)propanamide

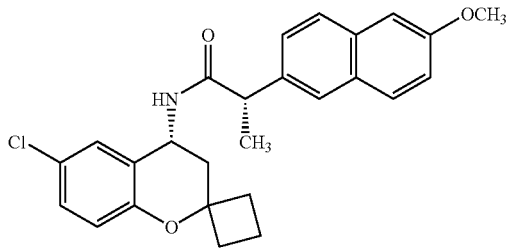 [SMILES: COc1ccc2cc([C@H](C)C(=O)N[C@@H]3CC4(CCC4)Oc4ccc(Cl)cc43)ccc2c1]

The title compound was prepared from Intermediate 8 (200 mg, 0.769 mmol) and (2S)-2-(6-methoxy-2-naphthyl)propanoic acid (213 mg, 0.923 mmol) in presence of EDCI.HCl (221 mg, 1.153 mmol), HOBt (176 mg, 1.153 mmol) and triethylamine (321 µl, 2.307 mmol) in dichloromethane (10 ml) as described in Example 1 to give 112 mg of the product as a white solid; IR (KBr) 3351, 2938, 1652, 1518, 1482, 1261, 857 cm⁻¹; ¹H NMR (300 MHz, CDCl₃) δ 1.64 (s, 3H), 1.66 (s, 2H), 1.80-1.90 (m, 2H), 2.08-2.14 (m, 3H), 2.21-2.27 (m, 1H), 3.76 (q, J=6.9 Hz, 1H), 3.89 (s, 3H), 5.16-5.24 (m, 1H), 5.47 (d, J=8.4 Hz, 1H), 6.60-6.67 (m, 1H), 6.94-7.02 (m, 1H), 7.10-7.16 (m, 3H), 7.36 (dd, J=1.5 Hz, 1.5 Hz, 1H), 7.64-7.72 (m, 3H); APCI-MS (m/z) 436.29 (M+H)+.

Example 20

(2S)—N-[(4S)-6-Chloro-3,4-dihydrospiro[chromene-2,1'-cyclobutan]-4-yl]-2-(6-methoxy-2-naphthyl)propanamide

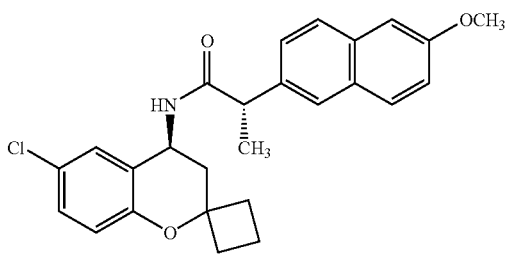 [SMILES: COc1ccc2cc([C@H](C)C(=O)N[C@H]3CC4(CCC4)Oc4ccc(Cl)cc43)ccc2c1]

The title compound was prepared from Intermediate 9 (200 mg, 0.769 mmol) and (2S)-2-(6-methoxy-2-naphthyl)propanoic acid (213 mg, 0.923 mmol) in presence of EDCI.HCl (221 mg, 1.153 mmol), HOBt (176 mg, 1.153 mmol) and triethylamine (321 µl, 2.307 mmol) in dichloromethane (10 ml) as described in Example 1 to give 103 mg of the product as a white solid; IR (KBr) 3267, 2932, 1638, 1477, 1263, 814 cm$^{-1}$; $^1$H NMR (300 MHz, DMSO-d$_6$) δ 1.65 (s, 3H), 1.68-1.74 (m, 2H), 1.84-1.90 (m, 1H), 2.13 (t, J=7.8 Hz, 3H), 2.27-2.37 (m, 2H), 3.74 (q, J=6.9 Hz, 1H), 3.89 (s, 3H), 5.22 (d, J=9.9 Hz, 1H), 5.50 (d, J=8.4 Hz, 1H), 6.60 (d, J=9.0 Hz, 1H), 6.70-6.76 (m, 1H), 6.94 (dd, J=1.8, 2.1 Hz, 1H), 7.10-7.16 (m, 2H), 7.39 (d, J=8.7 Hz, 1H), 7.67-7.76 (m, 3H); APCI-MS (m/z) 436.37 (M+H)+.

Example 21

N-(6-Chloro-3,4-dihydrospiro[chromene-2,1'-cyclobutan]-4-yl)-2-(1,2,3,4-tetrahydro naphthalen-1-yl)acetamide

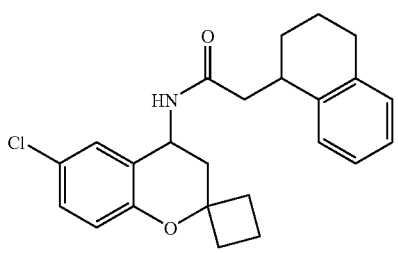 [SMILES: O=C(CC1CCCc2ccccc21)NC1CC2(CCC2)Oc2ccc(Cl)cc21]

The title compound was prepared from Intermediate 2 (212 mg, 0.951 mmol) and 5,6,7,8-tetrahydronaphthalen-1-ylacetic acid (150 mg, 0.791 mmol) in presence of EDCI.HCl (227 mg, 1.663 mmol), HOBt (121 mg, 0.791 mmol) and triethylamine (330 µl, 2.371 mmol) in dichloromethane (10 ml) as described in Example 1 to give 154 mg of the product as a white solid; IR (KBr) 3278, 2935, 1637, 1474, 1263, 818 cm$^{-1}$; $^1$H NMR (300 MHz, CDCl$_3$) δ 1.70-1.87 (m, 6H), 2.03-2.18 (m, 3H), 2.20-2.46 (m, 3H), 2.60-2.70 (m, 1H), 2.77 (br s, 2H), 3.47 (br s, 2H), 5.27 (q, J=9.3 Hz, 1H), 5.45 (d, J=7.8 Hz, 1H), 6.70 (d, J=8.7 Hz, 1H), 7.05-7.18 (m, 6H); ESI-MS (m/z) 394.76 (M–H)–.

Example 22

N-[(6-Chloro-3,4-dihydrospiro[chromene-2,1'-cyclobutan]-4-yl)]-2-(1,2,3,4-tetrahydro naphthalen-2-yl)acetamide

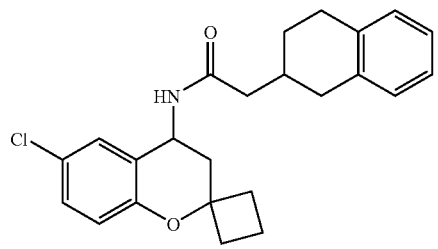 [SMILES: O=C(CC1CCc2ccccc2C1)NC1CC2(CCC2)Oc2ccc(Cl)cc21]

The title compound was prepared from Intermediate 2 (218 mg, 1.053 mmol) and 1,2,3,4-tetrahydronaphthalen-2-ylacetic acid (200 mg, 1.053 mmol) in presence of EDCI.HCl (302 mg, 1.585 mmol), HOBt (241 mg, 1.585 mmol) and triethylamine (439 µl, 3.165 mmol) in dichloromethane (10 ml) as described in Example 1 to give 40 mg of the product as a white solid; IR (KBr) 3250, 2931, 2343, 1635, 1474, 1232, 738 cm$^{-1}$; $^1$H NMR (300 MHz, CDCl$_3$) δ 1.67-1.82 (m, 3H), 1.83-1.95 (m, 2H), 2.21-2.29 (m, 3H), 2.30-2.39 (m, 4H), 2.48-2.59 (m, 1H), 2.85-2.96 (m, 3H), 5.32 (q, J=7.8 Hz, 1H), 5.59 (d, J=7.8 Hz, 1H), 6.73 (d, J=8.4 Hz, 1H), 6.73 (d, J=8.4 Hz, 1H), 7.08-7.14 (m, 6H); ESI-MS (m/z) 396.95 (M+H)+.

Example 23

2-(1,3-Benzodioxol-5-yl)-N-(6-chloro-3,4-dihydrospiro[chromene-2,1'-cyclobutan]-4-yl)acetamide

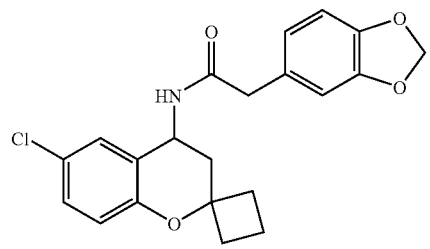 [SMILES: O=C(Cc1ccc2c(c1)OCO2)NC1CC2(CCC2)Oc2ccc(Cl)cc21]

The title compound was prepared from Intermediate 2 (200 mg, 0.892 mmol) and 1,3-benzodioxol-4-ylacetic acid (161 mg, 0.881 mmol) in presence of EDCI.HCl (256 mg, 1.343 mmol), HOBt (205 mg, 1.343 mmol) and triethylamine (366 µl, 2.683 mmol) in dichloromethane (10 ml) as described in Example 1 to give 125 mg of the product as a white solid; IR (KBr) 3059, 2941, 1634, 1488, 1243, 1045 cm$^{-1}$; $^1$H NMR (300 MHz, CDCl$_3$) δ 1.63-1.72 (m, 2H), 1.83-1.89 (m, 1H), 2.00-2.07 (m, 1H), 2.12-2.18 (m, 2H), 2.25-2.38 (m, 2H), 3.55 (d, J=2.4 Hz, 2H), 5.21 (q, J=9.9 Hz, 1H), 5.49 (d, J=8.1

Hz, 1H), 5.94 (s, 2H), 6.68-6.76 (m, 4H), 6.93 (s, 1H), 7.04 (dd, J=2.4, 6.3 Hz, 1H); ESI-MS (m/z) 384.16 (M−H)⁻.

Example 24

N-(6-Fluoro-3,4-dihydrospiro[chromene-2,1'-cyclobutan]-4-yl)-2-(5-fluoro-3-methyl-1H-indol-2-yl)acetamide

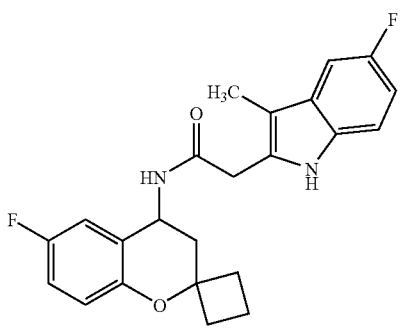 [SMILES: Cc1c(CC(=O)NC2CC3(CCC3)Oc3ccc(F)cc32)[nH]c2ccc(F)cc12]

The title compound was prepared from Intermediate 6 (200 mg, 0.963 mmol) and (5-fluoro-3-methyl-1H-indol-2-yl)acetic acid (200 mg, 0.963 mmol) in presence of EDCI.HCl (276 mg, 1.145 mmol), HOBt (221 mg, 1.145 mmol) and triethylamine (401 µl, 3.003 mmol) in dichloromethane (10 ml) as described in Example 1 to give 18 mg of the product as a white solid; ¹H NMR (300 MHz, DMSO-d₆) δ 1.52-1.74 (m, 4H), 1.88-1.95 (m, 2H), 2.08-2.25 (m, 2H), 2.40 (s, 3H), 3.70 (s, 2H), 5.23 (q, J=8.7 Hz, 1H), 5.68 (d, J=9.0 Hz, 1H), 6.61-6.66 (m, 2H), 6.72-6.89 (m, 2H), 7.07-7.18 (m, 2H), 8.01 (s, 1H); ESI-MS (m/z) 397.33 (M+H)⁺.

Example 25

N-(6-Chloro-3,4-dihydrospiro[chromene-2,1'-cyclobutan]-4-yl)-2-(5-methoxy-2-methyl-1H-indol-3-yl)acetamide

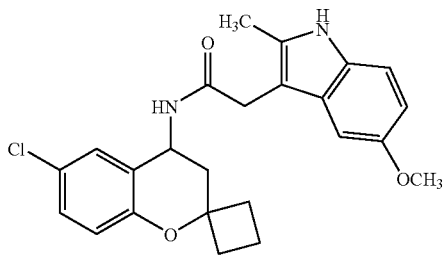 [SMILES: COc1ccc2[nH]c(C)c(CC(=O)NC3CC4(CCC4)Oc4ccc(Cl)cc43)c2c1]

The title compound was prepared from Intermediate 2 (200 mg, 0.896 mmol) and (5-methoxy-2-methyl-1H-indol-3-yl) acetic acid (195 mg, 0.896 mmol) in presence of EDCI.HCl (256 mg, 1.345 mmol), HOBt (205 mg, 1.345 mmol) and triethylamine (374 µl, 3.003 mmol) in dichloromethane (10 ml) as described in Example 1 to give 35 mg of the product as a white solid; IR (KBr) 3383, 2934, 2343, 1648, 1475, 1217, 820 cm⁻¹; ¹H NMR (300 MHz, CDCl₃) δ 1.50-1.65 (m, 5H), 1.83-1.95 (m, 3H), 2.40 (s, 3H), 3.73 (s, 3H), 3.82 (s, 2H), 5.23 (q, J=9.6 Hz, 1H), 5.76 (d, J=8.7 Hz, 1H), 6.62 (d, J=8.4 Hz, 1H), 6.77 (dd, J=2.4, 6.6 Hz, 1H), 6.82-6.89 (m, 2H), 6.98 (dd, J=2.1, 6.3 Hz, 1H), 7.14 (d, J=8.4 Hz, 1H), 7.84 (s, 1H); ESI-MS (m/z) 423.58 (M−H)⁻.

Example 26

2-(1,2-Benzisoxazol-3-yl)-N-[(4R)-(6-chloro-3,4-dihydrospiro[chromene-2,1'-cyclobutan]-4-yl)acetamide

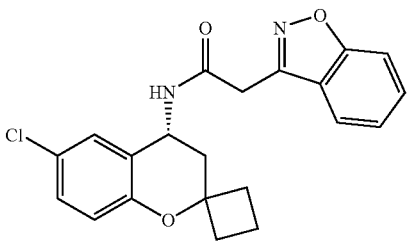 [SMILES: O=C(Cc1noc2ccccc12)N[C@@H]1CC2(CCC2)Oc2ccc(Cl)cc21]

The title compound was prepared from Intermediate 8 (200 mg, 0.763 mmol) and 1,2-benzisoxazol-3-ylacetic acid (148 mg, 0.839 mmol) in presence of EDCI.HCl (219 mg, 1.145 mmol), HOBt (175 mg, 1.145 mmol) and triethylamine (425 µl, 3.053 mmol) in dichloromethane (10 ml) as described in Example 1 to give 176 mg of the product as a white solid; IR (KBr) 3314, 2940, 1654, 1533, 1235, 749 cm⁻¹; ¹H NMR (300 MHz, CDCl₃) δ 1.61-1.68 (m, 1H), 1.77-1.87 (m, 2H), 2.03-2.14 (m, 3H), 2.29-2.38 (m, 2H), 4.06 (s, 2H), 5.24 (q, J=7.2 Hz, 1H), 6.34 (d, J=8.7 Hz, 1H), 6.68 (d, J=8.4 Hz, 1H), 6.92 (s, 1H), 7.02 (d, J=9.0 Hz, 1H), 7.28-7.38 (m, 1H), 7.57 (s, 2H), 7.80 (d, J=7.8 Hz, 1H); ESI-MS (m/z) 383.50 (M+H)⁺.

Example 27

2-(1,2-Benzisoxazol-3-yl)-N-[(4S)-(6-chloro-3,4-dihydrospiro[chromene-2,1'-cyclobutan]-4-yl)acetamide

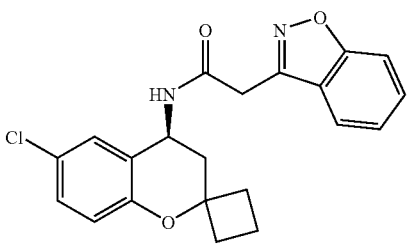 [SMILES: O=C(Cc1noc2ccccc12)N[C@H]1CC2(CCC2)Oc2ccc(Cl)cc21]

The title compound was prepared from Intermediate 9 (200 mg, 0.763 mmol) and 1,2-benzisoxazol-3-ylacetic acid (148 mg, 0.839 mmol) in presence of EDCI.HCl (219 mg, 1.145 mmol), HOBt (175 mg, 1.145 mmol) and triethylamine (425 µl, 3.053 mmol) in dichloromethane (10 ml) as described in Example 1 to give 176 mg of the product as a white solid; IR (KBr) 3314, 2940, 1654, 1533, 1235, 749 cm⁻¹; ¹H NMR (300 MHz, CDCl₃) δ 1.60-1.67 (m, 1H), 1.79-1.87 (m, 2H), 2.05-2.18 (m, 3H), 2.29-2.38 (m, 2H), 4.05 (s, 2H), 5.24 (q, J=7.2 Hz, 1H), 6.34 (d, J=8.7 Hz, 1H), 6.68 (d, J=8.4 Hz, 1H), 6.92 (s, 1H), 7.02 (d, J=9.0 Hz, 1H), 7.28-7.38 (m, 1H), 7.57 (s, 2H), 7.80 (d, J=7.8 Hz, 1H); ESI-MS (m/z) 383.50 (M+H)⁺.

Example 28

N-(6-Chloro-3,4-dihydrospiro[chromene-2,1'-cyclobutan]-4-yl)-3-(2-cyclopentyloxy phenyl)propanamide

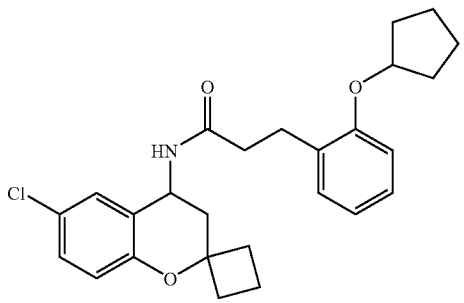 [SMILES: O=C(CCc1ccccc1OC1CCCC1)NC1CC2(CCC2)Oc2ccc(Cl)cc21]

The title compound was prepared from Intermediate 2 (200 mg, 0.779 mmol) and 3-[(2-cyclopentyloxyphenyl)propanoic acid (181 mg, 0.779 mmol) in presence of EDCI.HCl (222 mg, 1.152 mmol), HOBt (177 mg, 1.152 mmol) and triethylamine (427 µl, 3.116 mmol) in dichloromethane (10 ml) as described in Example 1 to give 150 mg of the product as a white solid; IR (KBr) 3316, 2952, 1651, 1488, 749 cm⁻¹; ¹H NMR (300 MHz, CDCl₃) δ 1.58-1.65 (m, 3H), 1.72-1.87 (m, 8H), 2.02-2.12 (m, 3H), 2.26-2.36 (m, 2H), 2.56 (t, J=6.9 Hz, 2H), 2.95 (t, J=7.5 Hz, 2H), 4.72 (br s, 1H), 5.15 (q, J=8.7 Hz, 1H), 5.59 (d, J=7.8 Hz, 1H), 6.69 (d, J=8.4 Hz, 1H), 6.80-6.88 (m, 3H), 7.04 (dd, J=2.4, 5.7 Hz, 1H), 7.14 (d, J=7.5 Hz, 2H); ESI-MS (m/z) 440.34 (M)⁺.

Example 29

N-[(4R)-6-chloro-3,4-dihydrospiro[chromene-2,1'-cyclobutan]-4-yl]-3-(3-cyclopentyloxy)phenyl propanamide

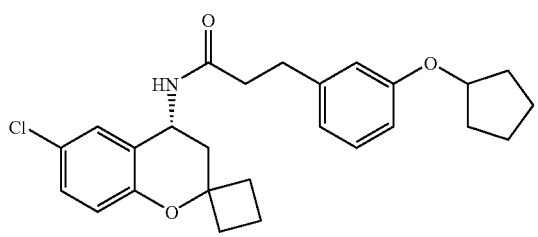 [SMILES: O=C(CCc1cccc(OC2CCCC2)c1)N[C@@H]1CC2(CCC2)Oc2ccc(Cl)cc21]

The title compound was prepared from Intermediate 8 (100 mg, 0.448 mmol) and 3-[(3-cyclopentyloxyphenyl)propanoic acid (105 mg, 0.448 mmol) in presence of EDCI.HCl (128 mg, 0.672 mmol), HOBt (102 mg, 0.672 mmol) and triethylamine (187 µl, 1.344 mmol) in dichloromethane (10 ml) as described in Example 1 to give 105 mg of the product as a white solid; IR (KBr) 3019, 2400, 2973, 1663, 1215, 761 cm⁻¹; ¹H NMR (300 MHz, CDCl₃) δ 1.64-1.70 (m, 4H), 1.80-1.88 (m, 7H), 2.00-2.08 (m, 1H), 2.15 (t, J=8.1 Hz, 2H), 2.25-2.32 (m, 2H), 2.55 (q, J=6.9 Hz, 2H), 2.97 (t, J=6.6 Hz, 2H), 4.72 (br s, 1H), 5.17 (q, J=4.2 Hz, 1H), 5.40 (d, J=7.8 Hz, 1H), 6.68-6.78 (m, 4H), 6.93 (s, 1H), 7.05 (d, J=6.6 Hz, 1H), 7.18 (t, J=7.8 Hz, 1H); ESI-MS (m/z) 440.54 (M+H)⁺.

Example 30

N-[(4S)-6-chloro-3,4-dihydrospiro[chromene-2,1'-cyclobutan]-4-yl]-3-(3-cyclopentyloxy)phenylpropanamide

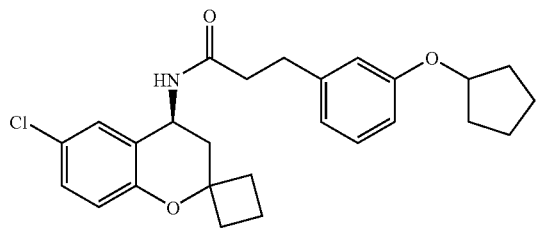 [SMILES: O=C(CCc1cccc(OC2CCCC2)c1)N[C@H]1CC2(CCC2)Oc2ccc(Cl)cc21]

The title compound was prepared from Intermediate 9 (104 mg, 0.444 mmol) and 3-[(3-cyclopentyloxyphenyl)propanoic acid (100 mg, 0.444 mmol) in presence of EDCI.HCl (128 mg, 0.672 mmol), HOBt (102 mg, 0.672 mmol) and triethylamine (186 µl, 1.344 mmol) in dichloromethane (10 ml) as described in Example 1 to give 100 mg of the product as a white solid; IR (KBr) 3293, 2934, 1694, 1532, 1216, 756 cm⁻¹; ¹H NMR (300 MHz, CDCl₃) δ 1.62-1.70 (m, 6H), 1.78-1.85 (m, 5H), 2.04-2.16 (m, 3H), 2.28-2.32 (m, 2H), 2.54 (d, J=6.9 Hz, 2H), 2.90-2.99 (m, 2H), 4.72 (br s, 1H), 5.18 (q, J=5.7 Hz, 1H), 5.37 (d, J=7.5 Hz, 1H), 6.71-6.77 (m, 3H), 6.92 (s, 1H), 7.04 (d, J=7.8 Hz, 1H), 7.10-7.18 (m, 2H); ESI-MS (m/z) 440.55 (M+H)⁺.

Example 31

N-1(4R)-(8-Chloro-3,4-dihydrospiro[chromene-2,1'-cyclobutan]-4-yl)-3-(2-cyclopentyloxy)phenyl propanamide

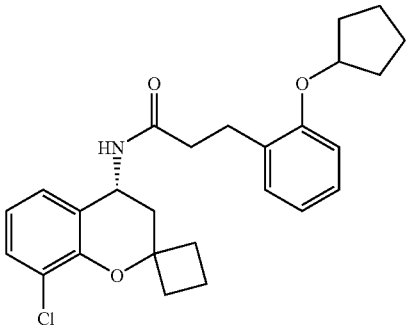 [SMILES: O=C(CCc1ccccc1OC1CCCC1)N[C@@H]1CC2(CCC2)Oc2c(Cl)cccc21]

The title compound was prepared from Intermediate 3 (100 mg, 0.448 mmol) and 3-[(2-cyclopentyloxyphenyl)propanoic acid (125 mg, 0.536 mmol) in presence of EDCI.HCl (128 mg, 0.672 mmol), HOBt (102 mg, 0.672 mmol) and triethylamine (186 µl, 1.344 mmol) in dichloromethane (10 ml) as described in Example 1 to give 142 mg of the product as a white solid; IR (KBr) 3321, 2950, 1646, 1453, 1239, 989 cm⁻¹; ¹H NMR (300 MHz, CDCl₃) δ 1.68-1.75 (m, 11H), 2.05-2.17 (m, 3H), 2.36-2.46 (m, 2H), 2.56 (t, J=7.2 Hz, 2H), 2.96 (t, J=6.6 Hz, 2H), 4.72 (br s, 1H), 5.22 (q, J=8.7 Hz, 1H), 5.55 (d, J=8.7 Hz, 1H), 6.69 (s, 2H), 6.78-6.88 (m, 2H), 7.14-7.19 (m, 3H); ESI-MS (m/z) 440.34 (M+H)+.

Example 32

N-[(4S)-8-chloro-3,4-dihydrospiro[chromene-2,1'-cyclobutan-4-yl]-3-[2-(cyclopentyloxyphenyl)propanamide

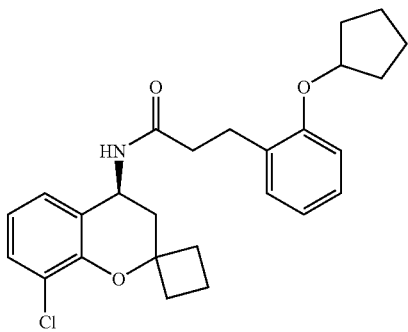 [SMILES: O=C(CCc1ccccc1OC1CCCC1)N[C@H]1CC2(CCC2)Oc2c(Cl)cccc21]

The title compound was prepared from Intermediate 4 (100 mg, 0.448 mmol) and 3-[(2-cyclopentyloxyphenyl)propanoic acid (115 mg, 0.494 mmol) in presence of EDCI.HCl (129 mg, 0.674 mmol), HOBt (103 mg, 0.674 mmol) and triethylamine (187 μl, 1.348 mmol) in dichloromethane (10 ml) as described in Example 1 to give 211 mg of the product as a white solid; IR (KBr) 3321, 2950, 1646, 1453, 1239, 989 cm$^{-1}$; $^1$H NMR (300 MHz, CDCl$_3$) δ 1.68-1.75 (m, 11H), 2.05-2.17 (m, 3H), 2.36-2.46 (m, 2H), 2.56 (t, J=7.2 Hz, 2H), 2.96 (t, J=6.6 Hz, 2H), 4.72 (br s, 1H), 5.22 (q, J=8.7 Hz, 1H), 5.55 (d, J=8.7 Hz, 1H), 6.69 (s, 2H), 6.78-6.88 (m, 2H), 7.14-7.19 (m, 3H); ESI-MS (m/z) 440.34 (M+H)+.

Example 33

7-Benzyloxy-N-(3,4-dihydrospiro[chromene-2,1'-cyclobutan-4-yl)-3-(2-cyclopentylxoyphenyl)propanamide

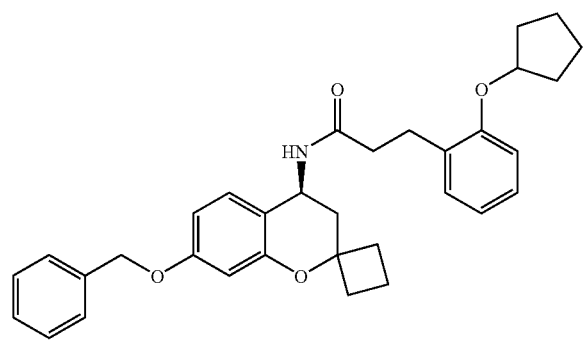 [SMILES: O=C(CCc1ccccc1OC1CCCC1)N[C@H]1CC2(CCC2)Oc2cc(OCc3ccccc3)ccc21]

The title compound was prepared from Intermediate 12 (200 mg, 0.603 mmol) and 3-(2-cyclopentyloxyphenyl)propanoic acid (169 mg, 0.723 mmol) in presence of EDCI.HCl (173 mg, 0.904 mmol), HOBt (138 mg, 0.904 mmol) and triethylamine (335 μl, 2.413 mmol) in dichloromethane (10 ml) as described in Example 1 to give 163 mg of the product as a white solid; IR (KBr) 3324, 2954, 1647, 1239, 1171, 745 cm$^{-1}$; $^1$H NMR (300 MHz, CDCl$_3$) δ 1.66-1.79 (m, 11H), 2.04-2.12 (m, 4H), 2.25-2.32 (m, 2H), 2.52 (t, J=7.2 Hz, 2H), 2.94 (t, J=7.5 Hz, 2H), 4.69 (br s, 1H), 4.98 (s, 2H), 5.17 (q, J=5.7 Hz, 1H), 5.48 (d, J=9.3 Hz, 1H), 6.39-6.46 (m, 2H), 6.67 (d, J=8.7 Hz, 1H), 6.75-6.85 (m, 2H), 7.10-7.16 (m, 2H), 7.29-7.37 (m, 4H); ESI-MS (m/z) 510.34 (M+H)+.

Example 34

N-(6-Chloro-3,4-dihydrospiro[chromene-2,1'-cyclobutan]-4-yl)-3-{2-[(isopropyl sulfonyl)amino]phenyl}propanamide

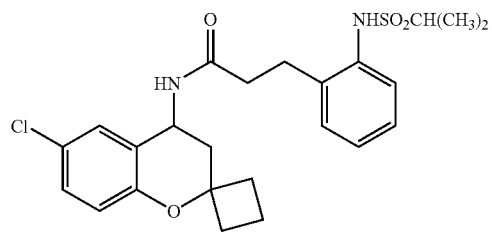

Step 1: (2E)-N-(6-chloro-3,4-dihydrospiro[chromene-2,1'-cyclobutan]-4-yl)-3-{2-[(isopropylsulfonyl)amino]phenyl}acrylamide This compound was prepared from Intermediate 2 (150 mg, 0.576 mmol) and (2E)-3-{2-[(isopropylsulfonyl)amino]phenyl}acrylic acid (186 mg, 0.692 mmol) in presence of EDCI.HCl (165 mg, 0.865 mmol), HOBt (132 mg, 0.865 mmol) and triethylamine (240 μl, 1.732 mmol) in dichloromethane (10 ml) as described in Example 1 to give 125 mg of the product as a white solid; $^1$H NMR (300 MHz, CDCl$_3$) δ 0.82-0.90 (m, 2H), 1.20-1.26 (m, 4H), 1.74-1.85 (m, 3H), 2.10-2.20 (m, 3H), 2.46-2.52 (m, 2H), 3.29 (t, J=6.3 Hz, 1H), 3.34-3.40 (m, 1H), 6.00-6.06 (m, 1H), 6.40 (d, J=15.6 Hz, 1H), 6.72 ((d, J=8.4 Hz, 1H), 7.05-7.18 (m, 3H), 7.33 (d, J=7.8 Hz, 2H), 7.49 (d, J=7.5 Hz, 1H), 7.57 (d, J=7.8 Hz, 1H), 8.08 (d, J=15.9 Hz, 1H).

Step 2: N-(6-Chloro-3,4-dihydrospiro[chromene-2,1'-cyclobutan]-4-yl)-3-{2-[(isopropyl-sulfonyl)amino]phenyl}propanamide Step 1 Intermediate (110 mg, 0.232 mmol) was reduced using 5% Pd/C (30 mg) in ethyl acetate at 30 psi pressure for 1.5 h in Paar apparatus. The reaction mixture was filtered through celite and the filtrate was concentrated under reduced pressure to get a crude compound which was purified by silica gel column chromatography using 13% acetone in petroleum ether to give 51 mg of the product as a white solid; IR (Neat) 3343, 2936, 1651, 1537, 1475, 1320, 1102, 756 cm$^{-1}$; $^1$H NMR (300 MHz, CDCl$_3$) δ 1.40-1.50 (m, 5H), 1.56-1.62 (m, 2H), 1.65-1.71 (m, 2H), 1.85-1.91 (m, 1H), 2.10-2.20 (m, 3H), 2.27-2.33 (m, 2H), 2.60-2.68 (m, 2H), 3.04-3.12 (m, 2H), 3.32-3.38 (m, 1H), 5.15 (br s, 1H), 5.60 (br s, 1H), 6.66-6.72 (m, 2H), 7.03 (d, J=6.9 Hz, 1H), 7.12-7.20 (m, 2H), 7.47 (d, J=7.8 Hz, 1H), 8.22 (s, 1H); ESI-MS (m/z) 477.95 (M)+.

Example 35

N-(6-Chloro-3,4-dihydrospiro[chromene-2,1'-cyclobutan]-4-yl)-3-(2-pyridin-2-ylphenyl) propanamide

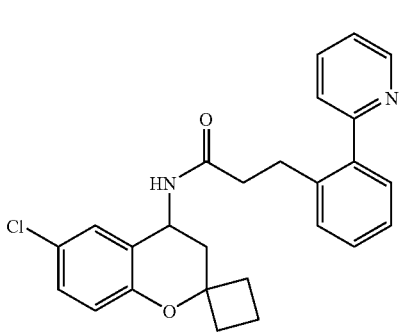 [SMILES: O=C(CCc1ccccc1-c1ccccn1)NC1CC2(CCC2)Oc2ccc(Cl)cc21]

Step 1: (2E)-N-(6-chloro-3,4-dihydrospiro[chromene-2,1'-cyclobutan]-4-yl)-3-(2-pyridin-2-ylphenyl)acrylamide This compound was prepared from Intermediate 2 (300 mg, 1.153 mmol) and (2E)-3-(2-pyridin-2-ylphenyl)acrylic acid (260 mg, 1.153 mmol) in presence of EDCI.HCl (332 mg, 1.730 mmol), HOBt (177 mg, 1.153 mmol) and triethylamine (402 µl, 2.884 mmol) in dichloromethane (10 ml) as described in Example 1 to give 400 mg of the product as a white solid; IR (Neat) 3228, 2935, 1651, 1540, 1475, 1264, 759 cm⁻¹; ¹H NMR (300 MHz, CDCl₃) δ 1.80-1.90 (m, 2H), 2.08-2.20 (m, 4H), 2.35-2.49 (m, 2H), 3.46 (q, J=7.2 Hz, 1H), 5.34 (q, J=9.3 Hz, 1H), 5.84 (d, J=8.7 Hz, 1H), 6.37 (d, J=15.0 Hz, 1H), 6.73 (d, J=8.1 Hz, 1H), 7.08 (d, J=8.4 Hz, 1H), 7.14 (s, 1H), 7.33-7.43 (m, 4H), 7.61-7.70 (m, 3H), 8.55-8.61 (m, 2H); ESI-MS (m/z) 431.24 (M+H)+.

Step 2: N-(6-Chloro-3,4-dihydrospiro[chromene-2,1'-cyclobutan]-4-yl)-3-(2-pyridin-2-ylphenyl)propanamide Step 1 intermediate (300 mg, 0.696) was reduced by using Pd/C (50 mg) in methanol at 40 psi pressure for 3 h in Paar apparatus. The reaction mixture was filtered through celite and the filtrate was concentrated under reduced pressure to get a crude compound which was purified by silica gel column chromatography using 25% ethyl acetate in petroleum ether to give 231 mg of the product as a white solid; IR (KBr) 3270, 2972, 1674, 1635, 1449, 775 cm⁻¹; ¹H NMR (300 MHz, CDCl₃) δ 1.65-1.71 (m, 2H), 1.81-1.89 (m, 1H), 1.92-2.04 (m, 3H), 2.07-2.14 (m, 4H), 3.01 (q, J=4.2 Hz, 2H), 5.13 (q, J=9.3 Hz, 1H), 5.39 (d, J=7.8 Hz, 1H), 6.70 (d, J=8.7 Hz, 1H), 6.85 (s, 1H), 7.05 (d, J=9.0 Hz, 1H), 7.20 (d, J=7.2 Hz, 1H), 7.30-7.37 (m, 4H), 7.67 (d, J=7.8 Hz, 1H), 8.55 (s, 2H); ESI-MS (m/z) 433.48 (M+H)+.

Example 36

N-(6,8-Dichloro-3,4-dihydrospiro[chromene-2,1'-cyclobutan]-4-yl)-3-(2-pyridin-3-yl-phenyl)propanamide

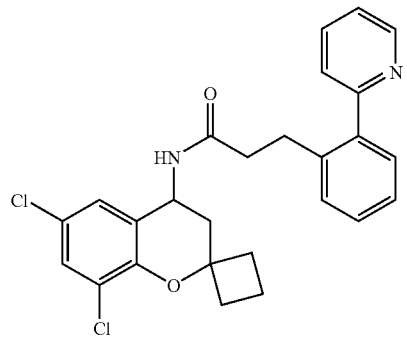 [SMILES: O=C(CCc1ccccc1-c1ccccn1)NC1CC2(CCC2)Oc2c(Cl)cc(Cl)cc21]

The title compound was prepared from Intermediate 13 (100 mg, 0.340 mmol) and 3-(2-pyridin-2-ylphenyl)propanoic acid (85 mg, 0.374 mmol) in presence of EDCI.HCl (97 mg, 0.509 mmol), HOBt (78 mg, 0.511 mmol) and triethylamine (142 µl, 2.884 mmol) in dichloromethane (5 ml) as described in Example 1 to give 59 mg of the product as a white solid; ¹H NMR (300 MHz, CDCl₃) δ 1.71-1.79 (m, 4H), 1.98-2.07 (m, 2H), 2.22-2.39 (m, 4H), 2.76-2.84 (m, 2H), 4.90-5.05 (m, 1H), 6.83 (br s, 1H), 7.29-7.49 (m, 5H), 7.78 (d, J=7.2 Hz, 1H), 8.28 (s, 2H), 8.50-8.58 (m, 2H).

Example 37

N-(3,4-Dihydro spiro[chromene-2,1'-cyclobutan]-4-yl)-3-(2-cyclopentyloxy-3-methoxy)phenylpropanamide

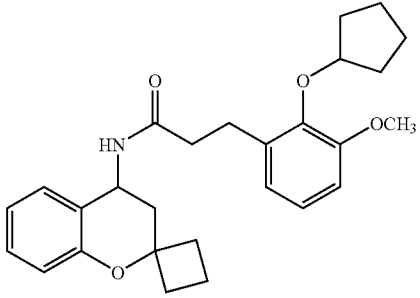 [SMILES: COc1cccc(CCC(=O)NC2CC3(CCC3)Oc3ccccc32)c1OC1CCCC1]

The title compound was prepared from Intermediate 5 (113 mg, 0.604 mmol) and 3-[2-(cyclopentyloxy-3-methoxy)phenyl]propanoic acid (150 mg, 0.604 mmol) in presence of EDCI.HCl (172 mg, 0.906 mmol), HOBt (137 mg, 0.906 mmol) and triethylamine (249 µl, 1.835 mmol) in dichloromethane (10 ml) as described in Example 1 to give 125 mg of the product as a white solid; IR (KBr) 3282, 2949, 1640, 1454, 1232, 753 cm⁻¹; ¹H NMR (300 MHz, CDCl₃) δ 1.68-1.78 (m, 11H), 2.05-2.15 (m, 3H), 2.28-2.39 (m, 2H), 2.55 (t, J=6.6 Hz, 2H), 2.98 (t, J=6.6 Hz, 2H), 3.79 (s, 3H), 4.85 (br s, 1H), 5.19 (q, J=6.9 Hz, 1H), 5.64 (d, J=7.8 Hz, 1H), 6.73-6.80 (m, 5H), 6.95 (t, J=7.8 Hz, 1H), 7.08 (t, J=7.5 Hz, 1H); ESI-MS (m/z) 433.30 (M−H)⁻.

Example 38

N-(6-Chloro-3,4-dihydrospiro[chromene-2,1'-cyclobutan]-4-yl)-3-(2,3-dimethoxy)-phenylpropanamide

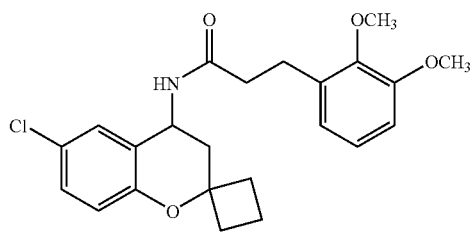 [SMILES: COc1cccc(CCC(=O)NC2CC3(CCC3)Oc3ccc(Cl)cc32)c1OC]

The title compound was prepared from Intermediate 2 (200 mg, 0.898 mmol) and 3-(2,3-dimethoxyphenyl)propanoic acid (207 mg, 0.988 mmol) in presence of EDCI.HCl (258 mg, 1.348 mmol), HOBt (206 mg, 1.348 mmol) and triethylamine (372 μl, 2.695 mmol) in dichloromethane (10 ml) as described in Example 1 to give 246 mg of the product as a white solid; IR (KBr) 3051, 2942, 1642, 1475, 1263, 750 cm⁻¹; ¹H NMR (300 MHz, CDCl₃) δ 1.62-1.69 (m, 2H), 1.82-1.89 (m, 1H), 2.09-2.17 (m, 3H), 2.25-2.36 (m, 2H), 2.57 (t, J=6.9 Hz, 2H), 3.00 (t, J=6.9 Hz, 2H), 3.81 (s, 6H), 5.16 (q, J=8.7 Hz, 1H), 5.62 (d, J=7.8 Hz, 1H), 6.68 (d, J=9.0 Hz, 1H), 6.79-6.86 (m, 3H), 7.00 (q, J=7.2 Hz, 2H); ESI-MS (m/z) 416.16 (M+H)⁺.

Example 39

N-(6-Chloro-3,4-dihydrospiro[chromene-2,1'-cyclobutan]-4-yl)-3-(2-isopropoxy-3-methoxy)phenyl-propanamide

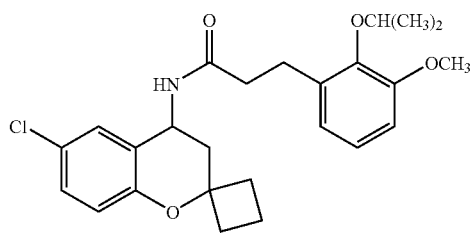

The title compound was prepared from Intermediate 2 (200 mg, 0.898 mmol) and 3-(2-isopropoxy-3-methoxyphenyl)propanoic acid (235 mg, 0.988 mmol) in presence of EDCI.HCl (258 mg, 1.348 mmol), HOBt (206 mg, 1.348 mmol) and triethylamine (372 μl, 2.695 mmol) in dichloromethane (10 ml) as described in Example 1 to give 157 mg of the product as a white solid; ¹H NMR (300 MHz, CDCl₃) δ 1.23 (s, 6H), 1.87 (br s, 2H), 2.13-2.26 (m, 6H), 2.58 (br s, 2H), 3.01 (br s, 2H), 3.79 (s, 3H), 4.49 (br s, 1H), 5.15 (br s, 1H), 5.84 (br s, 1H), 6.67 (d, J=7.8 Hz, 1H), 6.79-6.86 (m, 3H), 6.97-7.04 (m, 2H).

Example 40

N-(6-Chloro-3,4-dihydrospiro[chromene-2,1'-cyclobutan]-4-yl)-3-(3-chloro-4-methoxy)phenylpropanamide

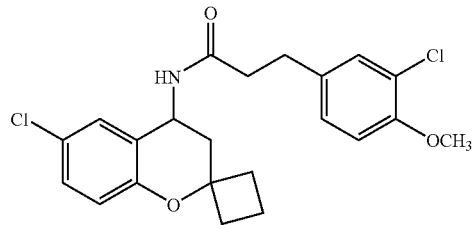 [SMILES: COc1ccc(CCC(=O)NC2CC3(CCC3)Oc3ccc(Cl)cc32)cc1Cl]

The title compound was prepared from Intermediate 2 (200 mg, 0.763 mmol) and 3-(3-chloro-4-methoxyphenyl)propanoic acid (198 mg, 0.923 mmol) in presence of EDCI.HCl (221 mg, 1.153 mmol), HOBt (175 mg, 1.153 mmol) and triethylamine (321 μl, 2.307 mmol) in dichloromethane (10 ml) as described in Example 1 to give 136 mg of the product as a white solid; IR (KBr) 3272, 2972, 1645, 1484, 1226, 794 cm⁻¹; ¹H NMR (300 MHz, CDCl₃) δ 1.60-1.73 (m, 1H), 1.85-1.91 (m, 1H), 2.03-2.17 (m, 3H), 2.22-2.32 (m, 2H), 2.44-2.56 (m, 2H), 2.91-2.96 (m, 2H), 3.86 (s, 3H), 5.22 (q, J=8.4 Hz, 1H), 5.49 (d, J=8.4 Hz, 1H), 6.69 (d, J=8.7 Hz, 1H), 6.83-6.90 (m, 2H), 7.05 (t, J=7.8 Hz, 2H), 7.21 (s, 1H); ESI-MS (m/z) 456.38 (M+H)⁺.

Example 41

N-(6-Chloro-3,4-dihydrospiro[chromene-2,1'-cyclobutan]-4-yl)-3-(2-cyclopropylmethoxy-3-methoxy)phenylpropanamide

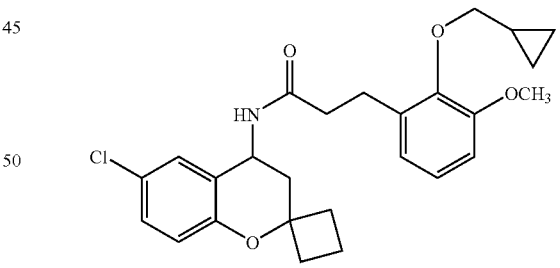

The title compound was prepared from Intermediate 2 (200 mg, 0.769 mmol) and 3-(2-cyclopropylmethoxy-3-methoxyphenyl)propanoic acid (232 mg, 0.923 mmol) in presence of EDCI.HCl (221 mg, 1.153 mmol), HOBt (176 mg, 1.153 mmol) and triethylamine (321 μl, 2.307 mmol) in dichloromethane (10 ml) as described in Example 1 to give 134 mg of the product as a white solid; IR (KBr) 3262, 2938, 1641, 1476, 1263, 1082, 820 cm⁻¹; ¹H NMR (300 MHz, CDCl₃) δ 0.26 (d, J=4.8 Hz, 2H), 0.51-0.57 (m, 2H), 1.16-1.23 (m, 1H), 1.63-1.71 (m, 4H), 1.85-1.89 (m, 1H), 2.01-2.16 (m, 1H), 2.23-2.36 (m, 2H), 2.61 (t, J=7.2 Hz, 2H), 3.03 (t, J=7.5 Hz, 2H), 3.76 (s, 3H), 3.80 (s, 2H), 5.15 (q, J=12.0 Hz, 1H), 5.77

(d, J=8.7 Hz, 1H), 6.67 (d, J=8.7 Hz, 1H), 6.77-6.83 (m, 3H), 6.95-7.04 (m, 2H); ESI-MS (m/z) 456.38 (M+H)⁺.

Example 42

N-[(4R)-6-Chloro-3,4-dihydrospiro[chromene-2,1'-cyclobutan]-4-yl)]-3-(2-cyclopentyl-oxy-3-methoxy)phenylpropanamide

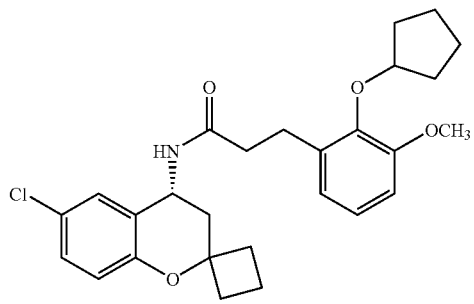 [SMILES: COc1cccc(CCC(=O)N[C@@H]2CC3(CCC3)Oc3ccc(Cl)cc32)c1OC1CCCC1]

The title compound was prepared from Intermediate 8 (150 mg, 0.674 mmol) and 3-(2-cyclopentyloxy-3-methoxyphenyl)propanoic acid (213 mg, 0.674 mmol) in presence of EDCI.HCl (193 mg, 1.011 mmol), HOBt (154 mg, 1.011 mmol) and triethylamine (281 µl, 2.021 mmol) in dichloromethane (10 ml) as described in Example 1 to give 167 mg of the product as a white solid; IR (KBr) 3274, 2956, 1643, 1475, 1263, 1079 cm⁻¹; ¹H NMR (300 MHz, CDCl₃) δ 1.71-1.78 (m, 8H), 2.04-2.16 (m, 6H), 2.22-2.39 (m, 2H), 2.54-2.59 (m, 2H), 2.97 (t, J=6.6 Hz, 2H), 3.79 (s, 3H), 4.85 (br s, 1H), 5.14 (q, J=8.7 Hz, 1H), 5.78 (d, J=8.4 Hz, 1H), 6.67 (d, J=8.4 Hz, 1H), 6.77-6.84 (m, 3H), 6.94-7.00 (m, 2H); ESI-MS (m/z) 392.35 (M+H)⁺.

Example 43

N-[(4S)-6-Chloro-3,4-dihydrospiro[chromene-2,1'-cyclobutan]-4-yl)]-3-(2-cyclopentyl-oxy-3-methoxy)phenylpropanamide

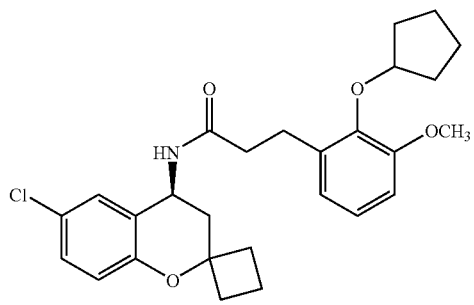 [SMILES: COc1cccc(CCC(=O)N[C@H]2CC3(CCC3)Oc3ccc(Cl)cc32)c1OC1CCCC1]

The title compound was prepared from Intermediate 9 (150 mg, 0.674 mmol) and 3-(2-cyclopentyloxy-3-methoxyphenyl)propanoic acid (195 mg, 0.741 mmol) in presence of EDCI.HCl (193 mg, 1.011 mmol), HOBt (154 mg, 1.011 mmol) and triethylamine (281 µl, 2.022 mmol) in dichloromethane (10 ml) as described in Example 1 to give 113 mg of the product as a white solid; IR (KBr) 3316, 2955, 1650, 1477, 1264, 1078 cm⁻¹; ¹H NMR (300 MHz, CDCl₃) δ 1.68-1.72 (m, 8H), 1.74-1.82 (m, 6H), 2.22-2.39 (m, 2H), 2.54-2.59 (m, 2H), 2.97 (t, J=7.5 Hz, 2H), 3.80 (s, 3H), 4.85 (br s, 1H), 5.14 (q, J=6.3 Hz, 1H), 5.76 (d, J=8.4 Hz, 1H), 6.67 (d, J=8.4 Hz, 1H), 6.77-6.84 (m, 3H), 6.94-7.00 (m, 2H); ESI-MS (m/z) 470.42 (M)⁺.

Example 44

N-(6-Chloro-3,4-dihydrospiro[chromene-2,1'-cyclobutan]-4-yl)-3-(2-cyclopentyloxy-3-ethoxy)phenylpropanamide

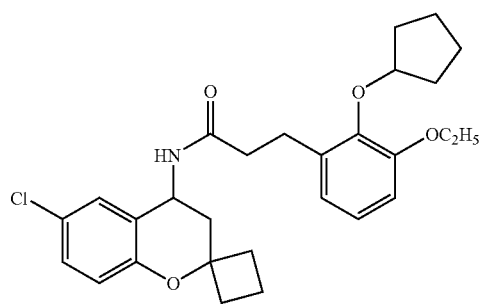 [SMILES: CCOc1cccc(CCC(=O)NC2CC3(CCC3)Oc3ccc(Cl)cc32)c1OC1CCCC1]

The title compound was prepared from Intermediate 2 (150 mg, 0.571 mmol) and 3-(2-cyclopentyloxy-3-ethoxyphenyl)propanoic acid (177 mg, 0.631 mmol) in presence of EDCI.HCl (166 mg, 0.863 mmol), HOBt (133 mg, 0.863 mmol) and triethylamine (241 µl, 1.734 mmol) in dichloromethane (10 ml) as described in Example 1 to give 180 mg of the product as a white solid; IR (KBr) 3327, 2953, 1646, 1476, 1263, 1071 cm⁻¹; ¹H NMR (300 MHz, CDCl₃) δ 1.39-1.46 (m, 4H), 1.64-1.81 (m, 10H), 2.06-2.16 (m, 3H), 2.22-2.32 (m, 2H), 2.57 (t, J=7.2 Hz, 2H), 2.97 (t, J=7.5 Hz, 2H), 3.99 (q, J=6.3 Hz, 2H), 4.84 (br s, 1H), 5.14 (q, J=5.4 Hz, 1H), 5.76 (d, J=9.3 Hz, 1H), 6.66-6.91 (m, 4H), 7.01 (d, J=8.4 Hz, 2H); ESI-MS (m/z) 484.28 (M)⁺.

Example 45

N-(7-Chloro-3,4-dihydrospiro[chromene-2,1'-cyclobutan]-4-yl)-3-(2-cyclopentyloxy-3-methoxy)phenylpropanamide

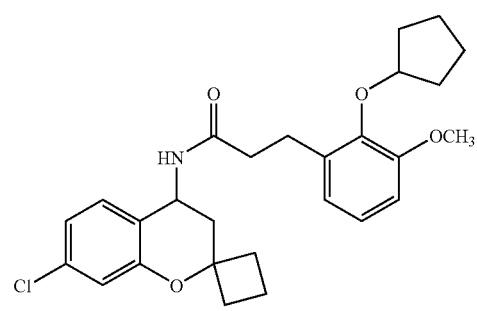 [SMILES: COc1cccc(CCC(=O)NC2CC3(CCC3)Oc3cc(Cl)ccc32)c1OC1CCCC1]

The title compound was prepared from Intermediate 10 (200 mg, 0.769 mmol) and 3-(2-cyclopentyloxy-3-methoxyphenyl))propanoic acid (243 mg, 0.923 mmol) in presence of EDCI.HCl (221 mg, 1.543 mmol), HOBt (176 mg, 1.543 mmol) and triethylamine (321 µl, 2.307 mmol) in dichloromethane (10 ml) as described in Example 1 to give 121 mg of the product as a white solid; IR (KBr) 3263, 2938, 1641, 1480, 1270, 1081, 966 cm$^{-1}$; $^1$H NMR (300 MHz, CDCl$_3$) δ 1.59-1.77 (m, 10H), 2.13-2.27 (m, 5H), 2.57 (br s, 2H), 2.97 (br s, 2H), 3.47 (s, 1H), 3.79 (s, 3H), 4.85 (br s, 1H), 5.12-5.19 (m, 1H), 5.69-5.77 (m, 1H), 6.60-6.66 (m, 2H), 6.74-6.79 (m, 3H), 6.89-6.95 (m, 1H); ESI-MS (m/z) 470.23 (M)$^+$.

Example 46

N-(8-Chloro-3,4-dihydrospiro[chromene-2,1'-cyclobutan]-4-yl)-3-(2-ethoxy-3-methoxy)phenylpropanamide

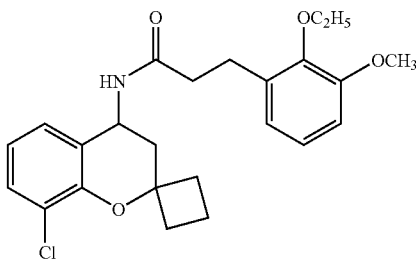 [SMILES: CCOc1c(CCC(=O)NC2CC3(CCC3)Oc3c(Cl)cccc32)cccc1OC]

The title compound was prepared from Intermediate 1 (200 mg, 0.893 mmol) and 3-(2-ethoxy-3-methoxyphenyl)propanoic acid (240 mg, 1.074 mmol) in presence of EDCI.HCl (257 mg, 1.346 mmol), HOBt (205 mg, 1.346 mmol) and triethylamine (497 μl, 3.563 mmol) in dichloromethane (10 ml) as described in Example 1 to give 132 mg of the product as a white solid; IR (KBr) 3263, 2936, 1649, 1451, 1243, 749 cm$^{-1}$; $^1$H NMR (300 MHz, CDCl$_3$) δ 1.33 (t, J=6.9 Hz, 3H), 1.63-1.74 (m, 2H), 1.85-1.91 (m, 1H), 2.03-2.17 (m, 3H), 2.22-2.32 (m, 2H), 2.40-2.50 (m, 2H), 3.00 (t, J=6.6 Hz, 2H), 3.80 (s, 3H), 4.00 (q, J=6.9 Hz, 2H), 5.21 (q, J=8.7 Hz, 1H), 5.65 (d, J=8.1 Hz, 1H), 6.63-6.70 (m, 2H), 6.77-6.84 (m, 2H), 6.88-6.97 (m, 1H), 6.99-7.17 (m, 1H); ESI-MS (m/z) 430.31 (M+H)$^+$.

Example 47

N-[(4R)-8-Chloro-3,4-dihydrospiro[chromene-2,1'-cyclobutan]-4-yl)]-3-(2-cyclopentyl-oxy-3-methoxy)phenylpropanamide

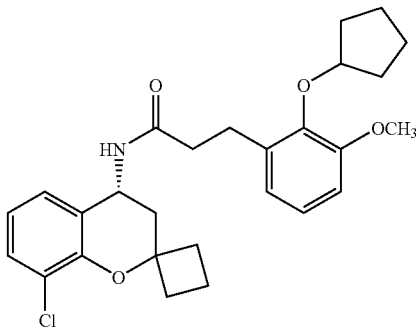 [SMILES: COc1cccc(CCC(=O)N[C@@H]2CC3(CCC3)Oc3c(Cl)cccc32)c1OC1CCCC1]

The title compound was prepared from Intermediate 3 (150 mg, 0.674 mmol) and 3-(2-cyclopentyloxy-3-methoxyphenyl))propanoic acid (213 mg, 0.824 mmol) in presence of EDCI.HCl (193 mg, 1.511 mmol), HOBt (154 mg, 1.511 mmol) and triethylamine (279 μl, 2.001 mmol) in THF (10 ml) as described in Example 1 to give 207 mg of the product as a white solid; IR (KBr) 3247, 2960, 1634, 1450, 1276, 1084, 746 cm$^{-1}$; $^1$H NMR (300 MHz, CDCl$_3$) δ 1.22-1.27 (m, 1H), 1.68-1.91 (m, 9H), 2.08-2.31 (m, 4H), 2.40-2.48 (m, 2H), 2.57 (t, J=6.9 Hz, 2H), 2.95 (t, J=6.9 Hz, 2H), 3.79 (s, 3H), 4.85 (br s, 1H), 5.20-5.30 (m, 1H), 5.72 (d, J=8.1 Hz, 1H), 6.62-6.70 (m, 2H), 6.78-6.85 (m, 2H), 6.95 (t, J=7.8 Hz, 1H), 7.16 (d, J=6.3 Hz, 1H); ESI-MS (m/z) 470.58 (M)$^+$.

Example 48

N-[(4S)-(8-Chloro-3,4-dihydrospiro[chromene-2,1'-cyclobutan]-4-yl)-3-(2-cyclopentyl oxy-3-methoxy)phenylpropanamide

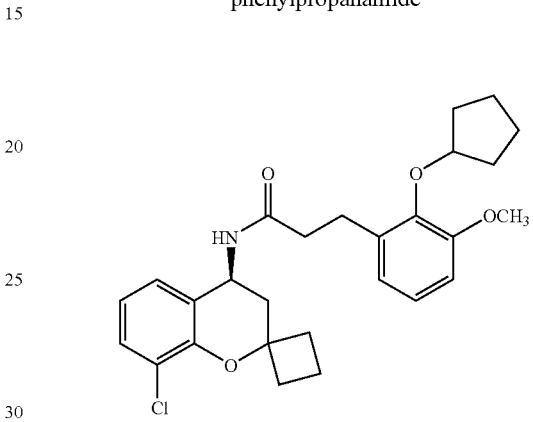

The title compound was prepared from Intermediate 4 (150 mg, 0.676 mmol) and 3-(2-cyclopentyloxy-3-methoxyphenyl))propanoic acid (212 mg, 0.892 mmol) in presence of EDCI.HCl (193 mg, 1.013 mmol), HOBt (154 mg, 1.013 mmol) and triethylamine (203 μl, 2.107 mmol) in dichloromethane (10 ml) as described in Example 1 to give 141 mg of the product as a white solid; $^1$H NMR (300 MHz, CDCl$_3$) δ 1.22-1.27 (m, 1H), 1.68-1.91 (m, 9H), 2.08-2.31 (m, 4H), 2.40-2.48 (m, 2H), 2.57 (t, J=6.9 Hz, 2H), 2.95 (t, J=6.9 Hz, 2H), 3.79 (s, 3H), 4.85 (br s, 1H), 5.20-5.30 (m, 1H), 5.72 (d, J=8.1 Hz, 1H), 6.62-6.70 (m, 2H), 6.78-6.85 (m, 2H), 6.95 (t, J=7.8 Hz, 1H), 7.16 (d, J=6.3 Hz, 1H); ESI-MS (m/z) 470.68 (M)$^+$.

Example 49

N-(6-Chloro-7-methyl-3,4-dihydrospiro[chromene-2,1'-cyclobutan]-4-yl)-3-(2-cyclo-pentyloxy-3-methoxy)phenylpropanamide

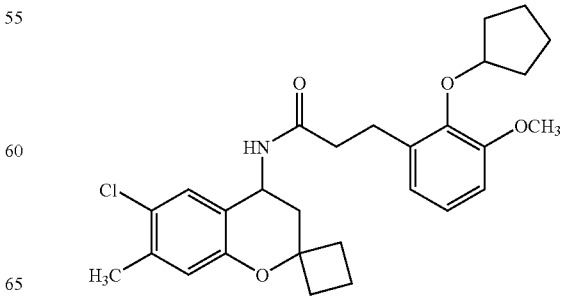

The title compound was prepared from Intermediate 14 (200 mg, 0.841 mmol) and 3-(2-cyclopentyloxy-3-methoxyphenyl))propanoic acid (222 mg, 0.841 mmol) in presence of EDCI.HCl (242 mg, 1.262 mmol), HOBt (129 mg, 0.841 mmol) and triethylamine (351 μl, 2.524 mmol) in dichloromethane (10 ml) as described in Example 1 to give 72 mg of the product as a white solid; IR (KBr) 3060, 2939, 1643, 1475, 1158, 1080, 882 cm$^{-1}$; $^1$H NMR (300 MHz, DMSO-d$_6$) δ 1.63-1.78 (m, 12H), 2.03-2.25 (m, 3H), 2.20-2.25 (m, 4H), 2.55 (t, J=7.2 Hz, 2H), 2.97 (t, J=7.5 Hz, 2H), 3.79 (s, 3H), 4.85 (br s, 1H), 5.14 (q, J=9.3 Hz, 1H), 5.70 (d, J=8.4 Hz, 1H), 6.63 (s, 1H), 6.78 (d, J=7.8 Hz, 2H), 6.85 (s, 1H), 6.96 (d, J=7.8 Hz, 1H); ESI-MS (m/z) 484.61 (M)$^+$.

Example 50

N-(5-Benzyloxy-3,4-dihydrospiro[chromene-2,1'-cyclobutan]-4-yl)-3-(2-cyclopentyloxy-3-methoxy)phenylpropanamide

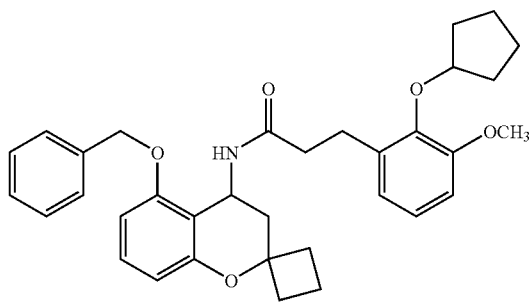 [SMILES: COc1cccc(CCC(=O)NC2CC3(CCC3)Oc3cccc(OCc4ccccc4)c32)c1OC1CCCC1]

The title compound was prepared from Intermediate 11 (246 mg, 0.833 mmol) and 3-(2-cyclopentyloxy-3-methoxyphenyl))propanoic acid (200 mg, 0.758 mmol) in presence of EDCI.HCl (218 mg, 1.137 mmol), HOBt (116 mg, 0.756 mmol) and triethylamine (316 μl, 2.274 mmol) in dichloromethane (10 ml) as described in Example 1 to give 170 mg of the product as a white solid; IR (KBr) 3293, 2956, 1631, 1465, 1120, 776 cm$^{-1}$; $^1$H NMR (300 MHz, CDCl$_3$) δ 1.59-1.70 (m, 4H), 1.88-1.92 (m, 5H), 2.00-2.06 (m, 5H), 2.23-2.36 (m, 4H), 2.78-2.84 (m, 2H), 3.75 (s, 3H), 4.77 (br s, 1H), 4.99 (s, 2H), 5.20 (q, J=3.0 Hz, 1H), 5.63 (d, J=6.0 Hz, 1H), 6.43-6.50 (m, 2H), 6.67 (d, J=7.8 Hz, 2H), 6.83-6.89 (m, 1H), 7.07-7.13 (m, 2H), 7.25-7.31 (m, 4H); ESI-MS (m/z) 542.38 (M+H)$^+$.

Example 51

N-(5-Hydroxy-3,4-dihydrospiro[chromene-2,1'-cyclobutan]-4-yl)-3-(2-cyclopentyloxy-3-methoxy)phenylpropanamide

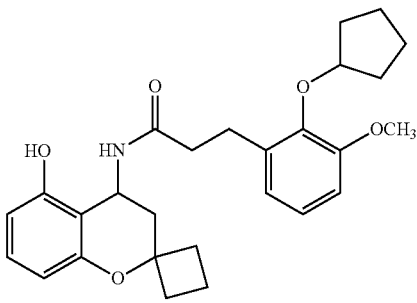 [SMILES: COc1cccc(CCC(=O)NC2CC3(CCC3)Oc3cccc(O)c32)c1OC1CCCC1]

Example 50 (140 mg, 0.258 mmol) was deprotected using Pd/C (28 mg) in methanol at 45 psi pressure for 4 h under nitrogen in paar apparatus. The reaction mixture was filtered through a celite bed. The filtrate was concentrated under reduced pressure to get a crude compound which was purified by silica gel column chromatography using 25% ethyl acetate in petroleum ether to give 51 mg of the product as a white solid; IR (KBr) 3275, 2955, 1638, 1463, 1117, 783 cm$^{-1}$; $^1$H NMR (300 MHz, CDCl$_3$) δ 1.20-1.30 (m, 4H), 1.76-1.88 (m, 5H), 2.05-2.17 (m, 5H), 2.50-2.56 (m, 4H), 2.92 (t, J=6.6 Hz, 2H), 3.80 (s, 3H), 4.87 (br s, 1H), 5.02-5.10 (m, 1H), 5.96 (d, J=8.7 Hz, 1H), 6.33 (d, J=7.8 Hz, 1H), 6.41 (d, J=8.4 Hz, 1H), 6.68-6.74 (m, 2H), 6.86 (t, J=7.8 Hz, 1H), 7.00 (t, J=8.4 Hz, 1H), 10.02 (br s, 1H, exchangeable with D$_2$O); ESI-MS (m/z) 452.51 (M+H)$^+$.

Example 52

N-(3,4-Dihydro spiro[chromene-2,1'-cyclobutan]-5-methoxy-4-yl)-3-(2-cyclopentyloxy-3-methoxy)phenylpropanamide

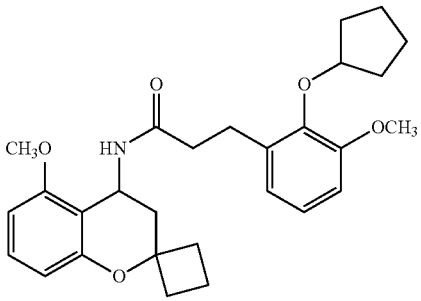

The title compound was prepared from Intermediate 15 (165 mg, 0.757 mmol) and 3-(2-cyclopentyloxy-3-methoxyphenyl))propanoic acid (200 mg, 0.757 mmol) in presence of EDCI.HCl (218 mg, 1.137 mmol), HOBt (116 mg, 0.757 mmol) and triethylamine (317 μl, 2.273 mmol) in dichloromethane (10 ml) as described in Example 1 to give 80 mg of the product as a white solid; IR (KBr) 3286, 2957, 1632, 1471, 1122, 775 cm$^{-1}$; $^1$H NMR (300 MHz, DMSO-d$_6$) δ 1.64-1.89 (m, 8H), 1.98-2.09 (m, 6H), 2.22-2.32 (m, 2H), 2.41-2.46 (m, 2H), 2.93 (t, J=7.8 Hz, 2H), 3.70 (s, 3H), 3.78 (s, 3H), 4.81 (br s, 1H), 5.14 (q, J=3.6 Hz, 1H), 5.54 (d, J=6.3 Hz, 1H), 6.36 (d, J=7.8 Hz, 1H), 6.46 (d, J=8.1 Hz, 1H), 6.70-6.80 (m, 2H), 6.91 (t, J=7.8 Hz, 1H), 7.11 (t, J=8.4 Hz, 1H); ESI-MS (m/z) 466.17 (M+H)$^+$.

Example 53

(4R)-6-Chloro-N-(3,4-dihydrospiro[chromene-2,1'-cyclobutan]-4-yl)-3-(2-cyclopentyl oxy-3-methyl) phenylpropanamide

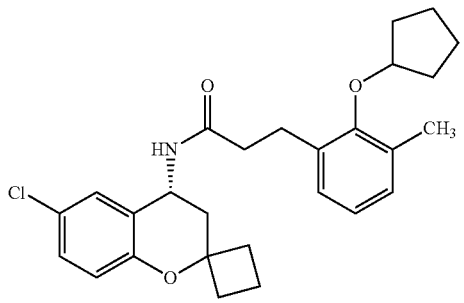 [SMILES: Cc1cccc(CCC(=O)N[C@@H]2CC3(CCC3)Oc3ccc(Cl)cc32)c1OC1CCCC1]

The title compound was prepared from Intermediate 8 (100 mg, 0.449 mmol) and 3-(2-cyclopentyloxy-3-methylphenyl) propanoic acid (122 mg, 0.491 mmol) in presence of EDCI-.HCl (129 mg, 0.675 mmol), HOBt (103 mg, 0.673 mmol) and triethylamine (187 μl, 1.346 mmol) in dichloromethane (10 ml) as described in Example 1 to give 126 mg of the product as a white solid; $^1$H NMR (300 MHz, CDCl$_3$) δ 1.70-1.81 (m, 8H), 2.06-2.33 (m, 11H), 2.64 (d, J=6.0 Hz, 2H), 3.03 (t, J=6.3 Hz, 2H), 4.74 (br s, 1H), 5.18 (q, J=6.0 Hz, 1H), 5.99 (d, J=7.8 Hz, 1H), 6.72 (d, J=8.7 Hz, 1H), 6.87 (s, 1H), 6.97-7.05 (m, 4H).

Example 54

(4S)-6-Chloro-N-(3,4-dihydrospiro[chromene-2,1'-cyclobutan]-4-yl)-3-(2-cyclopentyl oxy-3-methyl) phenylpropanamide

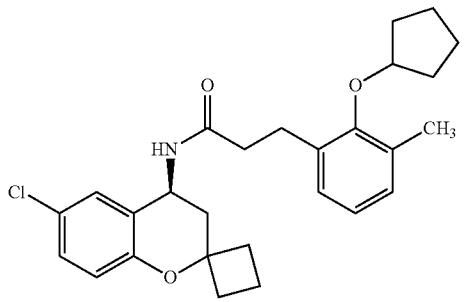 [SMILES: Cc1cccc(CCC(=O)N[C@H]2CC3(CCC3)Oc3ccc(Cl)cc32)c1OC1CCCC1]

The title compound was prepared from Intermediate 9 (100 mg, 0.449 mmol) and 3-(2-cyclopentyloxy-3-methylphenyl) propanoic acid (122 mg, 0.491 mmol) in presence of EDCI-.HCl (129 mg, 0.675 mmol), HOBt (103 mg, 0.673 mmol) and triethylamine (187 μl, 1.346 mmol) in dichloromethane (10 ml) as described in Example 1 to give 89 mg of the product as a white solid; $^1$H NMR (300 MHz, CDCl$_3$) δ 1.70-1.81 (m, 8H), 2.06-2.33 (m, 11H), 2.64 (d, J=6.0 Hz, 2H), 3.03 (t, J=6.3 Hz, 2H), 4.74 (br s, 1H), 5.18 (q, J=6.0 Hz, 1H), 5.99 (d, J=7.8 Hz, 1H), 6.72 (d, J=8.7 Hz, 1H), 6.87 (s, 1H), 6.97-7.05 (m, 4H).

Example 55

N-6-Chloro-3,4-dihydrospiro[chromene-2,1'-cyclobutan]-4-yl-3-(2-hydroxy-3-methoxy phenyl)propanamide

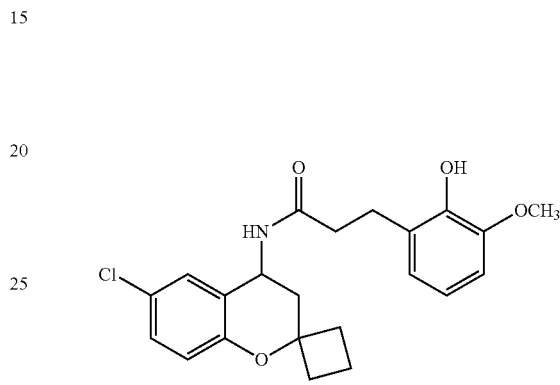

Step 1: (2E)-N-(6-Chloro-3,4-dihydrospiro [chromene-2,1'-cyclobutan]-4-yl)-3-(2-benzyloxy-3-methoxyphenyl)acrylamide This compound was prepared from Intermediate 2 (500 mg, 1.938 mmol) and (2E)-3-[2-(benzyloxy)-3-methoxyphenyl]acrylic acid (575 mg, 2.023 mmol) in presence of EDCI-.HCl (555 mg, 2.897 mmol), HOBt (443 mg, 2.897 mmol) and triethylamine (806 μl, 5.791 mmol) in dichloromethane (15 ml) as described in Example 1 to give 633 mg of the product as a white solid; $^1$H NMR (300 MHz, CDCl$_3$) δ 1.70-1.84 (m, 3H), 2.11-2.22 (m, 3H), 2.35-2.47 (m, 2H), 3.89 (s, 3H), 5.02 (q, J=11.4 Hz, 2H), 5.34 (q, J=9.9 Hz, 1H), 5.44 (d, J=8.4 Hz, 1H), 6.59 (d, J=15.6 Hz, 1H), 6.75 (d, J=8.4 Hz, 1H), 6.92-6.96 (m, 1H), 7.04-7.10 (m, 4H), 7.19-7.29 (m, 3H), 7.41 (d, J=6.6 Hz, 2H), 7.69 (d, J=16.2 Hz, 1H).

Step 2: N-6-Chloro-3,4-dihydrospiro[chromene-2,1'-cyclobutan]-4-yl-3-(2-hydroxy-3-methoxyphenyl) propanamide Step 1 intermediate (200 mg, 0.408 mmol) was deprotected and reduced using 5% Pd/C (50 mg) in ethyl acetate (20 ml) at 45 psi pressure for 4 h under nitrogen in paar apparatus. The reaction mixture was filtered through a celite bed. The filtrate was concentrated under reduced pressure to get a crude compound which was purified by silica gel column chromatography using 1% methanol in chloroform to give 121 mg of the product as a white solid; $^1$H NMR (300 MHz, CDCl$_3$) δ 1.57-1.69 (m, 2H), 1.83-1.88 (m, 1H), 2.11-2.17 (m, 3H), 2.26-2.36 (m, 2H), 2.62 (t, J=6.9 Hz, 2H), 3.02 (t, J=6.6 Hz, 2H), 3.85 (s, 3H), 5.17 (q, J=9.9 Hz, 1H), 5.60 (d, J=7.8 Hz, 1H), 6.07 (s, 1H), 6.67-6.76 (m, 4H), 6.82-6.86 (m, 1H), 7.04 (dd, J=6.3, 1.8 Hz, 1H).

Example 56

N-(6-Chloro-3,4-dihydrospiro[chromene-2,1'-cyclobutan]-4-yl)-3-(2-benzyloxy-3-methoxy)phenylpropanamide

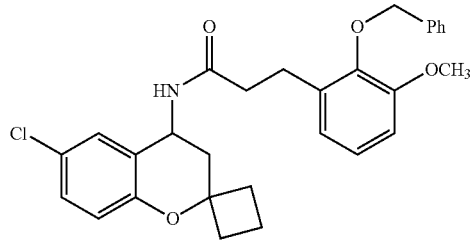 [SMILES: COc1cccc(CCC(=O)NC2CC3(CCC3)Oc3ccc(Cl)cc32)c1OCc1ccccc1]

To a stirred solution of Example 55N-6-Chloro-3,4-dihydrospiro[chromene-2,1'-cyclobutan]-4-yl-3-(2-hydroxy-3-methoxyphenyl)propanamide (150 mg, 0.371 mmol) in dimethyl formamide (5 ml) was added $K_2CO_3$ and benzyl bromide (70 mg, 0.411 mmol), dropwise at room temperature and stirred at the same temperature overnight. The reaction mixture was filtered and the filtrate extracted with ethyl acetate. Ethyl acetate layer was washed with water (2×20 ml), brine (20 ml), dried over $Na_2SO_4$ and concentrated. The crude product obtained was purified by silica gel column chromatography using 10% acetone in petroleum ether to give 130 mg of the product as a white solid; IR (KBr) 3283, 2939, 1644, 1476, 1263, 1082, 820 cm$^{-1}$; $^1$H NMR (300 MHz, CDCl$_3$) δ 1.63-1.86 (m, 2H), 2.02 (br s, 1H), 2.11-2.36 (m, 5H), 2.41 (t, J=7.2 Hz, 2H), 2.88 (t, J=7.8 Hz, 2H), 3.86 (s, 3H), 4.99 (s, 2H), 5.06 (q, J=6.0 Hz, 1H), 5.40 (d, J=7.8 Hz, 1H), 6.67-6.83 (m, 4H), 6.95-7.04 (m, 2H), 7.21-7.30 (m, 3H), 7.35 (d, J=7.2 Hz, 2H); ESI-MS (m/z) 492.14 (M)$^+$.

Example 57

N-(6-Chloro-3,4-dihydrospiro[chromene-2,1'-cyclobutan]-4-yl)-3-{2-isopropoxy-3-[(methylsulfonyl)amino]phenyl}propanamide

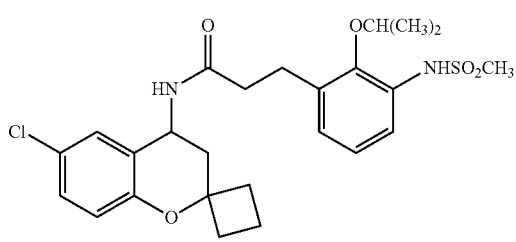

The title compound was prepared from Intermediate 2 (100 mg, 0.384 mmol) and 3-{2-isopropoxy-3-[(methylsulfonyl)amino]phenyl}propanoic acid (116 mg, 0.384 mmol) in presence of EDCl.HCl (111 mg, 0.576 mmol), HOBt (59 mg, 0.384 mmol) and triethylamine (134 µl, 0.961 mmol) in dichloromethane (5 ml) as described in Example 1 to give 122 mg of the product as a white solid; IR (KBr) 3331, 2950, 1645, 1473, 1140, 984 cm$^{-1}$; $^1$H NMR (300 MHz, CDCl$_3$) δ 1.35 (d, J=4.8 Hz, 6H), 1.65-1.72 (m, 2H), 1.89-1.95 (m, 1H), 2.10-2.18 (m, 3H), 2.31-2.38 (m, 2H), 2.59 (t, J=7.5 Hz, 2H), 3.00 (s, 5H), 4.22-4.28 (m, 1H), 5.21 (q, J=6.3 Hz, 1H), 5.60 (d, J=8.7 Hz, 1H), 6.71 (d, J=9.0 Hz, 1H), 6.86 (s, 1H), 6.95 (d, J=9.3 Hz, 2H), 7.01-7.08 (m, 2H), 7.37 (d, J=7.2 Hz, 1H); ESI-MS (m/z) 507.39 (M+H)$^+$.

Example 58

N-(8-Chloro-3,4-dihydrospiro[chromene-2,1'-cyclobutan]-4-yl)-3-{2-isopropoxy-3-[(methylsulfonyl)amino]phenyl}propanamide

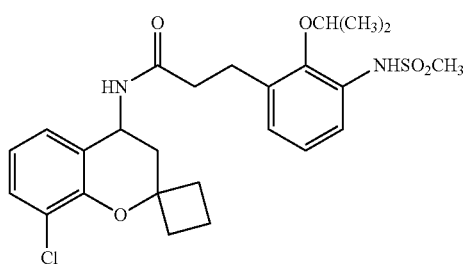

The title compound was prepared from Intermediate 1 (100 mg, 0.384 mmol) and 3-{2-isopropoxy-3-[(methylsulfonyl)amino]phenyl}propanoic acid (116 mg, 0.384 mmol) in presence of EDCl.HCl (111 mg, 0.576 mmol), HOBt (59 mg, 0.384 mmol) and triethylamine (134 µl, 0.961 mmol) in dichloromethane (5 ml) as described in Example 1 to give 121 mg of the product as a white solid; IR (KBr) 3302, 2937, 1643, 1449, 1151, 978 cm$^{-1}$; $^1$H NMR (300 MHz, CDCl$_3$) δ 1.34 (d, J=3.9 Hz, 6H), 1.68-1.79 (m, 2H), 1.89-1.95 (m, 1H), 2.18-2.25 (m, 3H), 2.36-2.46 (m, 2H), 2.58 (t, J=7.2 Hz, 2H), 2.99 (s, 5H), 4.23-4.29 (m, 1H), 5.25 (q, J=6.9 Hz, 1H), 5.58 (d, J=9.0 Hz, 1H), 6.72-6.78 (m, 2H), 6.85 (s, 1H), 6.96 (d, J=6.6 Hz, 1H), 7.04 (t, J=8.1 Hz, 1H), 7.19 (s, 1H), 7.37 (d, J=7.8 Hz, 1H); ESI-MS (m/z) 507.46 (M+H)$^+$.

Example 59

N-(6,8-Dichloro-3,4-dihydrospiro[chromene-2,1'-cyclobutan]-4-yl)-3-(2-cyclopentyloxy-3-methoxy)phenylpropanamide

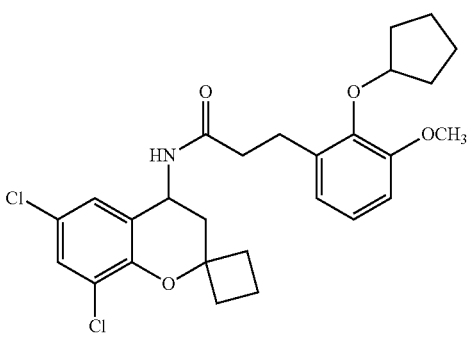 [SMILES: COc1cccc(CCC(=O)NC2CC3(CCC3)Oc3c(Cl)cc(Cl)cc32)c1OC1CCCC1]

The title compound was prepared from Intermediate 13 (150 mg, 0.511 mmol) and 3-[2-(cyclopentyloxy-3-methoxy)phenyl]propanoic acid (127 mg, 0.511 mmol) in presence of EDCI.HCl (147 mg, 0.766 mmol), HOBt (78 mg, 0.511 mmol) and triethylamine (249 µl, 1.788 mmol) in dichloromethane (10 ml) as described in Example 1 to give 85 mg of the product as a white solid; IR (KBr) 3277, 2956, 1644, 1451, 1246, 1080, 970 cm$^{-1}$; $^1$H NMR (300 MHz, CDCl$_3$) δ 1.62-1.68 (m, 3H), 1.74-1.88 (m, 8H), 2.04-2.27 (m, 4H), 2.58-2.61 (m, 3H), 2.96 (d, J=6.9 Hz, 2H), 3.79 (s, 3H), 4.85 (br s, 1H), 5.17 (q, J=9.3 Hz, 1H), 5.81 (d, J=8.1 Hz, 1H), 6.77 (d, J=8.4 Hz, 3H), 6.96 (t, J=7.8 Hz, 1H), 7.17 (s, 1H); ESI-MS (m/z) 504.16 (M)$^+$.

Example 60

N-(6,8-dichloro-3,4-dihydrospiro[chromene-2,1'-cyclobutan]-4-yl)-3-{[2-(dimethylamino)ethoxy-3-methoxy]phenyl}propanamide

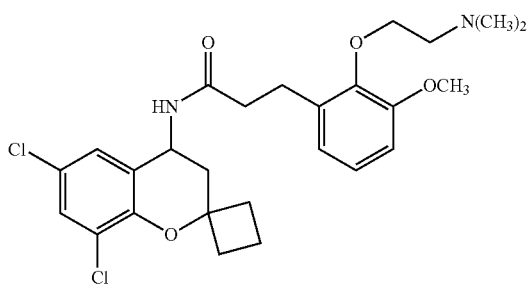 [SMILES: COc1cccc(CCC(=O)NC2CC3(CCC3)Oc3c(Cl)cc(Cl)cc32)c1OCCN(C)C]

The title compound was prepared from Intermediate 13 (100 mg, 0.339 mmol) and 3-{2-[2-(dimethylamino)ethoxy]-3-methoxyphenyl}propanoic acid (102 mg, 0.407 mmol) in presence of EDCI.HCl (97 mg, 0.509 mmol), HOBt (78 mg, 0.509 mmol) and triethylamine (141 µl, 1.017 mmol) in dichloromethane (10 ml) as described in Example 1 to give 57 mg of the product as a white solid; IR (KBr) 3273, 2938, 1651, 1539, 1454, 1268, 1247, 1081, 957 cm$^{-1}$; $^1$H NMR (300 MHz, CDCl$_3$) δ 1.17-1.25 (m, 3H), 1.63-1.74 (m, 2H), 1.91 (br s, 1H), 2.14-2.22 (m, 2H), 2.27 (s, 6H), 2.30-2.36 (m, 2H), 2.44-2.51 (m, 1H), 2.60-2.71 (m, 4H), 2.95-3.02 (m, 2H), 3.81 (s, 1H), 4.05-4.11 (m, 2H), 5.17-5.26 (m, 1H), 6.63 (d, J=7.8 Hz, 1H), 6.79 (d, J=7.5 Hz, 2H), 6.97 (t, J=7.8 Hz, 1H), 7.16 (s, 1H); APCI-MS (m/z) 507.81 (M+H)$^+$.

Example 61

N-(6,8-dichloro-3,4-dihydrospiro[chromene-2,1'-cyclobutan]-4-yl)-3-{2-propoxy-3-[(methylsulfonyl)amino]phenyl}propanamide

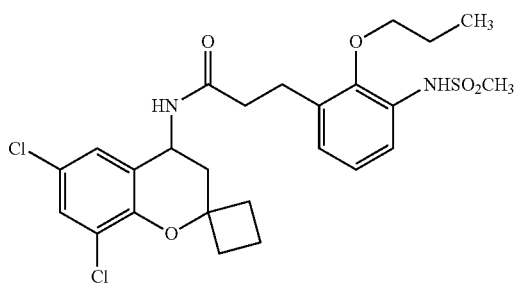

The title compound was prepared from Intermediate 13 (100 mg, 0.339 mmol) and 3-{3-[(methylsulfonyl)amino]-2-propoxyphenyl}propanoic acid (103 mg, 0.339 mmol) in presence of EDCI.HCl (98 mg, 0.509 mmol), HOBt (52 mg, 0.339 mmol) and triethylamine (119 µl, 0.848 mmol) in dichloromethane (10 ml) as described in Example 1 to give 119 mg of the product as a white solid; IR (KBr) 3305, 2937, 1644, 1451, 1141, 986 cm$^{-1}$; $^1$H NMR (300 MHz, CDCl$_3$) δ 1.08 (t, J=7.5 Hz, 3H), 1.68-1.75 (m, 2H), 1.82-1.89 (m, 3H), 2.14-2.20 (m, 3H), 2.32-2.38 (m, 1H), 2.42-2.50 (m, 1H), 2.60 (t, J=7.5 Hz, 2H), 3.04 (s, 5H), 3.81 (t, J=6.9 Hz, 2H), 5.24 (q, J=6.3 Hz, 1H), 5.62 (d, J=8.7 Hz, 1H), 6.81 (s, 1H), 6.86 (s, 1H), 6.97 (d, J=7.8 Hz, 1H), 7.07 (t, J=7.8 Hz, 1H), 7.20 (s, 1H), 7.38 (d, J=7.5 Hz, 1H); ESI-MS (m/z) 541.67 (M)$^+$.

Example 62

N-(6,8-Dichloro-3,4-dihydrospiro[chromene-2,1'-cyclobutan]-4-yl)-3-{2-isopropoxy-5-[(methylsulfonyl)amino]phenyl}propanamide

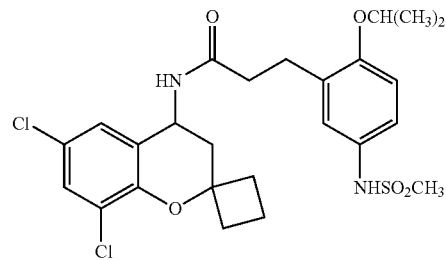

The title compound was prepared from Intermediate 13 (100 mg, 0.339 mmol) and 3-{2-isopropoxy-5-[(methylsulfonyl)amino]phenyl}propanoic acid (112 mg, 0.372 mmol) in presence of EDCI.HCl (98 mg, 0.509 mmol), HOBt (78 mg, 0.509 mmol) and triethylamine (142 µl, 1.017 mmol) in dichloromethane (5 ml) as described in Example 1 to give 90 mg of the product as a white solid; IR (KBr) 3275, 2935, 1648, 1497, 1152, 960 cm$^{-1}$; $^1$H NMR (300 MHz, CDCl$_3$) δ 1.30 (s, 6H), 1.58-1.64 (m, 2H), 1.70-1.76 (m, 2H), 2.10-2.17 (m, 2H), 2.38-2.45 (m, 2H), 2.58-2.65 (m, 2H), 2.90-3.02 (m, 4H), 4.49 (br s, 1H), 5.21 (br s, 1H), 5.74 (br s, 1H), 6.50-6.55

(m, 1H), 6.73-6.79 (m, 2H), 6.98-7.08 (m, 2H), 7.22 (d, J=15.6 Hz, 2H); APCI-MS (m/z) 541.60 (M+H)+.

Example 63

N-(6,8-Dichloro-3,4-dihydrospiro[chromene-2,1'-cyclobutan]-4-yl)-3-{2-butoxy-3-[(methylsulfonyl)amino]phenyl}propanamide

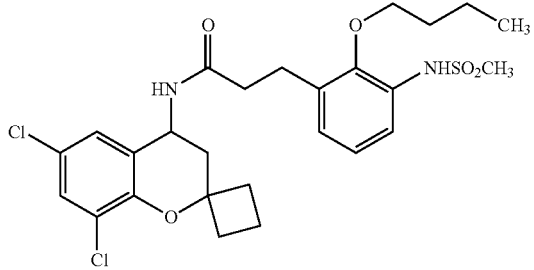

The title compound was prepared from Intermediate 13 (100 mg, 0.339 mmol) and 3-{2-butoxy-3-[(methylsulfonyl)amino]phenyl}propanoic acid (107 mg, 0.339 mmol) in presence of EDCI.HCl (98 mg, 0.509 mmol), HOBt (52 mg, 0.339 mmol) and triethylamine (119 μl, 0.848 mmol) in dichloromethane (10 ml) as described in Example 1 for 3 h to give 107 mg of the product as a white solid; IR (KBr) 3289, 2935, 1647, 1451, 1156, 979 cm$^{-1}$; $^1$H NMR (300 MHz, CDCl$_3$) δ 0.99 (t, J=7.2 Hz, 3H), 1.47-1.54 (m, 2H), 1.68-1.80 (m, 4H), 1.83-1.98 (m, 1H), 2.04-2.16 (m, 3H), 2.32-2.45 (m, 2H), 2.60 (t, J=6.9 Hz, 2H), 3.04 (s, 4H), 3.84 (t, J=6.3 Hz, 2H), 5.24 (q, J=6.6 Hz, 1H), 5.62 (d, J=9.3 Hz, 1H), 6.80 (s, 1H), 6.85 (s, 1H), 6.97 (d, J=7.8 Hz, 1H), 7.07 (t, J=7.8 Hz, 1H), 7.20 (s, 1H), 7.37 (d, J=7.8 Hz, 1H); ESI-MS (m/z) 555.32 (M)+.

Example 64

N-(6,8-Dichloro-3,4-dihydrospiro[chromene-2,1'-cyclobutan]-4-yl)-3-{2-(cyclopropyl methoxy)-3-[(methylsulfonyl)amino]phenyl}propanamide

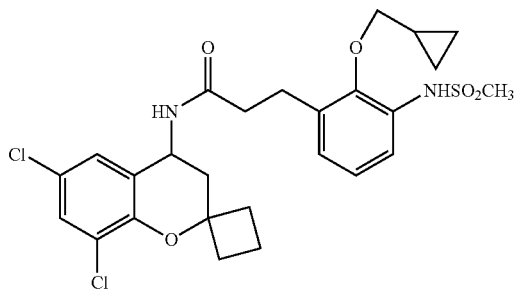

The title compound was prepared from Intermediate 13 (100 mg, 0.339 mmol) and 3-{2-(cyclopropylmethoxy)-3-[(methylsulfonyl)amino]phenyl}propanoic acid (107 mg, 0.339 mmol) in presence of EDCI.HCl (98 mg, 0.509 mmol), HOBt (52 mg, 0.339 mmol) and triethylamine (119 μl, 0.848 mmol) in dichloromethane (10 ml) as described in Example 1 for 3 h to give 140 mg of the product as a white solid; IR (KBr) 3303, 2934, 1644, 1451, 1140, 982 cm$^{-1}$; $^1$H NMR (300 MHz, CDCl$_3$) δ 0.35 (d, J=6.9 Hz, 2H), 0.69 (d, J=5.4 Hz, 2H), 1.22-1.26 (m, 2H), 1.68-1.80 (m, 2H), 1.83-1.98 (m, 1H), 2.12-2.20 (m, 3H), 2.32-2.45 (m, 2H), 2.60 (t, J=7.2 Hz, 2H), 3.03 (s, 4H), 3.73 (d, J=6.9 Hz, 2H), 5.24 (q, J=5.7 Hz, 1H), 5.62 (d, J=8.4 Hz, 1H), 6.87 (s, 1H), 6.97-7.07 (m, 3H), 7.20 (s, 1H), 7.37 (d, J=7.2 Hz, 1H); ESI-MS (m/z) 553.60 (M)+.

Example 65

N-(6,8-Dichloro-3,4-dihydrospiro[chromene-2,1'-cyclobutan]-4-yl)-3-{2-isopropoxy-3-[(methylsulfonyl)amino]phenyl}propanamide

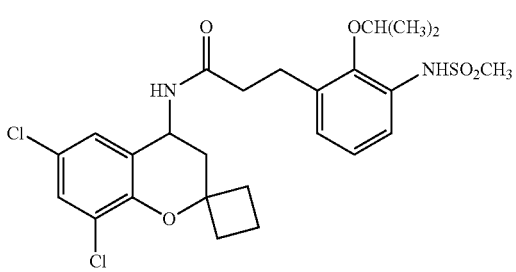

The title compound was prepared from Intermediate 13 (100 mg, 0.339 mmol) and 3-{2-isopropoxy-3-[(methylsulfonyl)amino]phenyl}propanoic acid (103 mg, 0.339 mmol) in presence of EDCI.HCl (98 mg, 0.509 mmol), HOBt (52 mg, 0.339 mmol) and triethylamine (119 μl, 0.848 mmol) in dichloromethane (10 ml) as described in Example 1 for 3 h to give 85 mg of the product as a white solid; IR (KBr) 3292, 2935, 1648, 1451, 1155, 979 cm$^{-1}$; $^1$H NMR (300 MHz, CDCl$_3$) δ 1.35 (d, J=5.7 Hz, 6H), 1.71 (t, J=3.4 Hz, 2H), 1.82-1.90 (m, 1H), 2.12-2.20 (m, 3H), 2.32-2.39 (m, 1H), 2.40-2.48 (m, 1H), 2.60 (t, J=7.5 Hz, 2H), 3.01 (s, 5H), 4.22-4.28 (m, 1H), 5.19 (q, J=9.0 Hz, 1H), 5.61 (d, J=9.0 Hz, 1H), 6.86 (s, 2H), 6.96 (d, J=7.8 Hz, 1H), 7.06 (t, J=8.4 Hz, 1H), 7.20 (s, 1H), 7.36 (d, J=8.1 Hz, 1H); ESI-MS (m/z) 540.86 (M)+.

Example 66

N-(6-Chloro-3,4-dihydrospiro[chromene-2,1'-cyclobutan]-4-yl)-3-(1-naphthyl)propanamide

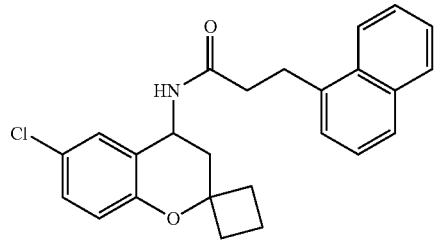 [SMILES: O=C(CCc1cccc2ccccc12)NC1CC2(CCC2)Oc2ccc(Cl)cc21]

The title compound was prepared from Intermediate 2 (200 mg, 0.896 mmol) and 1-naphthylpropanoic acid (178 mg, 0.896 mmol) in presence of EDCI.HCl (256 mg, 1.345 mmol), HOBt (205 mg, 1.345 mmol) and triethylamine (371 μl, 2.690 mmol) in dichloromethane (10 ml) as described in Example 1 to give 160 mg of the product as a white solid; $^1$H NMR (300 MHz, CDCl₃) δ 1.43-1.51 (m, 1H), 1.63-1.69 (m, 1H), 1.81-1.97 (m, 2H), 2.09-2.26 (m, 4H), 2.64-2.70 (m, 2H), 3.50 (t, J=7.2 Hz, 2H), 5.14 (q, J=9.9 Hz, 1H), 5.26 (d, J=8.4 Hz, 1H), 6.65 (d, J=8.7 Hz, 1H), 6.82 (s, 1H), 7.01 (dd, J=2.4, 8.7 Hz, 1H), 7.35-7.54 (m, 4H), 7.73 (d, J=6.9 Hz, 1H), 7.84 (d, J=7.5 Hz, 1H), 8.04 (d, J=8.1 Hz, 1H); ESI-MS (m/z) 406.34 (M+H)⁺.

Example 67

N-[4R-(6-Chloro-3,4-dihydrospiro[chromene-2,1'-cyclobutan]-4-yl)-3-(2-methoxy)-1-naphthylpropanamide

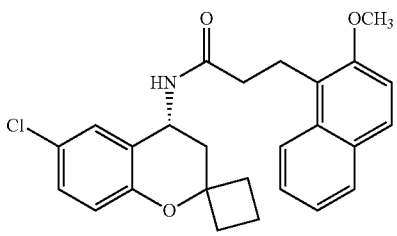 [SMILES: COc1ccc2ccccc2c1CCC(=O)N[C@@H]1CC2(CCC2)Oc2ccc(Cl)cc21]

The title compound was prepared from Intermediate 8 (100 mg, 0.449 mmol) and 3-(2-methoxy-1-naphthyl)propanoic acid (113 mg, 0.494 mmol) in presence of EDCI.HCl (129 mg, 0.677 mmol), HOBt (103 mg, 0.677 mmol) and triethylamine (187 μl, 1.348 mmol) in dichloromethane (10 ml) as described in Example 1 to give 91 mg of the product as a white solid; ¹H NMR (300 MHz, CDCl₃) δ 1.38-1.50 (m, 1H), 1.62-1.69 (m, 1H), 1.89-2.10 (m, 5H), 2.20-2.30 (m, 1H), 2.65 (t, J=7.2 Hz, 2H), 3.43-3.49 (m, 2H), 3.83 (s, 3H), 5.08 (q, J=9.3 Hz, 1H), 5.76 (d, J=8.1 Hz, 1H), 6.67 (d, J=8.7 Hz, 1H), 6.83 (s, 1H), 7.03 (dd, J=2.4, 6.3 Hz, 1H), 7.30 (s, 1H), 7.33-7.37 (m, 1H), 7.47-7.52 (m, 1H), 7.76 (t, J=8.4 Hz, 2H), 7.98 (d, J=8.4 Hz, 1H).

Example 68

N-[4(S)-(6-Chloro-3,4-dihydrospiro[chromene-2,1'-cyclobutan]-4-yl)-3-(2-methoxy)-1-naphthylpropanamide

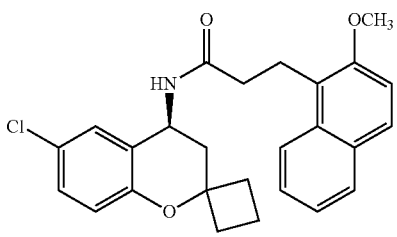 [SMILES: COc1ccc2ccccc2c1CCC(=O)N[C@H]1CC2(CCC2)Oc2ccc(Cl)cc21]

The title compound was prepared from Intermediate 9 (100 mg, 0.449 mmol) and 3-(2-methoxy-1-naphthyl)propanoic acid (113 mg, 0.494 mmol) in presence of EDCI.HCl (129 mg, 0.677 mmol), HOBt (103 mg, 0.677 mmol) and triethylamine (187 μl, 1.348 mmol) in dichloromethane (10 ml) as described in Example 1 to give 117 mg of the product as a white solid; ¹H NMR (300 MHz, CDCl₃) δ 1.38-1.50 (m, 1H), 1.62-1.69 (m, 1H), 1.89-2.10 (m, 5H), 2.20-2.30 (m, 1H), 2.65 (t, J=7.2 Hz, 2H), 3.43-3.49 (m, 2H), 3.83 (s, 3H), 5.08 (q, J=9.3 Hz, 1H), 5.76 (d, J=8.1 Hz, 1H), 6.67 (d, J=8.7 Hz, 1H), 6.83 (s, 1H), 7.03 (dd, J=2.4, 6.3 Hz, 1H), 7.30 (s, 1H), 7.33-7.37 (m, 1H), 7.47-7.52 (m, 1H), 7.76 (t, J=8.4 Hz, 2H), 7.98 (d, J=8.4 Hz, 1H).

Example 69

N-[(4R)-6-Chloro-3,4-dihydrospiro[chromene-2,1'-cyclobutan]-4-yl)-3-(4-methoxy)-1-naphthylpropanamide

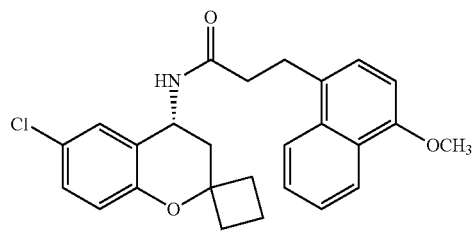 [SMILES: COc1ccc(CCC(=O)N[C@@H]2CC3(CCC3)Oc3ccc(Cl)cc32)c2ccccc12]

The title compound was prepared from Intermediate 8 (100 mg, 0.449 mmol) and 3-(4-methoxy-1-naphthyl)propanoic acid (102 mg, 0.449 mmol) in presence of EDCI.HCl (129 mg, 0.677 mmol), HOBt (103 mg, 0.677 mmol) and triethylamine (187 μl, 1.348 mmol) in dichloromethane (10 ml) as described in Example 1 for 4 h to give 110 mg of the product as a white solid; ¹H NMR (300 MHz, CDCl₃) δ 1.62-1.69 (m, 1H), 1.89-1.95 (m, 2H), 2.09-2.26 (m, 5H), 2.64 (t, J=5.4 Hz, 2H), 3.41 (t, J=7.5 Hz, 2H), 3.96 (s, 3H), 5.14 (q, J=8.1 Hz, 1H), 5.26 (d, J=8.7 Hz, 1H), 6.65 (d, J=8.7 Hz, 1H), 6.73 (d, J=7.8 Hz, 1H), 6.84 (s, 1H), 7.00 (d, J=9.0 Hz, 1H), 7.26-7.30 (m, 1H), 7.43-7.55 (m, 2H), 7.95 (d, J=8.1 Hz, 1H), 8.28 (d, J=8.1 Hz, 1H).

Example 70

N-[(4S)-6-Chloro-3,4-dihydrospiro[chromene-2,1'-cyclobutan]-4-yl)-3-(4-methoxy)-1-naphthylpropanamide

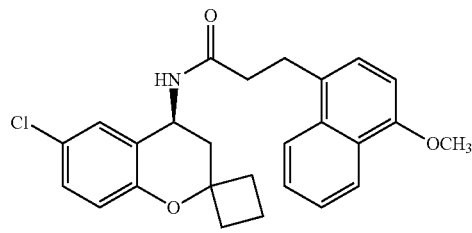 [SMILES: COc1ccc(CCC(=O)N[C@H]2CC3(CCC3)Oc3ccc(Cl)cc32)c2ccccc12]

The title compound was prepared from Intermediate 9 (100 mg, 0.449 mmol) and 3-(4-methoxy-1-naphthyl)propanoic acid (102 mg, 0.449 mmol) in presence of EDCI.HCl (129 mg, 0.677 mmol), HOBt (103 mg, 0.677 mmol) and triethylamine (187 μl, 1.348 mmol) in dichloromethane (10 ml) as described in Example 1 for 4 h to give 100 mg of the product as a white solid; ¹H NMR (300 MHz, CDCl₃) δ 1.62-1.69 (m, 1H), 1.89-1.95 (m, 2H), 2.09-2.26 (m, 5H), 2.64 (t, J=5.4 Hz, 2H), 3.41 (t, J=7.5 Hz, 2H), 3.96 (s, 3H), 5.14 (q, J=8.1 Hz, 1H), 5.26 (d, J=8.7 Hz, 1H), 6.65 (d, J=8.7 Hz, 1H), 6.73 (d, J=7.8 Hz, 1H), 6.84 (s, 1H), 7.00 (d, J=9.0 Hz, 1H), 7.26-7.30 (m, 1H), 7.43-7.55 (m, 2H), 7.95 (d, J=8.1 Hz, 1H), 8.28 (d, J=8.1 Hz, 1H).

Example 71

(4R)-6-Chloro-N-(3,4-dihydrospiro[chromene-2,1'-cyclobutan]-4-yl)-3-(4-difluoro-methoxy-1-naphthyl)propanamide

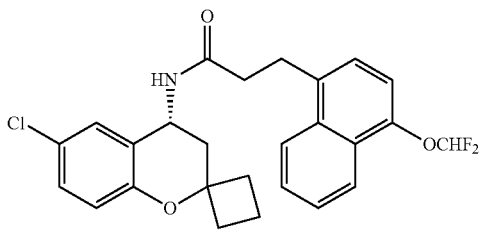 [SMILES: O=C(CCc1ccc(OC(F)F)c2ccccc12)N[C@@H]1CC2(CCC2)Oc2ccc(Cl)cc21]

The title compound was prepared from Intermediate 8 (100 mg, 0.447 mmol) and 3-(4-difluoromethoxy-1-naphthyl)propanoic acid (142 mg, 0.536 mmol) in presence of EDCI.HCl (128 mg, 0.671 mmol), HOBt (102 mg, 0.671 mmol) and triethylamine (124 μl, 0.894 mmol) in dichloromethane (10 ml) as described in Example 1 to give 89 mg of the product as a white solid; $^1$H NMR (300 MHz, CDCl$_3$) δ 1.53-1.64 (m, 2H), 1.88-1.97 (m, 2H), 2.13-2.25 (m, 5H), 2.63-2.69 (m, 2H), 3.47 (t, J=7.5 Hz, 2H), 5.17 (q, J=5.7 Hz, 1H), 5.32 (d, J=6.3 Hz, 1H), 6.65 (t, J=8.7 Hz, 1H), 6.86 (d, J=6.6 Hz, 1H), 7.02 (d, J=8.4 Hz, 1H), 7.11 (d, J=7.8 Hz, 1H), 7.31 (d, J=7.2 Hz, 1H), 7.55-7.60 (m, 2H), 8.03 (d, J=7.5 Hz, 1H), 8.21 (d, J=7.5 Hz, 1H).

Example 72

(4S)-6-Chloro-N-(3,4-dihydrospiro[chromene-2,1'-cyclobutan]-4-yl)-3-(4-difluoro methoxy-1-naphthyl)propanamide

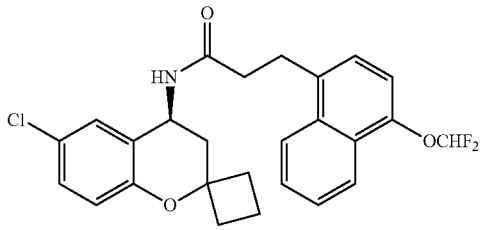 [SMILES: O=C(CCc1ccc(OC(F)F)c2ccccc12)N[C@H]1CC2(CCC2)Oc2ccc(Cl)cc21]

The title compound was prepared from Intermediate 9 (100 mg, 0.449 mmol) and 3-(4-difluoromethoxy-1-naphthyl)propanoic acid (142 mg, 0.536 mmol) in presence of EDCI.HCl (128 mg, 0.671 mmol), HOBt (102 mg, 0.671 mmol) and triethylamine (124 μl, 0.894 mmol) in dichloromethane (10 ml) as described in Example 1 to give 62 mg of the product as a white solid; $^1$H NMR (300 MHz, CDCl$_3$) δ 1.53-1.64 (m, 2H), 1.88-1.97 (m, 2H), 2.13-2.25 (m, 5H), 2.63-2.69 (m, 2H), 3.47 (t, J=7.5 Hz, 2H), 5.17 (q, J=5.7 Hz, 1H), 5.32 (d, J=6.3 Hz, 1H), 6.65 (t, J=8.7 Hz, 1H), 6.86 (d, J=6.6 Hz, 1H), 7.02 (d, J=8.4 Hz, 1H), 7.11 (d, J=7.8 Hz, 1H), 7.31 (d, J=7.2 Hz, 1H), 7.55-7.60 (m, 2H), 8.03 (d, J=7.5 Hz, 1H), 8.21 (d, J=7.5 Hz, 1H).

Example 73

N-(6-Chloro-3,4-dihydrospiro[chromene-2,1'-cyclobutan]-4-yl)-3-(2-naphthyl)propanamide

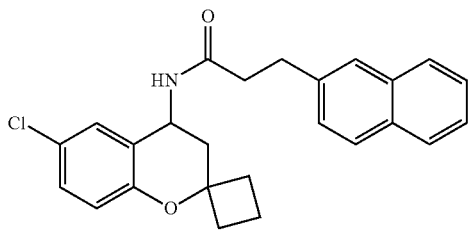 [SMILES: O=C(CCc1ccc2ccccc2c1)NC1CC2(CCC2)Oc2ccc(Cl)cc21]

The title compound was prepared from Intermediate 2 (100 mg, 0.506 mmol) and 3-(2-naphthyl)propanoic acid (103 mg, 0.506 mmol) in presence of EDCI.HCl (143 mg, 0.751 mmol), HOBt (114 mg, 0.751 mmol) and triethylamine (209 μl, 1.518 mmol) in dichloromethane (10 ml) as described in Example 1 for 3 h to give 101 mg of the product as a white solid; IR (KBr) 3287, 2937, 1645, 1475, 1234, 817 cm$^{-1}$; $^1$H NMR (300 MHz, CDCl$_3$) δ 1.41-1.48 (m, 1H), 1.80-1.86 (m, 2H), 2.06-2.26 (m, 4H), 2.56-2.68 (m, 2H), 3.19 (t, J=7.2 Hz, 2H), 3.47 (s, 1H), 5.17 (q, J=9.0 Hz, 1H), 5.35 (d, J=7.8 Hz, 1H), 6.65 (d, J=8.7 Hz, 1H), 6.91 (s, 1H), 7.01 (d, J=8.4 Hz, 1H), 7.33-7.42 (m, 3H), 7.65 (s, 1H), 7.77 (d, J=8.1 Hz, 3H); ESI-MS (m/z) 406.56 (M+H)$^+$.

Example 74

N-[4R-(6-Chloro-3,4-dihydrospiro[chromene-2,1'-cyclobutan]-4-yl)-3-(6-methoxy-2-naphthyl)propanamide

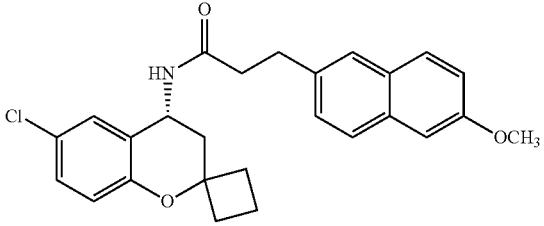 [SMILES: COc1ccc2cc(CCC(=O)N[C@@H]3CC4(CCC4)Oc4ccc(Cl)cc43)ccc2c1]

The title compound was prepared from Intermediate 8 (150 mg, 0.674 mmol) and 3-(6 methoxy-2-naphthyl)propanoic acid (170 mg, 0.741 mmol) in presence of EDCI.HCl (193 mg, 1.017 mmol), HOBt (154 mg, 1.011 mmol) and triethylamine (281 μl, 2.022 mmol) in dichloromethane (10 ml) as described in Example 1 to give 190 mg of the product as a white solid; $^1$H NMR (300 MHz, CDCl$_3$) δ 1.42-1.50 (m, 1H), 1.80-1.86 (m, 2H), 2.06-2.20 (m, 4H), 2.54-2.68 (m, 2H), 3.15 (t, J=6.6 Hz, 2H), 3.89 (s, 3H), 5.15 (q, J=6.0 Hz, 1H), 5.35 (d, J=7.8 Hz, 1H), 6.65 (d, J=7.8 Hz, 1H), 6.89 (s, 1H), 7.05 (d, J=7.8 Hz, 1H), 7.09 (d, J=8.4 Hz, 2H), 7.29 (d, J=8.4 Hz, 1H), 7.57 (s, 1H), 7.65 (d, J=7.8 Hz, 2H).

Example 75

N-[4S-(6-Chloro-3,4-dihydrospiro[chromene-2,1'-cyclobutan]-4-yl)-3-(6-methoxy-2-naphthyl)propanamide

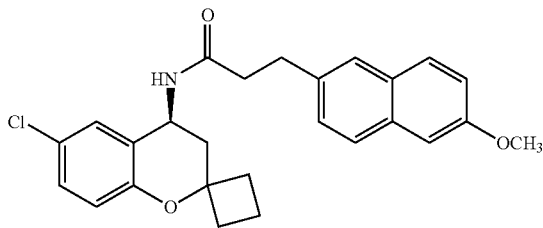 [SMILES: COc1ccc2cc(CCC(=O)N[C@H]3CC4(CCC4)Oc4ccc(Cl)cc43)ccc2c1]

The title compound was prepared from Intermediate 9 (150 mg, 0.674 mmol) and 3-(6-methoxy-2-naphthyl)propanoic acid (170 mg, 0.741 mmol) in presence of EDCI.HCl (193 mg, 1.017 mmol), HOBt (154 mg, 1.011 mmol) and triethylamine (281 μA, 2.022 mmol) in dichloromethane (10 ml) as described in Example 1 to give 127 mg of the product as a white solid; IR (KBr) 3293, 2956, 1631, 1465, 1120, 776 cm$^{-1}$; $^1$H NMR (300 MHz, CDCl$_3$) δ 1.42-1.50 (m, 1H), 1.80-1.86 (m, 2H), 2.06-2.20 (m, 4H), 2.54-2.68 (m, 2H), 3.15 (t, J=6.6 Hz, 2H), 3.89 (s, 3H), 5.15 (q, J=6.0 Hz, 1H), 5.35 (d, J=7.8 Hz, 1H), 6.65 (d, J=7.8 Hz, 1H), 6.89 (s, 1H), 7.05 (d, J=7.8 Hz, 1H), 7.09 (d, J=8.4 Hz, 2H), 7.29 (d, J=8.4 Hz, 1H), 7.57 (s, 1H), 7.65 (d, J=7.8 Hz, 2H); ESI-MS (m/z) 542.38 (M+H)$^+$.

Example 76

N-(6-Chloro-3,4-dihydrospiro[chromene-2,1'-cyclobutan]-4-yl)-3-(quinolin-2-yl)propanamide

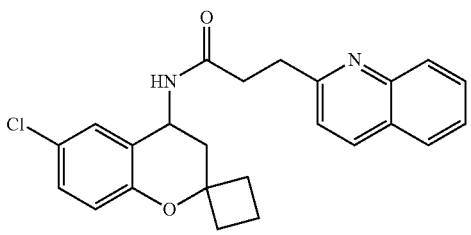 [SMILES: O=C(CCc1ccc2ccccc2n1)NC1CC2(CCC2)Oc2ccc(Cl)cc21]

Step 1: (2E)-N-(6-Chloro-3,4-dihydrospiro[chromene-2,1'-cyclobutan]-4-yl)-3-quinolin-2-ylacrylamide This compound was prepared from Intermediate 2 (200 mg, 0.894 mmol) and (2E)-3-quinolin-2-ylacrylic acid (213 mg, 1.073 mmol) in presence of EDCI.HCl (257 mg, 1.342 mmol), HOBt (205 mg, 1.342 mmol) and triethylamine (248 μl, 2.684 mmol) in dichloromethane (10 ml) as described in Example 1 to give 167 mg of the product as a white solid; $^1$H NMR (300 MHz, DMSO-d$_6$) δ 1.69-1.92 (m, 3H), 2.04-2.16 (m, 3H), 2.27-2.41 (m, 2H), 5.20 (q, J=10.2 Hz, 1H), 6.81 (d, J=9.0 Hz, 1H), 7.10-7.20 (m, 2H), 7.27 (d, J=15.6 Hz, 1H), 7.60 (t, J=7.8 Hz, 1H), 7.73-7.77 (m, 2H), 7.92-7.99 (m, 2H), 8.29 (s, 1H), 8.40 (d, J=8.1 Hz, 1H), 8.88 (d, J=8.4 Hz, 1H).

Step 2: N-(6-Chloro-3,4-dihydrospiro[chromene-2,1'-cyclobutan]-4-yl)-3-(quinolin-2-yl)propanamide Step 1 intermediate (150 mg, 0.388 mmol) was reduced using 10% Pd/C (50 mg) in ethyl acetate (25 ml) at 50 psi pressure for 2 h under nitrogen in paar apparatus. The reaction mixture was filtered through a celite bed and the filtrate concentrated under reduced pressure to get a crude compound which was purified by silica gel column chromatography using 1% methanol in chloroform to give 121 mg of the product as a white solid; $^1$H NMR (300 MHz, DMSO-d$_6$) δ 1.64-1.77 (m, 3H), 2.00-2.07 (m, 3H), 2.19-2.28 (m, 2H), 2.67-2.82 (m, 2H), 3.17-3.26 (m, 2H), 5.02 (br s, 1H), 6.72 (d, J=9.0 Hz, 1H), 6.94 (s, 1H), 7.10 (d, J=8.4 Hz, 1H), 7.44-7.54 (m, 2H), 7.69 (t, J=7.5 Hz, 1H), 7.91 (d, J=7.2 Hz, 2H), 8.25 (d, J=8.1 Hz, 1H), 8.40 (d, J=8.4 Hz, 1H).

Example 77

N-(6-Chloro-3,4-dihydrospiro[chromene-2,1'-cyclobutan]-4-yl)-3-(1H-indol-3-yl)-propanamide

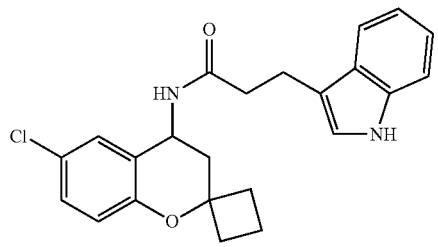 [SMILES: O=C(CCc1c[nH]c2ccccc12)NC1CC2(CCC2)Oc2ccc(Cl)cc21]

The title compound was prepared from Intermediate 2 (200 mg, 0.894 mmol) and 3-(1H-indol-3-yl)propanoic acid (187 mg, 0.988 mmol) in presence of EDCI.HCl (258 mg, 1.345 mmol), HOBt (206 mg, 1.345 mmol) and triethylamine (375 μl, 2.684 mmol) in dichloromethane (10 ml) as described in Example 1 to give 121 mg of the product as a white solid; IR (KBr) 3395, 2926, 1642, 1474, 1234, 748 cm$^{-1}$; $^1$H NMR (300 MHz, CDCl$_3$) δ 1.78-1.96 (m, 2H), 2.09-2.26 (m, 6H), 2.63 (t, J=6.3 Hz, 2H), 3.17-3.21 (m, 2H), 5.15 (q, J=9.6 Hz, 1H), 5.34 (d, J=8.4 Hz, 1H), 6.65 (d, J=8.7 Hz, 1H), 6.77 (s, 1H), 6.99-7.14 (m, 4H), 7.35 (d, J=7.8 Hz, 1H), 7.59 (d, J=7.8 Hz, 1H), 8.05 (s, 1H); ESI-MS (m/z) 395.63 (M+H)+.

Example 78

N-(6-chloro-3,4-dihydrospiro[chromene-2,1'-cyclobutan]-4-yl)-3-(2-methyl, 7-methoxy-1-benzofuran-4-yl)propanamide

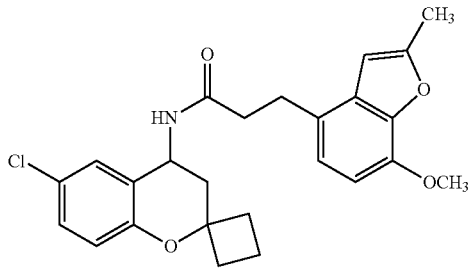 [SMILES: COc1ccc(CCC(=O)NC2CC3(CCC3)Oc3ccc(Cl)cc32)c2cc(C)oc12]

The title compound was prepared from Intermediate 2 (200 mg, 0.896 mmol) and 3-(2-methyl, 7-methoxy-1-benzofuran-4-yl)propanoic acid (209 mg, 0.896 mmol) in presence of EDCI.HCl (256 mg, 1.345 mmol), HOBt (205 mg, 1.345 mmol) and triethylamine (371 µl, 2.690 mmol) in dichloromethane (10 ml) as described in Example 1 for 4 h to give 60 mg of the product as a white solid; IR (KBr) 3395, 2972, 1642, 1515, 1423, 1235, 775 cm$^{-1}$; $^1$H NMR (300 MHz, CDCl$_3$) δ 1.41-1.61 (m, 4H), 1.90-1.98 (m, 4H), 2.46 (s, 3H), 2.55-2.62 (m, 2H), 3.96 (s, 3H), 5.10-5.16 (m, 1H), 5.26 (d, J=8.4 Hz, 2H), 6.40-6.46 (m, 1H), 6.60-6.70 (m, 3H), 6.83 (s, 1H), 6.91 (d, J=7.8 Hz, 1H), 7.02 (d, J=7.5 Hz, 1H); ESI-MS (m/z) 395.63 (M+H)+.

Example 79

N-[(4R)-6-Chloro-3,4-dihydrospiro[chromene-2,1'-cyclobutan]-4-yl]-3-(7-methoxy-2-methyl-1-benzofuran-5-yl)propanamide

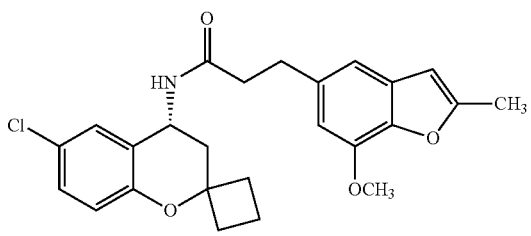 [SMILES: COc1cc(CCC(=O)N[C@@H]2CC3(CCC3)Oc3ccc(Cl)cc32)cc2cc(C)oc12]

The title compound was prepared from Intermediate 8 (200 mg, 0.894 mmol) and 3-(7-methoxy-2-methyl-1-benzofuran-4-yl)propanoic acid (252 mg, 1.078 mmol) in presence of EDCI.HCl (258 mg, 1.345 mmol), HOBt (206 mg, 1.345 mmol) and triethylamine (375 µl, 2.684 mmol) in dichloromethane (10 ml) as described in Example 1 to give 231 mg of the product as a white solid; $^1$H NMR (300 MHz, CDCl$_3$) δ 1.47-1.55 (m, 1H), 1.63-1.74 (m, 2H), 1.84-1.99 (m, 5H), 2.09-2.18 (s, 3H), 2.52-2.57 (m, 2H), 3.11-3.16 (m, 2H), 3.95 (s, 3H), 5.14 (q, J=9.3 Hz, 1H), 5.30 (d, J=7.8 Hz, 1H), 6.42 (s, 1H), 6.64-6.68 (m, 2H), 6.83 (s, 1H), 6.91 (d, J=7.8 Hz, 1H), 7.02 (dd, J=2.4, 6.9 Hz, 1H).

Example 80

N-[(4S)-6-chloro-3,4-dihydrospiro[chromene-2,1'-cyclobutan]-4-yl)-3-(7-methoxy-2-methyl-1-benzofuran-5-yl)propanamide

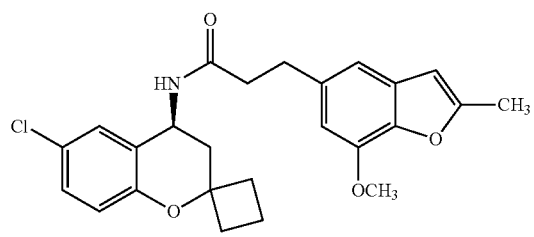 [SMILES: COc1cc(CCC(=O)N[C@H]2CC3(CCC3)Oc3ccc(Cl)cc32)cc2cc(C)oc12]

The title compound was prepared from Intermediate 9 (200 mg, 0.898 mmol) and 3-(7-methoxy-2-methyl-1-benzofuran-5-yl)propanoic acid (252 mg, 1.078 mmol) in presence of EDCI.HCl (258 mg, 1.347 mmol), HOBt (206 mg, 1.347 mmol) and triethylamine (375 µl, 2.698 mmol) in dichloromethane (10 ml) as described in Example 1 to give 199 mg of the product as a white solid; $^1$H NMR (300 MHz, CDCl$_3$) δ 1.47-1.55 (m, 1H), 1.63-1.74 (m, 2H), 1.84-1.99 (m, 5H), 2.09-2.18 (s, 3H), 2.52-2.57 (m, 2H), 3.11-3.16 (m, 2H), 3.95 (s, 3H), 5.14 (q, J=9.3 Hz, 1H), 5.30 (d, J=7.8 Hz, 1H), 6.42 (s, 1H), 6.64-6.68 (m, 2H), 6.83 (s, 1H), 6.91 (d, J=7.8 Hz, 1H), 7.02 (dd, J=2.4, 6.9 Hz, 1H).

Example 81

3-(1,4-Benzodioxin-6-yl)-N-(6-fluoro-3,4-dihydrospiro[chromene-2,1'-cyclobutan]-4-yl)propanamide

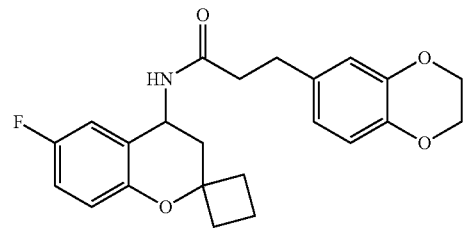 [SMILES: O=C(CCc1ccc2c(c1)OCCO2)NC1CC2(CCC2)Oc2ccc(F)cc21]

The title compound was prepared from Intermediate 6 (200 mg, 0.963 mmol) and 3-(2,3-dihydro-1,4-benzodioxin-6-yl)propanoic acid (187 mg, 0.963 mmol) in presence of EDCI.HCl (276 mg, 1.441 mmol), HOBt (221 mg, 1.441 mmol) and triethylamine (403 µl, 2.891 mmol) in dichloromethane (10 ml) as described in Example 1 to give 16 mg of the product as a white solid; IR (KBr) 3307, 2951, 1869, 1643, 1508, 1257, 1071, 817 cm$^{-1}$; $^1$H NMR (300 MHz, DMSO-d$_6$) δ 1.13-1.23 (m, 1H), 1.66-1.78 (m, 3H), 2.04-2.13 (m, 3H), 2.18-2.27 (m, 2H), 2.42-2.49 (m, 1H), 2.72-2.79 (m, 2H), 4.17 (s, 4H), 5.01 (br s, 1H), 6.54 (d, J=11.1 Hz, 1H), 6.38-

6.74 (m, 4H), 6.93 (t, J=8.1 Hz, 1H), 8.25 (d, J=8.4 Hz, 1H); ESI-MS (m/z) 396.66 (M–H)⁻.

Example 82

3-(1,3-Benzodioxol-4-yl)-N-[6-chloro-3,4-dihydrospiro[chromene-2,1'-cyclobutan]-4-yl]propanamide

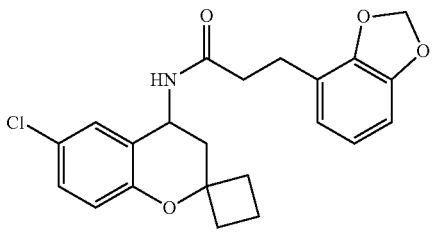 [SMILES: O=C(CCc1cccc2c1OCO2)NC1CC2(CCC2)Oc2ccc(Cl)cc21]

The title compound was prepared from Intermediate 2 (150 mg, 0.679 mmol) and 3-(1,3-benzodioxol-4-yl)propanoic acid (169 mg, 0.892 mmol) in presence of EDCI.HCl (192 mg, 1.005 mmol), HOBt (154 mg, 1.005 mmol) and triethylamine (135 μl, 1.341 mmol) in dichloromethane (10 ml) as described in Example 1 to give 137 mg of the product as a white solid; IR (KBr) 3314, 2940, 1640, 1456, 1243, 1064 cm⁻¹; ¹H NMR (300 MHz, CDCl₃) δ 1.63-1.72 (m, 2H), 1.85-1.89 (m, 1H), 2.04-2.17 (m, 3H), 2.27-2.37 (m, 2H), 2.58 (t, J=6.9 Hz, 2H), 2.96-3.02 (m, 2H), 5.20 (q, J=9.3 Hz, 1H), 5.54 (d, J=8.7 Hz, 1H), 5.87 (d, J=8.7 Hz, 2H), 6.69-6.80 (m, 4H), 6.92 (s, 1H), 7.05 (d, J=8.7 Hz, 1H).

Example 83

3-(1,3-Benzodioxol-4-yl)-N-(8-chloro-3,4-dihydrospiro[chromene-2,1'-cyclobutan]-4-yl)propanamide

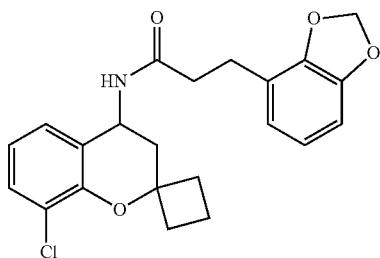 [SMILES: O=C(CCc1cccc2c1OCO2)NC1CC2(CCC2)Oc2c(Cl)cccc21]

The title compound was prepared from Intermediate 1 (150 mg, 0.679 mmol) and 3-(1,3-benzodioxol-4-yl)propanoic acid (169 mg, 0.892 mmol) in presence of EDCI.HCl (192 mg, 1.005 mmol), HOBt (154 mg, 1.005 mmol) and triethylamine (135 μl, 1.341 mmol) in dichloromethane (10 ml) as described in Example 1 to give 56 mg of the product as a white solid; IR (KBr) 3371, 2940, 1651, 1461, 1245, 1064, 934 cm⁻¹; ¹H NMR (300 MHz, CDCl₃) δ 1.67-1.77 (m, 2H), 1.90-1.95 (m, 1H), 2.06-2.20 (m, 3H), 2.32-2.47 (m, 2H), 2.58 (t, J=7.5 Hz, 2H), 2.96-3.02 (m, 2H), 5.26 (q, J=9.3 Hz, 1H), 5.55 (d, J=8.7 Hz, 1H), 5.85 (d, J=13.8 Hz, 2H), 6.66-6.80 (m, 5H), 7.18 (d, J=6.9 Hz, 1H); ESI-MS (m/z) 400.58 (M+H)⁺.

Example 84

3-(1,4-Benzodioxin-5-yl)-N-(6-chloro-3,4-dihydrospiro[chromene-2,1'-cyclobutan]-4-yl)propanamide

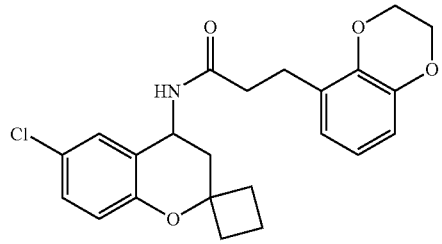 [SMILES: O=C(CCc1cccc2c1OCCO2)NC1CC2(CCC2)Oc2ccc(Cl)cc21]

The title compound was prepared from Intermediate 2 (200 mg, 0.769 mmol)) and 3-(2,3-dihydro-1,4-benzodioxin-5-yl)propanoic acid (191 mg, 0.923 mmol) in presence of EDCI.HCl (221 mg, 1.153 mmol), HOBt (176 mg, 1.153 mmol) and triethylamine (321 μl, 2.307 mmol) in dichloromethane (10 ml) as described in Example 1 to give 141 mg of the product as a white solid; IR (KBr) 3276, 2935, 1639, 1474, 1262, 1094 cm⁻¹; ¹H NMR (300 MHz, CDCl₃) δ 1.63-1.71 (m, 3H), 1.89 (br s, 1H), 2.13-2.27 (m, 2H), 2.33-2.37 (m, 2H), 2.57 (t, J=7.5 Hz, 2H), 2.96 (t, J=6.9 Hz, 2H), 4.19 (d, J=6.3 Hz, 4H), 5.19 (q, J=8.7 Hz, 1H), 5.62 (d, J=8.1 Hz, 1H), 6.69-6.74 (m, 4H), 6.95 (s, 1H), 7.05 (d, J=8.1 Hz, 1H); ESI-MS (m/z) 414.47 (M+H)⁺.

Example 85

N-(6-Chloro-3,4-dihydrospiro[chromene-2,1'-cyclobutan]-4-yl)-3-(dibenzo[b,d]furan-4-yl)propanamide

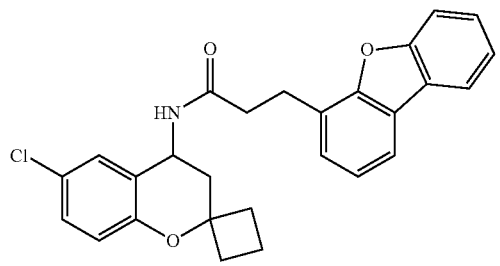 [SMILES: O=C(CCc1cccc2c1oc1ccccc12)NC1CC2(CCC2)Oc2ccc(Cl)cc21]

The title compound was prepared from Intermediate 2 (200 mg, 0.896 mmol) and 3-dibenzo[b,d]furan-4-ylpropanoic acid (214 mg, 0.896 mmol) in presence of EDCI.HCl (256 mg, 1.345 mmol), HOBt (205 mg, 1.345 mmol) and triethylamine (371 μl, 2.690 mmol) in dichloromethane (10 ml) as described in Example 1 for 4 h to give 215 mg of the product as a white solid; ¹H NMR (300 MHz, CDCl₃) δ 1.81-1.91 (m, 3H), 2.08-2.13 (m, 3H), 2.17-2.26 (m, 2H), 2.72-2.79 (m, 2H), 3.35-3.41 (m, 2H), 5.16 (q, J=9.3 Hz, 1H), 5.44 (d, J=8.7 Hz, 1H), 6.63 (d, J=8.7 Hz, 1H), 6.82 (s, 1H), 6.99 (dd, J=6.3, 1.8 Hz, 1H), 7.28-7.33 (m, 3H), 7.42 (t, J=6.9 Hz, 1H), 7.53

(d, J=8.7 Hz, 1H), 7.82 (d, J=6.3 Hz, 1H), 7.91 (d, J=8.7 Hz, 1H); ESI-MS (m/z) 446.29 (M+H)$^+$.

Example 86

N-(6-Chloro-3,4-dihydrospiro[chromene-2,1'-cyclopentan]-4-yl)-3-(2-cyclopentyloxy-3-methoxy)propanamide

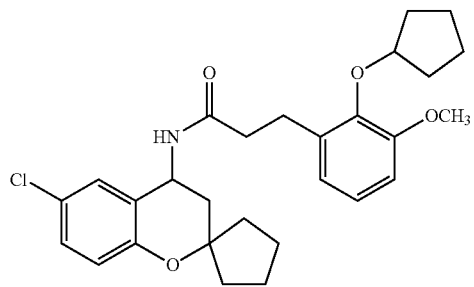 [SMILES: COc1cccc(CCC(=O)NC2CC3(CCCC3)Oc3ccc(Cl)cc32)c1OC1CCCC1]

The title compound was prepared from Intermediate 16 (200 mg, 0.841 mmol) and 3-(2-cyclopentyloxy-3-methoxyphenyl)propanoic acid (266 mg, 1.009 mmol) in presence of EDCI.HCl (241 mg, 1.261 mmol), HOBt (193 mg, 1.261 mmol) and triethylamine (351 μl, 2.504 mmol) in dichloromethane (10 ml) as described in Example 1 to give 197 mg of the product as a white solid; IR (Neat) 3276, 2959, 1642, 1475, 1262, 1082 cm$^{-1}$; $^1$H NMR (300 MHz, CDCl$_3$) δ 1.74-2.05 (m, 18H), 2.56 (t, J=6.3 Hz, 2H), 2.96 (t, J=6.3 Hz, 2H), 3.79 (s, 3H), 4.58 (br s, 1H), 5.14 (q, J=9.0 Hz, 1H), 5.73 (d, J=8.4 Hz, 1H), 6.63 (d, J=8.7 Hz, 1H), 6.77 (d, J=7.8 Hz, 2H), 6.95-7.00 (m, 3H); ESI-MS (m/z) 484.64 (M)$^+$.

Example 87

N-(6-Chloro-3,4-dihydrospiro[chromene-2,1'-cyclohexan]-4-yl)-3-(2-cyclopentyloxy-3-methoxy)phenylpropanamide

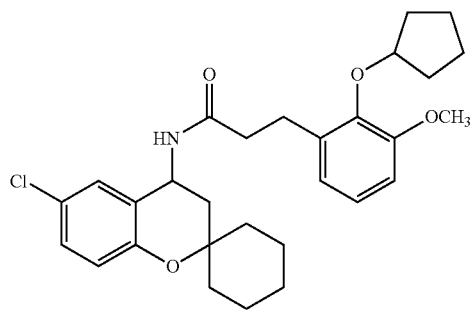 [SMILES: COc1cccc(CCC(=O)NC2CC3(CCCCC3)Oc3ccc(Cl)cc32)c1OC1CCCC1]

The title compound was prepared from Intermediate 17 (209 mg, 0.833 mmol) and 3-(2-cyclopentyloxy-3-methoxyphenyl)propanoic acid (200 mg, 0.758 mmol) in presence of EDCI.HCl (116 mg, 0.756 mmol), HOBt (218 mg, 1.137 mmol) and triethylamine (316 μl, 2.274 mmol) in dichloromethane (10 ml) as described in Example 1 to give 250 mg of the product as a white solid; IR (KBr) 3269, 2935, 1644, 1475, 1261, 1080, 970 cm$^{-1}$; $^1$H NMR (300 MHz, CDCl$_3$) δ 1.29-1.51 (m, 5H), 1.70-1.78 (m, 8H), 2.02-2.08 (m, 5H), 2.56-2.62 (m, 4H), 2.96 (t, J=6.0 Hz, 2H), 3.79 (s, 3H), 4.85 (br s, 1H), 5.14 (q, J=9.9 Hz, 1H), 5.71 (d, J=9.0 Hz, 1H), 6.69 (d, J=8.7 Hz, 1H), 6.77 (d, J=7.8 Hz, 2H), 6.93-7.04 (m, 3H); ESI-MS (m/z) 498.06 (M)$^+$.

Example 88

N-(2,2-Dimethyl-3,4-dihydro-2H-chromen-4-yl)-3-(2-cyclopentyloxy-3-methoxy)phenylpropanamide

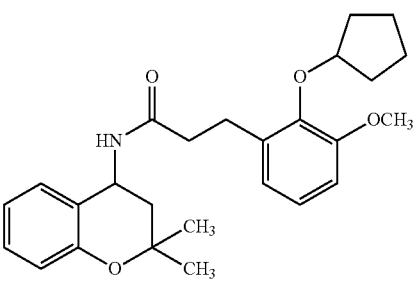 [SMILES: COc1cccc(CCC(=O)NC2CC(C)(C)Oc3ccccc32)c1OC1CCCC1]

The title compound was prepared from Intermediate 18 (200 mg, 1.129 mmol) and 3-(2-cyclopentyloxy-2-methoxyphenyl)propanoic acid (328 mg, 1.242 mmol) in presence of EDCI.HCl (324 mg, 1.671 mmol), HOBt (259 mg, 1.671 mmol) and triethylamine (471 μl, 3.383 mmol) in dichloromethane (10 ml) as described in Example 1 to give 187 mg of the product as a white solid; $^1$H NMR (300 MHz, CDCl$_3$) δ 1.27 (s, 3H), 1.36 (s, 3H), 1.48-1.79 (m, 8H), 2.02-2.10 (m, 1H), 2.55 (t, J=7.5 Hz, 2H), 2.92-2.99 (s, 2H), 3.80 (s, 3H), 4.80 (br s, 1H), 5.18 (q, J=9.9 Hz, 1H), 5.67 (d, J=8.7 Hz, 1H), 6.70-6.80 (m, 5H), 6.94 (t, J=8.1 Hz, 1H), 7.08 (t, J=7.2 Hz, 1H).

Example 89

N-(6-chloro-3,4-dihydro-2H-thiochromen-4-yl)-3-(2-cyclopentyloxy-3-methoxyphenyl)-propanamide

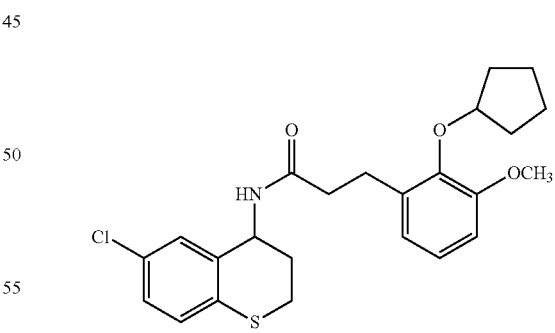

The title compound was prepared from Intermediate 19 (100 mg, 0.423 mmol) and 3-[2-(cyclopentyloxy)-3-methoxyphenyl]propanoic acid (134 mg, 0.508 mmol) in presence of EDCI.HCl (121 mg, 0.635 mmol), HOBt (97 mg, 0.635 mmol) and triethylamine (176 μl, 1.270 mmol) in dichloromethane (10 ml) as described in Example 1 to give 113 mg of the product as a white solid; $^1$H NMR (300 MHz, CDCl$_3$) δ 1.57-1.80 (m, 8H), 1.90-1.96 (m, 1H), 2.12-2.18 (m, 1H), 2.50-2.56 (m, 2H), 2.75-2.85 (m, 2H), 2.90-2.98 (m, 2H), 3.79 (s, 3H), 4.82 (br s, 1H), 5.02 (br s, 1H), 5.92 (br s, 1H), 6.72-6.80 (m, 2H), 6.91-6.98 (m, 3H), 7.03-7.10 (m, 1H).

Example 90

N-(6-chloro-3,4-dihydro-2H-thiochromen-4-yl)-3-(2-methoxy-1-naphthyl)propanamide

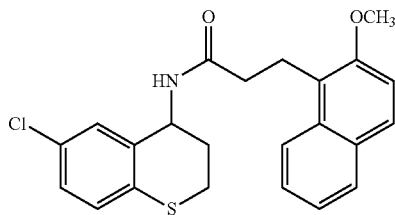 [SMILES: COc1ccc2ccccc2c1CCC(=O)NC1CCSc2ccc(Cl)cc21]

The title compound was prepared from Intermediate 19 (100 mg, 0.423 mmol) and 3-(2-methoxy-1-naphthyl)propanoic acid (146 mg, 0.508 mmol) in presence of EDCI.HCl (121 mg, 0.635 mmol), HOBt (97 mg, 0.635 mmol) and triethylamine (176 µl, 1.270 mmol) in dichloromethane (10 ml) as described in Example 1 to give 67 mg of the product as a white solid; $^1$H NMR (300 MHz, CDCl$_3$) δ 1.79-1.87 (m, 1H), 2.07-2.14 (m, 1H), 2.52-2.70 (m, 4H), 3.38-3.45 (m, 2H), 3.80 (s, 3H), 4.97 (br s, 1H), 5.95 (d, J=6.9 Hz, 1H), 6.92-6.98 (m, 2H), 7.04-7.10 (m, 1H), 7.16-7.21 (m, 1H), 7.33 (t, J=7.5 Hz, 1H), 7.48 (t, J=8.4 Hz, 1H), 7.75 (t, J=9.3 Hz, 2H), 7.95 (d, J=8.4 Hz, 1H).

Example 91

N-(6-Chloro-3,4-dihydrospiro[chromene-2,1'-cyclobutan]-4-yl)-4-(2-cyclopentyloxy-phenyl)butanamide

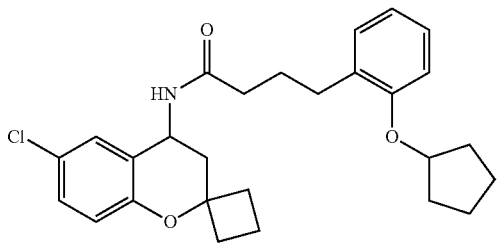 [SMILES: O=C(CCCc1ccccc1OC1CCCC1)NC1CC2(CCC2)Oc2ccc(Cl)cc21]

The title compound was prepared from Intermediate 2 (150 mg, 0.579 mmol) and 4-(2-cyclopentyloxyphenyl)butanoic acid (158 mg, 0.639 mmol) in presence of EDCI.HCl (166 mg, 0.863 mmol), HOBt (133 mg, 0.863 mmol) and triethylamine (241 µl, 2.043 mmol) in dichloromethane (5 ml) as described in Example 1 to give 153 mg of the product as a white solid; IR (KBr) 3300, 2943, 1646, 1474, 1238, 749 cm$^{-1}$; $^1$H NMR (300 MHz, CDCl$_3$) δ 1.70-2.00 (m, 12H), 2.24-2.41 (m, 7H), 2.64-2.70 (m, 2H), 3.47 (s, 1H), 4.75 (br s, 1H), 5.25 (d, J=6.0 Hz, 1H), 5.50 (d, J=6.9 Hz, 1H), 6.71 (d, J=8.4 Hz, 1H), 6.79-6.85 (m, 2H), 7.05-7.12 (m, 4H); ESI-MS (m/z) 454.30 (M)$^+$.

Example 92

N-(6-Chloro-3,4-dihydrospiro[chromene-2,1'-cyclobutan]-4-yl)-4-[2-(cyclopentyloxy)-3-methoxyphenyl]butanamide

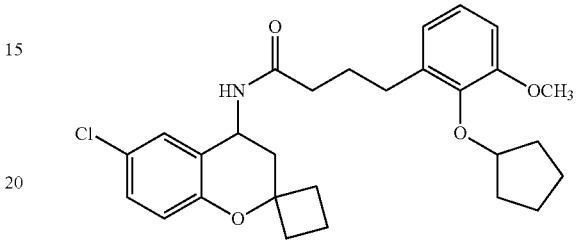

The title compound was prepared from Intermediate 2 (200 mg, 0.772 mmol) and 4-(2-cyclopentyloxy-3-methoxyphenyl)butanoic acid (214 mg, 0.772 mmol) in presence of EDCI.HCl (222 mg, 1.158 mmol), HOBt (118 mg, 0.772 mmol) and triethylamine (273 µl, 2.702 mmol) in dichloromethane (10 ml) as described in Example 1 to give 210 mg of the product as a white solid; IR (KBr) 3019, 2970, 1665, 1475, 1215, 769 cm$^{-1}$; $^1$H NMR (300 MHz, CDCl$_3$) δ 1.70-1.80 (m, 11H), 1.97-2.04 (m, 2H), 2.14-2.20 (m, 5H), 2.30-2.42 (m, 2H), 2.71 (t, J=6.9 Hz, 2H), 3.81 (s, 3H), 4.80 (br s, 1H), 5.24 (br s, 1H), 5.55 (d, J=8.7 Hz, 1H), 6.70-6.77 (m, 3H), 6.94 (t, J=7.2 Hz, 1H), 7.06 (d, J=9.9 Hz, 2H); ESI-MS (m/z) 482.44 (M−H)$^-$.

Example 93

N-(4R)-6-Chloro-3,4-dihydrospiro[chromene-2,1'-cyclobutan]-4-yl-4-(2-cyclopentyloxy-3-methoxyphenyl)butanamide

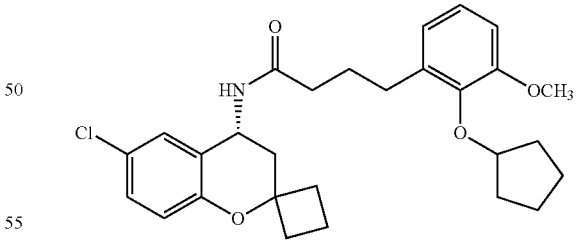

The title compound was prepared from Intermediate 8 (100 mg, 0.449 mmol) and 4-(2-cyclopentyloxy-3-methoxyphenyl)butanoic acid (124 mg, 0.449 mmol) in presence of EDCI.HCl (129 mg, 0.672 mmol), HOBt (69 mg, 0.450 mmol) and triethylamine (157 µl, 1.123 mmol) in dichloromethane (10 ml) as described in Example 1 to give 105 mg of the product as a white solid; IR (KBr) 3019, 2970, 1665, 1475, 1215, 769 cm$^{-1}$; $^1$H NMR (300 MHz, CDCl$_3$) δ 1.70-1.80 (m, 11H), 1.97-2.04 (m, 2H), 2.14-2.20 (m, 5H), 2.30-2.42 (m, 2H), 2.71 (t, J=6.9 Hz, 2H), 3.81 (s, 3H), 4.80 (br s, 1H), 5.24 (br s, 1H), 5.55 (d, J=8.7 Hz, 1H), 6.70-6.77 (m, 3H), 6.94 (t, J=7.2 Hz, 1H), 7.06 (d, J=9.9 Hz, 2H); ESI-MS (m/z) 482.44 (M−H)⁻.

Example 94

N-{(4S)-6-Chloro-3,4-dihydrospiro[chromene-2,1'-cyclobutan]-4-yl}-4-[(2-(cyclopentyl-oxy)-3-methoxyphenyl]butanamide

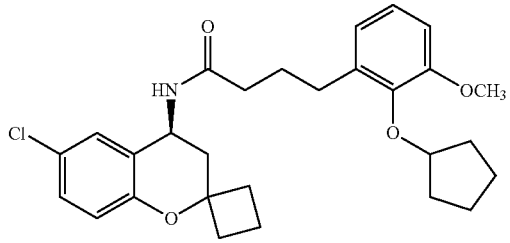 [SMILES: COc1cccc(CCCC(=O)N[C@H]2CC3(CCC3)Oc3ccc(Cl)cc32)c1OC1CCCC1]

The title compound was prepared from Intermediate 9 (100 mg, 0.449 mmol) and 4-(2-cyclopentyloxy-3-methoxyphenyl)butanoic acid (132 mg, 0.474 mmol) in presence of EDCI.HCl (129 mg, 0.672 mmol), HOBt (69 mg, 0.450 mmol) and triethylamine (157 μl, 1.123 mmol) in dichloromethane (10 ml) as described in Example 1 to give 140 mg of the product as a white solid; IR (KBr) 3019, 2970, 1665, 1475, 1215, 769 cm⁻¹; ¹H NMR (300 MHz, CDCl₃) δ 1.70-1.80 (m, 11H), 1.97-2.04 (m, 2H), 2.14-2.20 (m, 5H), 2.30-2.42 (m, 2H), 2.71 (t, J=6.9 Hz, 2H), 3.81 (s, 3H), 4.80 (br s, 1H), 5.24 (br s, 1H), 5.55 (d, J=8.7 Hz, 1H), 6.70-6.77 (m, 3H), 6.94 (t, J=7.2 Hz, 1H), 7.06 (d, J=9.9 Hz, 2H); ESI-MS (m/z) 482.44 (M−H)⁻.

Example 95

(4R)—N-(8-Chloro-3,4-dihydrospiro[chromene-2,1'-cyclobutan]-4-yl)-4-(2-cyclopentyloxy-3-methoxyphenyl)butanamide

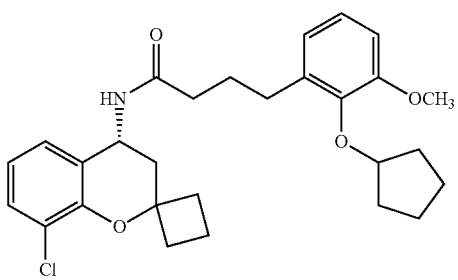 [SMILES: COc1cccc(CCCC(=O)N[C@@H]2CC3(CCC3)Oc3c(Cl)cccc32)c1OC1CCCC1]

The title compound was prepared from Intermediate 3 (150 mg, 0.619 mmol) and 4-(2-cyclopentyloxy-3-methoxyphenyl)butanoic acid (205 mg, 0.739 mmol) in presence of EDCI.HCl (193 mg, 1.012 mmol), HOBt (154 mg, 1.012 mmol) and triethylamine (279 μl, 2.043 mmol) in dichloromethane (10 ml) as described in Example 1 to give 149 mg of the product as a white solid; IR (KBr) 3315, 2945, 1642, 1438, 1244, 1040 cm⁻¹; ¹H NMR (300 MHz, CDCl₃) δ 1.57-1.70 (m, 10H), 1.97-2.04 (m, 4H), 2.14-2.20 (m, 4H), 2.40-2.47 (m, 2H), 2.66-2.72 (m, 2H), 3.80 (s, 3H), 4.79 (br s, 1H), 5.28 (d, J=6.3 Hz, 1H), 5.56 (d, J=8.4 Hz, 1H), 6.66-6.77 (m, 3H), 6.90-7.04 (m, 2H), 7.14-7.20 (m, 1H); ESI-MS (m/z) 484.26 (M)⁺.

Example 96

(4S)—N-(8-Chloro-3,4-dihydrospiro[chromene-2,1'-cyclobutan]-4-yl)-4-(2-cyclopentyloxy-3-methoxyphenyl)butanamide

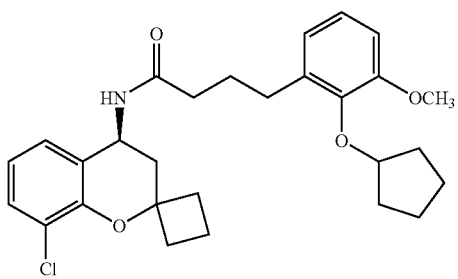 [SMILES: COc1cccc(CCCC(=O)N[C@H]2CC3(CCC3)Oc3c(Cl)cccc32)c1OC1CCCC1]

The title compound was prepared from Intermediate 4 (150 mg, 0.619 mmol) and 4-(2-cyclopentyloxy-3-methoxyphenyl)butanoic acid (205 mg, 0.739 mmol) in presence of EDCI.HCl (193 mg, 1.012 mmol), HOBt (154 mg, 1.012 mmol) and triethylamine (279 μl, 2.043 mmol) in dichloromethane (10 ml) as described in Example 1 to give 153 mg of the product as a white solid; IR (KBr) 3316, 2946, 1642, 1538, 1451, 1084 cm⁻¹; ¹H NMR (300 MHz, CDCl₃) δ 1.70-1.80 (m, 10H), 1.97-2.04 (m, 4H), 2.05-2.12 (m, 4H), 2.39-2.49 (m, 2H), 2.70 (t, J=7.2 Hz, 2H), 3.81 (s, 3H), 4.80 (br s, 1H), 5.29 (q, J=6.3 Hz, 1H), 5.55 (d, J=7.5 Hz, 1H), 6.76-6.79 (m, 3H), 6.91-7.05 (m, 4H), 7.20 (s, 1H); ESI-MS (m/z) 484.21 (M)⁺.

Example 97

N-(8-Chloro-6-fluoro-3,4-dihydrospiro[chromene-2,1'-cyclobutan]-4-yl)-4-(2-cyclopentyl oxy-3-methoxyphenyl)butanamide

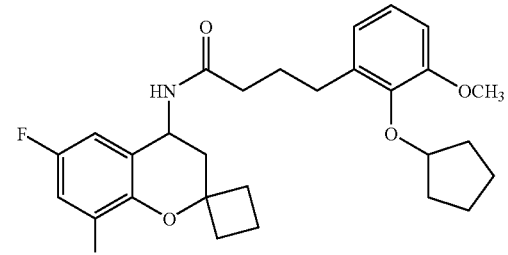

The title compound was prepared from Intermediate 20 (200 mg, 0.719 mmol) and 4-(2-cyclopentyloxy-3-methoxyphenyl)butanoic acid (200 mg, 0.719 mmol) in presence of EDCI.HCl (207 mg, 1.079 mmol), HOBt (110 mg, 0.719 mmol) and triethylamine (250 μl, 1.798 mmol) in dichloromethane (10 ml) as described in Example 1 to give 105 mg of the product as a white solid; IR (KBr) 3313, 2956, 1645, 1463, 1214, 1083, 742 cm⁻¹; ¹H NMR (300 MHz, CDCl₃) δ 1.65-1.79 (m, 9H), 1.99-2.05 (m, 4H), 2.08-2.18 (m, 5H), 2.38-2.43 (m, 2H), 2.71 (t, J=6.3 Hz, 2H), 3.81 (s, 3H), 4.80

(br s, 1H), 5.27 (q, J=6.6 Hz, 1H), 5.54 (d, J=7.8 Hz, 1H), 6.66-6.75 (m, 3H), 6.91-6.96 (m, 2H); ESI-MS (m/z) 500.38 (M–H)⁻.

Example 98

N-(6,8-Dichloro-3,4-dihydrospiro[chromene-2,1'-cyclobutan]-4-yl)-4-(2-cyclopentyloxy-3-methoxyphenyl)butanamide

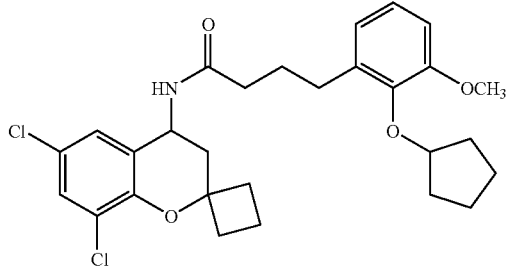 [SMILES: COc1cccc(CCCC(=O)NC2CC3(CCC3)Oc3c(Cl)cc(Cl)cc32)c1OC1CCCC1]

The title compound was prepared from Intermediate 13 (150 mg, 0.511 mmol) and 4-(2-cyclopentyloxy-3-methoxyphenyl)butanoic acid (142 mg, 0.511 mmol) in presence of EDCI.HCl (147 mg, 0.766 mmol), HOBt (78 mg, 0.511 mmol) and triethylamine (178 μl, 1.277 mmol) in dichloromethane (10 ml) as described in Example 1 to give 105 mg of the product as a white solid; IR (KBr) 3283, 2954, 1644, 1451, 1220, 1083 cm⁻¹; ¹H NMR (300 MHz, CDCl₃) δ 1.72-1.82 (m, 10H), 1.97-2.01 (m, 3H), 2.12-2.20 (m, 5H), 2.36-2.42 (m, 2H), 2.71 (t, J=6.6 Hz, 2H), 3.80 (s, 3H), 4.80 (br s, 1H), 5.24 (q, J=6.3 Hz, 1H), 5.53 (d, J=7.8 Hz, 1H), 6.72-6.78 (m, 2H), 6.91-6.96 (m, 1H), 7.01 (s, 1H), 7.20 (s, 1H); ESI-MS (m/z) 518.17 (M)⁺.

Example 99

N-(7-Benzyloxy-3,4-dihydrospiro[chromene-2,1'-cyclobutan]-4-yl)-4-(2-cyclopentyloxy-3-methoxyphenyl)butanamide

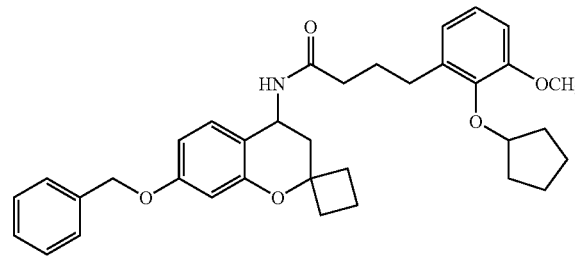

The title compound was prepared from Intermediate 12 (200 mg, 0.603 mmol) and 3-(2-cyclopentyloxy-3-methoxyphenyl)butanoic acid (167 mg, 0.603 mmol) in presence of EDCI.HCl (173 mg, 0.904 mmol), HOBt (138 mg, 0.904 mmol) and triethylamine (335 μl, 2.413 mmol) in dichloromethane (10 ml) as described in Example 1 to give 156 mg of the product as a white solid; IR (KBr) 3254, 2960, 1639, 1269, 1134, 1019 cm⁻¹; ¹H NMR (300 MHz, CDCl₃) δ 1.68-1.81 (m, 11H), 1.97-2.02 (m, 4H), 2.18-2.25 (m, 4H), 2.32-2.37 (m, 2H), 2.69 (t, J=7.2 Hz, 2H), 3.81 (s, 3H), 4.79 (br s, 1H), 4.99 (s, 2H), 5.17 (q, J=6.0 Hz, 1H), 5.49 (d, J=8.1 Hz, 1H), 6.41 (s, 1H), 6.50 (d, J=8.7 Hz, 1H), 6.62-6.74 (m, 2H), 6.96-7.04 (m, 2H), 7.29-7.37 (m, 4H); ESI-MS (m/z) 554.40 (M–H)⁻.

Example 100

N-(7-Hydroxy-3,4-dihydrospiro[chromene-2,1'-cyclobutan]-4-yl)-4-(2-cyclopentyloxy-3-methoxyphenyl)butanamide

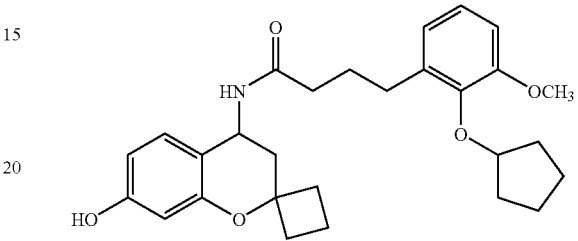

The title compound was prepared by the debenzylation of Example 99 (100 mg, 0.181 mmol) accomplished by 10% Pd/C (30 mg) in methanol (10 ml) at 50 psi pressure for 2 h under nitrogen as described in Example 17, Step 2 to give 53 mg of the product as a white solid; IR (KBr) 3254, 2960, 1639, 1474, 1134, 1019 cm⁻¹; ¹H NMR (300 MHz, CDCl₃) δ 1.25-1.32 (m, 3H), 1.62-1.72 (m, 4H), 1.78-1.85 (m, 5H), 1.94-1.99 (m, 2H), 2.12-2.17 (m, 4H), 2.26-2.35 (m, 2H), 2.69 (t, J=6.9 Hz, 2H), 3.81 (s, 3H), 4.79 (br s, 1H), 5.15 (q, J=5.7 Hz, 1H), 5.52 (d, J=8.4 Hz, 2H), 6.26-6.34 (m, 2H), 6.72-6.76 (m, 2H), 6.91-6.96 (m, 2H); ESI-MS (m/z) 554.40 (M–H)⁻.

Example 101

N-(6-Chloro-3,4-dihydrospiro[chromene-2,1'-cyclobutan]-4-yl)-4-oxo-4-(4-methoxy-naphthyl)butanamide

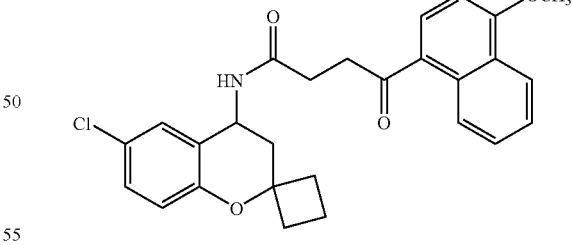

The title compound was prepared from Intermediate 2 (250 mg, 0.965 mmol) and 4-(4-methoxy-1-naphthyl)-4-oxobutanoic acid (274 mg, 1.062 mmol) in presence of EDCI.HCl (277 mg, 1.451 mmol), HOBt (221 mg, 1.459 mmol) and triethylamine (403 μl, 2.905 mmol) in dichloromethane (10 ml) as described in Example 1 to give 311 mg of the product as a white solid; IR (KBr) 3204, 2972, 1632, 1523, 1230, 757 cm⁻¹; ¹H NMR (300 MHz, CDCl₃) δ 1.67-1.73 (m, 2H), 2.06-2.31 (m, 6H), 2.66-2.71 (m, 2H), 3.31-3.39 (m, 2H), 4.05 (s, 3H), 5.05 (br s, 1H), 6.77 (d, J=9.0 Hz, 1H), 7.03 (d, J=8.4 Hz, 1H), 7.14 (d, J=8.4 Hz, 1H), 7.20 (s, 1H), 7.53-7.61

(m, 2H), 8.20-8.28 (m, 2H), 8.43 (d, J=8.4 Hz, 1H), 8.86 (d, J=8.7 Hz, 1H); ESI-MS (m/z) 464.17 (M+H)+.

Example 102

N-(6-Chloro-3,4-dihydrospiro[chromene-2,1'-cyclobutan]-4-yl)-4-hydroxy-4-(4-methoxy naphthyl)butanamide

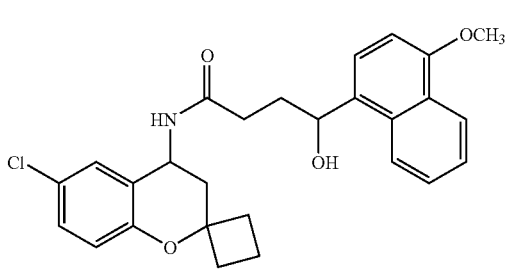 [SMILES: COc1ccc(C(O)CCC(=O)NC2CC3(CCC3)Oc3ccc(Cl)cc32)c2ccccc12]

The title compound was prepared by the reduction of Example 101 (200 mg, 0.431 mmol) using sodium borohydride (932 mg, 0.864 mmol) in tetrahydrofuran (10 ml) and methanol (5 ml) at 0° C. for 3 h. The reaction mixture was allowed to warm to room temperature and concentrated to give 31 mg of the product as a white solid; $^1$H NMR (300 MHz, CDCl$_3$) δ 1.67-1.76 (m, 3H), 2.02-2.09 (m, 3H), 2.25-2.42 (m, 7H), 3.35 (br s, 1H), 3.89 (s, 3H), 5.14 (br s, 1H), 5.36 (br s, 1H), 6.61-6.73 (m, 2H), 6.96-7.05 (m, 2H), 7.34-7.41 (m, 2H), 7.42-7.55 (m, 1H), 7.96 (br s, 1H), 8.17 (d, J=8.7 Hz, 1H).

Example 103

N-(6-Chloro-2,2-dimethyl-3,4-dihydro-2H-chromen-4-yl)-4-(2-cyclopentyloxy-3-methoxy)phenylbutanamide

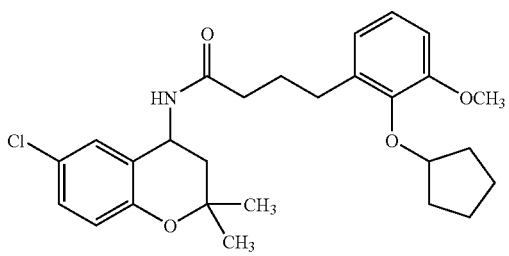 [SMILES: COc1cccc(CCCC(=O)NC2CC(C)(C)Oc3ccc(Cl)cc32)c1OC1CCCC1]

The title compound was prepared from Intermediate 21 (200 mg, 0.941 mmol) and 4-(2-cyclopentyloxy-3-methoxyphenyl)butanoic acid (261 mg, 0.941 mmol) in presence of EDCI.HCl (270 mg, 1.411 mmol), HOBt (144 mg, 0.941 mmol) and triethylamine (328 μl, 2.352 mmol) in dichloromethane (10 ml) as described in Example 1 to give 173 mg of the product as a white solid; IR (KBr) 3302, 2958, 1645, 1475, 1261, 1085 cm$^{-1}$; $^1$H NMR (300 MHz, CDCl$_3$) δ 1.29 (s, 3H), 1.39 (s, 3H), 1.71-1.79 (m, 8H), 1.95-2.02 (m, 2H), 2.12-2.20 (m, 3H), 2.70 (t, J=6.6 Hz, 3H), 3.81 (s, 3H), 4.80 (br s, 1H), 5.25 (q, J=6.3 Hz, 1H), 5.51 (d, J=7.8 Hz, 1H), 6.67-6.77 (m, 3H), 6.90-6.97 (m, 1H), 7.05-7.13 (m, 2H); ESI-MS (m/z) 472.32 (M+H)+.

Example 104

N-(6-chloro-3,4-dihydro-2H-thiochromen-4-yl)-4-(2-cyclopentyloxy-3-methoxyphenyl)-butanamide

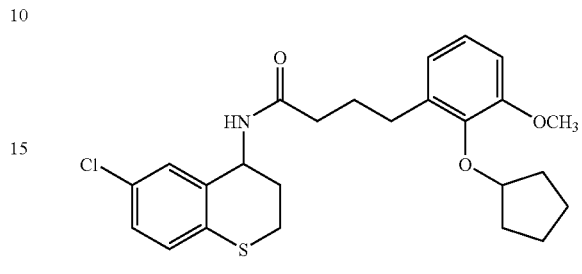

The title compound was prepared from Intermediate 19 (100 mg, 0.423 mmol) and 4-(2-cyclopentyloxy-3-methoxyphenyl)butanoic acid (141 mg, 0.508 mmol) in presence of EDCI.HCl (121 mg, 0.635 mmol), HOBt (97 mg, 0.635 mmol) and triethylamine (176 μl, 1.270 mmol) in dichloromethane (10 ml) as described in Example 1 to give 87 mg of the product as a white solid; $^1$H NMR (300 MHz, CDCl$_3$) δ 1.58-1.68 (m, 4H), 1.75-1.85 (m, 4H), 1.90-2.00 (m, 2H), 2.10-2.20 (m, 4H), 2.63-2.70 (m, 2H), 2.95-3.01 (m, 2H), 3.81 (s, 3H), 4.79 (br s, 1H), 5.13 (br s, 1H), 5.60-5.66 (m, 1H), 6.72 (d, J=7.2 Hz, 2H), 6.92 (t, J=7.8 Hz, 1H), 7.00-7.09 (m, 2H), 7.17 (s, 1H).

Pharmacological Activity

The illustrative examples of the present invention are screened for TRPV3 activity according to a modified procedure described in Toth, A. et al. *Life Sciences* (2003), 73, 487-498. The screening of the compounds can be carried out by other methods and procedures known to a person skilled in the art. Such screening methods may be found in Hu, H-Z., et al. *J. Biol. Chem.* (2004), 279, 35741-35748; Smith, G. D et al. *Nature* (2002), 418, 186-190 and Peier, A. M., et al. *Science* (2002), 296, 2046-2049.

Screening for TRPV3 Antagonist Using the $^{45}$Calcium Uptake Assay:

The inhibition of TRPV3 receptor activation was followed as inhibition of 2-APB induced cellular uptake of radioactive calcium. Test compounds were dissolved in DMSO to prepare 20 mM stock and then diluted using plain medium with 0.1% BSA and 1.8 mM CaCl$_2$ to get desired concentration. Final concentration of DMSO in the reaction was 0.5% (v/v). Human TRPV3 expressing CHO cells were grown in F-12 DMEM medium with 10% FBS, 1% penicillin-streptomycin solution, 400 μg/ml of G-418. Cells were seeded 24 h prior to the assay in 96 well plates so as to get ~50,000 cells per well on the day of experiment. Cells were treated with test compounds for 10 minutes followed by addition of 2-APB at a final concentration of 500 μM and 5 μCi/ml $^{45}$Ca$^{+2}$ for 4 minutes. Cells were washed and lysed using buffer containing 1% Triton X-100, 0.1% deoxycholate and 0.1% SDS. Radioactivity in the lysate was measured in Packardt Top count after addition of liquid scintillant.

Concentration response curves were plotted as a % of maximal response obtained in the absence of test antagonist.

$IC_{50}$ value was calculated from concentration response curve by nonlinear regression analysis using GraphPad PRISM software.

The compounds prepared were tested using the above assay procedure and the results obtained are given in Table 2. Percentage inhibition at concentrations of 1.0 μM and 10.0 μM are given in the table along with $IC_{50}$ (nM) values for selected examples.

The $IC_{50}$ (nM) values of the compounds are set forth in Table 2 wherein "A" refers to an $IC_{50}$ value of less than 500 nM, "B" refers to $IC_{50}$ value in range of 500.0 to 1000.0 nM, "C" refers to an $IC_{50}$ value in range of 1000.01 to 2000.0 nM and "D" refers to an $IC_{50}$ value of more than 2000.0 nM,

TABLE 2

In-vitro screening results of compounds of invention:

| Example No. | Percentage inhibition at 1.0 μM | at 10.0 μM | $IC_{50}$ value (nM) |
|---|---|---|---|
| Example 1 | 1.7 | 10.0 | — |
| Example 2 | 12.0 | 79.0 | D |
| Example 3 | 0.0 | 33.1 | — |
| Example 4 | 37.2 | 66.2 | — |
| Example 5 | 11.7 | 86.8 | — |
| Example 6 | 35.3 | 89.0 | — |
| Example 7 | 9.2 | 20.3 | — |
| Example 8 | 3.8 | 22.5 | — |
| Example 9 | 11.7 | 68.5 | — |
| Example 10 | 13.7 | 92.4 | — |
| Example 11 | 23.6 | 76.0 | — |
| Example 12 | — | — | B |
| Example 13 | 5.9 | 87.6 | C |
| Example 14 | 9.8 | 78.8 | — |
| Example 15 | — | 27.3 | — |
| Example 16 | 0.0 | 35.2 | — |
| Example 17 | 21.9 | 70.0 | — |
| Example 18 | 36.1 | 72.3 | — |
| Example 19 | 23.1 | 61.7 | — |
| Example 20 | 19.3 | 50.9 | — |
| Example 21 | 63.5 | 93.6 | B |
| Example 22 | 35.3 | 72.1 | — |
| Example 23 | 6.2 | 65.3 | — |
| Example 24 | 26.9 | 89.9 | C |
| Example 25 | 19.0 | 48.0 | — |
| Example 26 | 29.4 | 46.1 | — |
| Example 27 | 5.3 | 75.9 | — |
| Example 28 | 58.0 | 84.3 | — |
| Example 29 | 43.6 | 88.4 | — |
| Example 30 | 46.8 | 80.6 | — |
| Example 31 | 78.6 | 97.4 | B |
| Example 32 | 24.8 | 43.9 | — |
| Example 33 | 13.5 | 33.9 | — |
| Example 34 | 5.69 | 77.1 | — |
| Example 35 | 44.8 | 97.6 | — |
| Example 36 | 55.5 | 96.8 | — |
| Example 37 | 46.3 | 95.7 | B |
| Example 38 | 23.8 | 82.7 | — |
| Example 39 | 73.8 | 97.5 | B |
| Example 40 | 6.8 | 93.5 | — |
| Example 41 | 49.0 | 96.4 | B |
| Example 42 | 47.2 | 95.1 | B |
| Example 43 | 64.6 | 91.7 | B |
| Example 44 | 50.8 | 88.8 | — |
| Example 45 | 59.2 | 94.8 | B |
| Example 46 | 53.2 | 99.7 | B |
| Example 47 | — | — | A |
| Example 48 | — | — | B |
| Example 49 | 35.4 | 70.1 | — |
| Example 50 | 52.8 | 77.6 | B |
| Example 51 | 37.1 | 86.7 | C |
| Example 52 | 39.6 | 92.5 | — |
| Example 53 | 61.9 | 91.4 | B |
| Example 54 | 36.2 | 63.6 | — |
| Example 55 | — | — | — |
| Example 56 | 57.5 | 87.5 | — |

TABLE 2-continued

In-vitro screening results of compounds of invention:

| Example No. | Percentage inhibition at 1.0 μM | at 10.0 μM | $IC_{50}$ value (nM) |
|---|---|---|---|
| Example 57 | 30.3 | 84.3 | — |
| Example 58 | 61.7 | 98.7 | — |
| Example 59 | 89.4 | 96.3 | A |
| Example 60 | 1.2 | 0.0 | — |
| Example 61 | 45.1 | 93.8 | — |
| Example 62 | 13.5 | 82.2 | — |
| Example 63 | 73.3 | 97.0 | — |
| Example 64 | 37.6 | 95.4 | — |
| Example 65 | 74.1 | 99.5 | B |
| Example 66 | 44.6 | 92.3 | — |
| Example 67 | 17.0 | 84.7 | — |
| Example 68 | 70.6 | 91.0 | B |
| Example 69 | 40.3 | 86.8 | — |
| Example 70 | 66.1 | 91.2 | B |
| Example 71 | 53.5 | 95.5 | — |
| Example 72 | 60.3 | 93.3 | B |
| Example 73 | 61.3 | 83.3 | B |
| Example 74 | 64.1 | 90.4 | C |
| Example 75 | 46.6 | 90.4 | — |
| Example 76 | 23.5 | 58.8 | — |
| Example 77 | 39.4 | 81.8 | — |
| Example 78 | 46.1 | 91.3 | B |
| Example 79 | 51.5 | 95.5 | — |
| Example 80 | 73.52 | 98.6 | B |
| Example 81 | 29.1 | 54.8 | — |
| Example 82 | 24.3 | 90.9 | — |
| Example 83 | 11.0 | 83.2 | — |
| Example 84 | 11.0 | 83.2 | — |
| Example 85 | 76.9 | 90.4 | A |
| Example 86 | 11.6 | 66.0 | — |
| Example 87 | 26.7 | 67.3 | — |
| Example 88 | 17.1 | 93.2 | — |
| Example 89 | 38.0 | 87.3 | — |
| Example 90 | 49.2 | 91.4 | — |
| Example 91 | 51.0 | 82.5 | — |
| Example 92 | 86.1 | 95.8 | A |
| Example 93 | 72.8 | 94.2 | B |
| Example 94 | 79.7 | 97.2 | A |
| Example 95 | 71.8 | 96.5 | B |
| Example 96 | 44.4 | 80.9 | — |
| Example 97 | 60.0 | 90.3 | C |
| Example 98 | 36.9 | 69.5 | — |
| Example 99 | 19.9 | 19.6 | — |
| Example 100 | 19.4 | 87.0 | — |
| Example 101 | 26.5 | 63.2 | — |
| Example 102 | 26.6 | 42.8 | — |
| Example 103 | 69.4 | 96.4 | B |
| Example 104 | 51.3 | 92.5 | — |

The invention claimed is:

1. A compound of formula (I):

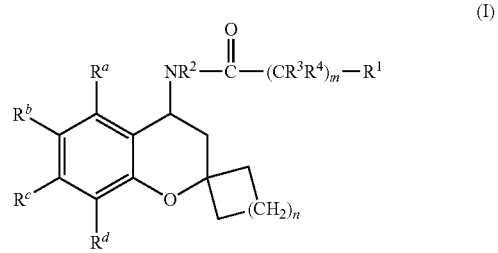

wherein, $R^1$ is selected from substituted or unsubstituted aryl, substituted or unsubstituted heteroaryl, substituted or unsubstituted heterocyclic group or substituted or unsubstituted cycloalkyl; in which aryl, heteroaryl and heterocyclic ring are mono, bi or tricyclic; and fully or partially aromatic;

wherein substituents on aryl, heteroaryl, heterocyclic ring and cycloalkyl are independently selected from the group consisting of halogen, hydroxy, nitro, cyano, substituted or unsubstituted amino, substituted or unsubstituted alkyl, linear or branched chain alkyl, linear or branched chain alkoxy, substituted or unsubstituted alkenyl, substituted or unsubstituted alkoxy, substituted or unsubstituted haloalkyl, fully or partially substituted haloalkyl, substituted or unsubstituted haloalkyloxy, fully or partially substituted haloalkyloxy, substituted or unsubstituted cycloalkyl, substituted or unsubstituted cycloalkoxy, substituted or unsubstituted cycloalkylalkyl, substituted or unsubstituted cycloalkylalkoxy, substituted or unsubstituted aryl, substituted or unsubstituted aryloxy, substituted or unsubstituted arylalkyl, substituted or unsubstituted arylalkoxy, substituted or unsubstituted heterocyclic group, substituted or unsubstituted heteroaryl, —S(O)$_p$R$^a$, —NHS(O)$_p$R$^a$, —O(CH$_2$)$_m$NR$^a$R$^b$, —C(O)—R$^a$ or —C(O)NR$^a$R$^b$;

R$^2$ is selected from the group consisting of hydrogen, substituted or unsubstituted alkyl, substituted or unsubstituted cycloalkyl, substituted or unsubstituted aryl, substituted or unsubstituted arylalkyl, substituted or unsubstituted heteroaryl, or substituted or unsubstituted heterocyclic group;

each occurrence of R$^a$, R$^b$, R$^c$ and R$^d$ are independently selected from hydrogen, nitro, cyano, halogen, —OR$^e$, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclic group;

R$^e$ is selected from the group consisting of hydrogen, substituted or unsubstituted alkyl, substituted or unsubstituted alkenyl, substituted or unsubstituted cycloalkyl, substituted or unsubstituted aryl, substituted or unsubstituted heteroaryl, or substituted or unsubstituted heterocyclic group;

R$^3$ and R$^4$ are independently selected from hydrogen, halogen, substituted or unsubstituted amino, substituted or unsubstituted alkyl, linear or branched chain alkyl, linear or branched chain alkoxy, substituted or unsubstituted alkenyl, substituted or unsubstituted alkoxy, substituted or unsubstituted haloalkyl, fully or partially substituted haloalkyl, substituted or unsubstituted haloalkyloxy, fully or partially substituted haloalkyloxy, substituted or unsubstituted cycloalkyl, substituted or unsubstituted cycloalkoxy, substituted or unsubstituted cycloalkylalkyl, substituted or unsubstituted cycloalkylalkoxy, substituted or unsubstituted aryl;

'm' is an integer selected from 1 to 4;

'n' is an integer selected from 0 to 3;

'p' is an integer selected from 0 to 2;

or a tautomer, regiomer, stereoisomer, enantiomer, diastereomer or pharmaceutically acceptable salt thereof, with proviso that R$^b$ is not a group selected from —OR$^e$, —NR$^3$R$^4$ or C(O)NR$^3$R$^4$.

2. The compound according to claim 1, as represented by formula (II):

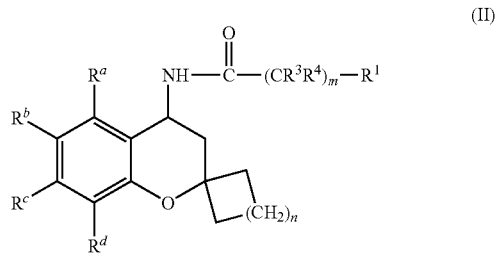

wherein,

R$^1$ is selected from substituted or unsubstituted aryl, substituted or unsubstituted heteroaryl, substituted or unsubstituted heterocyclic group or substituted or unsubstituted cycloalkyl; in which aryl, heteroaryl and heterocyclic ring are mono, bi or tricyclic; and fully or partially aromatic;

wherein substituents on aryl, heteroaryl, heterocyclic ring and cycloalkyl are independently selected from the group consisting of halogen, hydroxyl, nitro, cyano, amino, substituted or unsubstituted alkyl, linear or branched chain alkyl, linear or branched chain alkoxy, substituted or unsubstituted alkenyl, substituted or unsubstituted alkoxy, substituted or unsubstituted haloalkyl, fully or partially substituted haloalkyl, substituted or unsubstituted haloalkyloxy, fully or partially substituted haloalkyloxy, substituted or unsubstituted cycloalkyl, substituted or unsubstituted cycloalkoxy, substituted or unsubstituted cycloalkylalkyl, substituted or unsubstituted cycloalkylalkoxy, substituted or unsubstituted aryl, substituted or unsubstituted aryloxy, substituted or unsubstituted arylalkyl, substituted or unsubstituted arylalkoxy, substituted or unsubstituted heterocyclic group, substituted or unsubstituted heteroaryl, —S(O)$_p$R$^a$, —NHS(O)$_p$R$^a$, —O(CH$_2$)$_m$NR$^a$R$^b$, —C(O)—R$^a$ or —C(O)NR$^a$R$^b$;

each occurrence of R$^a$, R$^b$, R$^c$ and R$^d$ are independently selected from hydrogen, nitro, cyano, halogen, —OR$^e$, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclic group;

R$^e$ is selected from the group consisting of hydrogen, substituted or unsubstituted alkyl, substituted or unsubstituted alkenyl, substituted or unsubstituted cycloalkyl, substituted or unsubstituted aryl, substituted or unsubstituted heteroaryl, or substituted or unsubstituted heterocyclic group;

R$^3$ and R$^4$ are independently selected from hydrogen, halogen, substituted or unsubstituted amino, substituted or unsubstituted alkyl, linear or branched chain alkyl, linear or branched chain alkoxy, substituted or unsubstituted alkenyl, substituted or unsubstituted alkoxy, substituted or unsubstituted haloalkyl, fully or partially substituted haloalkyl, substituted or unsubstituted haloalkyloxy, fully or partially substituted haloalkyloxy, substituted or unsubstituted cycloalkyl, substituted or unsubstituted cycloalkoxy, substituted or unsubstituted cycloalkylalkyl, substituted or unsubstituted cycloalkylalkoxy, substituted or unsubstituted aryl;

'm' is an integer selected from 1 to 4;
'n' is an integer selected from 0 to 3;
'p' is an integer selected from 0 to 2;
or a tautomer, regiomer, stereoisomer, enantiomer, diastereomer or pharmaceutically acceptable salt thereof, with proviso that $R^b$ is not a group selected from $-OR^e$, $-NR^3R^4$ or $C(O)NR^3R^4$.

3. The compound according to claim 1, wherein $R^3$ and $R^4$ are hydrogen.

4. The compound according to claim 1, wherein one of $R^3$ and $R^4$ is hydrogen and the other is hydroxy or alkyl (methyl).

5. The compound according to claim 1, wherein 'm' is an integer 1.

6. The compound according to claim 1, wherein 'm' is an integer 2.

7. The compound according to claim 1, wherein 'm' is an integer 3.

8. The compound according to claim 1, wherein 'n' is integer 1 in order to make 4 member ring.

9. The compound according to claim 1, wherein 'n' is integer 2 in order to make 5 member ring.

10. The compound according to claim 1 wherein 'n' is integer 3 in order to make 6 member ring.

11. The compound according to claim 1, wherein $R^2$ is hydrogen.

12. The compound according to claim 1, wherein $R^a$, $R^b$, $R^c$ and $R^d$ are selected from hydrogen or halogen.

13. The compound according to claim 12, wherein halogen is fluorine or chlorine.

14. The compound according to claim 1, wherein $R^a$, $R^c$ and $R^d$ are selected from hydrogen, hydroxy, alkyl, alkoxy or arylalkoxy.

15. The compound according to claim 14, wherein alkyl is methyl.

16. The compound according to claim 14, wherein alkoxy is methoxy.

17. The compound according to claim 14, wherein arylalkoxy is benzyloxy.

18. The compound according to claim 1, wherein $R^1$ is substituted or unsubstituted aryl, wherein aryl is fully or partially aromatic or substituted or unsubstituted heteroaryl.

19. The compound according to claim 18, wherein aryl is substituted phenyl.

20. The compound according to claim 18, wherein aryl is phenyl.

21. The compound according to claim 18, wherein aryl is substituted or unsubstituted naphthyl.

22. The compound according to claim 18, wherein aryl is partially aromatic.

23. The compound according to claim 22, wherein aryl is tetrahydronaphthalene.

24. The compound according to claim 18, wherein heteroaryl is mono, bi or tricyclic.

25. The compound according to claim 24, wherein monocyclic heteroaryl is pyridine.

26. The compound according to claim 24, wherein bicyclic heteroaryl is indole, benzodioxole, benzisoxazole, benzofuran, quinoline or benzodioxine.

27. The compound according to claim 24, wherein tricyclic heteroaryl is dibenzofuran.

28. The compound according to claim 18, wherein substituents comprising of hydroxy, halogen, alkyl, alkoxy, haloalkoxy, cycloalkoxy, cycloalkylalkoxy, arylalkoxy, alkylsulfonylamino, alkylaminoalkoxy or heteroaryl.

29. The compound according to claim 28, wherein halogen is fluorine or chlorine, bromine or iodine.

30. The compound according to claim 28, wherein alkyl is methyl.

31. The compound according to claim 28, wherein alkoxy is methoxy, ethoxy, n-propoxy, n-butoxy or iso-propoxy.

32. The compound according to claim 28, wherein haloalkoxy fully or partially substituted.

33. The compound according to claim 32, wherein partially substituted haloalkoxy is $OCHF_2$.

34. The compound according to claim 28, wherein cycloalkyloxy is cyclopentyloxy.

35. The compound according to claim 28, wherein cycloalkylalkoxy is cyclopropylmethoxy.

36. The compound according to claim 28, wherein heteroaryl is pyridine.

37. The compound according to claim 28, wherein arylalkyloxy is benzyloxy.

38. The compound according to claim 28, wherein alkylsulfonylamino is $-NHS(O)_2CH_3$ or $NHS(O)_2CH(CH_3)_2$.

39. The compound according to claim 28, wherein alkylaminoalkoxy is $-OCH_2CH_2N(CH_3)_2$.

40. The compound according to claim 1, selected from the group consisting of,
N-(8-Chloro-3,4-dihydrospiro[chromene-2,1'-cyclobutan]-4-yl)-2-phenylacetamide,
N-(6-Chloro-3,4-dihydrospiro[chromene-2,1'-cyclobutan]-4-yl)-2-(2-methoxyphenyl)acetamide,
N-(6-chloro-3,4-dihydrospiro[chromene-2,1'-cyclobutan]-4-yl)-2-{2-[(methylsulfonyl)amino]phenyl}acetamide,
N-(6-Chloro-3,4-dihydrospiro[chromene-2,1'-cyclobutan]-4-yl)-2-(2-(cyclopentyloxy)-3-methoxyphenyl)acetamide,
N-[(4R)-8-Chloro-3,4-dihydrospiro[chromene-2,1'-cyclobutan]-4-yl]-2-(2-cyclopentyloxy-3-methoxy)phenylacetamide,
N-[(4S)-8-Chloro-3,4-dihydrospiro[chromene-2,1'-cyclobutan]-4-yl]-2-(2-cyclopentyloxy-3-methoxy)phenylacetamide,
N-(6-Chloro-3,4-dihydrospiro[chromene-2,1'-cyclobutan]-4-yl)-2-(3,4-dimethoxyphenyl)acetamide,
N-(6-Chloro-3,4-dihydrospiro[chromene-2,1'-cyclobutan]-4-yl)-2-pyridin-2-ylacetamide,
N-(3,4-Dihydrospiro[chromene-2,1'-cyclobutan]-4-yl)-2-(1-naphthyl)acetamide,
N-(6-Fluoro-(3,4-dihydrospiro[chromene-2,1'-cyclobutan]-4-yl)-2-(1-naphthyl)acetamide,
N-[(4R)-6,8-Difluoro-3,4-dihydrospiro[chromene-2,1'-cyclobutan]-4-yl]-2-(1-naphthyl)acetamide,
N-[(4R)-6-Chloro-3,4-dihydrospiro[chromene-2,1'-cyclobutan]-4-yl]-2-(1-naphthyl)acetamide,
N-[(4S)-6-Chloro-3,4-dihydrospiro[chromene-2,1'-cyclobutan]-4-yl]-2-(1-naphthyl)acetamide,
N-(7-Chloro-3,4-dihydrospiro[chromene-2,1'-cyclobutan]-4-yl)-2-(1-naphthyl)acetamide,
N-[(4R)-8-Chloro-3,4-dihydrospiro[chromene-2,1'-cyclobutan]-4-yl]-2-(1-naphthyl)acetamide,
N-[(4S)-8-Chloro-3,4-dihydrospiro[chromene-2,1'-cyclobutan]-4-yl]-2-(1-naphthyl)acetamide,
N-(5-Hydroxy-3,4-dihydrospiro[chromene-2,1'-cyclobutan]-4-yl)-2-(1-naphthyl)acetamide,
N-(6-Chloro-3,4-dihydrospiro[chromene-2,1'-cyclobutan]-4-yl)-2-(2-naphthyl)acetamide,
(2S)—N-[(4R)-6-Chloro-3,4-dihydrospiro[chromene-2,1'-cyclobutan]-4-yl]-2-(6-methoxy-2-naphthyl)propanamide, (2S)—N-[(4S)-6-Chloro-3,4-dihydrospiro[chromene-2,1'-cyclobutan]-4-yl]-2-(6-methoxy-2-naphthyl)propanamide,
N-(6-Chloro-3,4-dihydrospiro[chromene-2,1'-cyclobutan]-4-yl)-2-(1,2,3,4-tetrahydro naphthalen-1-yl)acetamide,
N-[(6-Chloro-3,4-dihydrospiro[chromene-2,1'-cyclobutan]-4-yl)]-2-(1,2,3,4-tetrahydro naphthalen-2-yl)acetamide,
2-(1,3-Benzodioxol-5-yl)-N-(6-chloro-3,4-dihydrospiro[chromene-2,1'-cyclobutan]-4-yl)acetamide,
N-(6-Fluoro-3,4-dihydrospiro[chromene-2,1'-cyclobutan]-4-yl)-2-(5-fluoro-3-methyl-1H-indol-2-yl)acetamide,
N-(6-Chloro-3,4-dihydrospiro[chromene-2,1'-cyclobutan]-4-yl)-2-(5-methoxy-2-methyl-1H-indol-3-yl)acetamide,
2-(1,2-Benzisoxazol-3-yl)-N-[(4R)-(6-chloro-3,4-dihydrospiro[chromene-2,1'-cyclobutan]-4-yl)acetamide,
2-(1,2-Benzisoxazol-3-yl)-N-[(4S)-(6-chloro-3,4-dihydrospiro[chromene-2,1'-cyclobutan]-4-yl)acetamide,
N-(6-Chloro-3,4-dihydrospiro[chromene-2,1'-cyclobutan]-4-yl)-3-(2-cyclopentyloxy phenyl)propanamide,
N-[(4R)-6-Chloro-3,4-dihydrospiro[chromene-2,1'-cyclobutan]-4-yl]-3-(3-cyclopentyloxy)phenylpropanamide,
N-[(4S)-6-Chloro-3,4-dihydrospiro[chromene-2,1'-cyclobutan]-4-yl]-3-(3-cyclopentyloxy)phenylpropanamide,
N-[(4R)-(8-Chloro-3,4-dihydrospiro[chromene-2,1'-cyclobutan]-4-yl)-3-(2-cyclopentyloxy)phenyl propanamide,
N-[(4S)-8-chloro-3,4-dihydrospiro[chromene-2,1'-cyclobutan-4-yl]-3-[2-(cyclopentyloxy)phenylproanamide,
7-Benzyloxy-N-(3,4-dihydrospiro[chromene-2,1'-cyclobutan]-4-yl)-3-(2-cyclopentyloxyphenyl)propanamide,
N-(6-Chloro-3,4-dihydrospiro[chromene-2,1'-cyclobutan]-4-yl)-3-{2-[(isopropylsulfonyl)amino]phenyl}propanamide,
N-(6-Chloro-3,4-dihydrospiro[chromene-2,1'-cyclobutan]-4-yl)-3-(2-pyridin-2-ylphenyl)propanamide,
N-(6,8-Dichloro-3,4-dihydrospiro[chromene-2,1'-cyclobutan]-4-yl)-3-(2-pyridin-3-ylphenyl)propanamide,
N-(3,4-Dihydrospiro[chromene-2,1'-cyclobutan]-4-yl)-3-(2-cyclopentyloxy-3-methoxy)phenylpropanamide,
N-(6-Chloro-3,4-dihydrospiro[chromene-2,1'-cyclobutan]-4-yl)-3-(2,3-dimethoxy)phenylpropanamide,
N-(6-Chloro-3,4-dihydrospiro[chromene-2,1'-cyclobutan]-4-yl)-3-(2-isopropoxy-3-methoxy)phenylpropanamide,
N-(6-Chloro-3,4-dihydrospiro[chromene-2,1'-cyclobutan]-4-yl)-3-(3-chloro-4-methoxy)phenylpropanamide,
N-(6-Chloro-3,4-dihydrospiro[chromene-2,1'-cyclobutan]-4-yl)-3-(2-cyclopropylmethoxy-3-methoxy)phenylpropanamide,
N-[(4R)-6-Chloro-3,4-dihydrospiro[chromene-2,1'-cyclobutan]-4-yl)]-3-(2-cyclopentyloxy-3-methoxy)phenylpropanamide,
N-[(4S)-6-Chloro-3,4-dihydrospiro[chromene-2,1'-cyclobutan]-4-yl)]-3-(2-cyclopentyloxy-3-methoxy)phenylpropanamide,
N-(6-Chloro-3,4-dihydrospiro[chromene-2,1'-cyclobutan]-4-yl)-3-(2-cyclopentyloxy-3-ethoxy)phenylpropanamide,
N-(7-Chloro-3,4-dihydrospiro[chromene-2,1'-cyclobutan]-4-yl)-3-(2-cyclopentyloxy-3-methoxy)phenylpropanamide,
N-(8-Chloro-3,4-dihydrospiro[chromene-2,1'-cyclobutan]-4-yl)-3-(2-ethoxy-3-methoxy)phenylpropanamide,
N-[(4S)-(8-Chloro-3,4-dihydrospiro[chromene-2,1'-cyclobutan]-4-yl)-3-(2-cyclopentyloxy-3-methoxy)phenylpropanamide,
N-(6-Chloro-7-methyl-3,4-dihydrospiro[chromene-2,1'-cyclobutan]-4-yl)-3-(2-cyclopentyloxy-3-methoxy)phenylpropanamide,
N-(5-Benzyloxy-3,4-dihydrospiro[chromene-2,1'-cyclobutan]-4-yl)-3-(2-cyclopentyloxy-3-methoxy)phenylpropanamide,
N-(5-Hydroxy-3,4-dihydrospiro[chromene-2,1'-cyclobutan]-4-yl)-3-(2-cyclopentyloxy-3-methoxy)phenylpropanamide,
N-(3,4-Dihydrospiro[chromene-2,1'-cyclobutan]-5-methoxy-4-yl)-3-(2-cyclopentyloxy-3-methoxy)phenylpropanamide,
(4R)-6-Chloro-N-(3,4-dihydrospiro[chromene-2,1'-cyclobutan]-4-yl)-3-(2-cyclopentyloxy-3-methyl)phenylpropanamide,
(4S)-6-Chloro-N-(3,4-dihydrospiro[chromene-2,1'-cyclobutan]-4-yl)-3-(2-cyclopentyloxy-3-methyl)phenylpropanamide,
N-6-Chloro-3,4-dihydrospiro[chromene-2,1'-cyclobutan]-4-yl-3-(2-hydroxy-3-methoxyphenyl)propanamide,
N-(6-Chloro-3,4-dihydrospiro[chromene-2,1'-cyclobutan]-4-yl)-3-(2-benzyloxy-3-methoxy)phenylpropanamide,
N-(6-Chloro-3,4-dihydrospiro[chromene-2,1'-cyclobutan]-4-yl)-3-{2-isopropoxy-3-[(methylsulfonyl)amino]phenyl}propanamide,
N-(8-Chloro-3,4-dihydrospiro[chromene-2,1'-cyclobutan]-4-yl)-3-{2-isopropoxy-3-[(methylsulfonyl)amino]phenyl}propanamide,
N-(6,8-Dichloro-3,4-dihydrospiro[chromene-2,1'-cyclobutan]-4-yl)-3-{[2-(dimethylamino)ethoxy-3-methoxy]phenyl}propanamide,
N-(6,8-Dichloro-3,4-dihydrospiro[chromene-2,1'-cyclobutan]-4-yl)-3-{2-propoxy-3-[(methylsulfonyl)amino]phenyl}propanamide,
N-(6,8-Dichloro-3,4-dihydrospiro[chromene-2,1'-cyclobutan]-4-yl)-3-{2-isopropoxy-5-[(methylsulfonyl)amino]phenyl}propanamide,
N-(6,8-Dichloro-3,4-dihydrospiro[chromene-2,1'-cyclobutan]-4-yl)-3-{2-butoxy-3-[(methylsulfonyl)amino]phenyl}propanamide,
N-(6,8-Dichloro-3,4-dihydrospiro[chromene-2,1'-cyclobutan]-4-yl)-3-{2-(cyclopropylmethoxy)-3-[(methylsulfonyl)amino]phenyl}propanamide,
N-(6,8-Dichloro-3,4-dihydrospiro[chromene-2,1'-cyclobutan]-4-yl)-3-{2-isopropoxy-3-[(methylsulfonyl)amino]phenyl}propanamide,
N-(6-Chloro-3,4-dihydrospiro[chromene-2,1'-cyclobutan]-4-yl)-3-(1-naphthyl)propanamide,
N-[4(S)-(6-Chloro-3,4-dihydrospiro[chromene-2,1'-cyclobutan]-4-yl)-3-(2-methoxy)-1-naphthylpropanamide,
N-[(4R)-6-Chloro-3,4-dihydrospiro[chromene-2,1'-cyclobutan]-4-yl)-3-(4-methoxy)-1-naphthylpropanamide, N-[(4S)-6-Chloro-3,4-dihydrospiro[chromene-2,1'-cyclobutan]-4-yl)-3-(4-methoxy)-1-naphthylpropanamide,
(4R)-6-Chloro-N-(3,4-dihydrospiro[chromene-2,1'-cyclobutan]-4-yl)-3-(4-difluoromethoxy-1-naphthyl)propanamide,
(4S)-6-Chloro-N-(3,4-dihydrospiro[chromene-2,1'-cyclobutan]-4-yl)-3-(4-difluoromethoxy-1-naphthyl)propanamide,
N-(6-Chloro-3,4-dihydrospiro[chromene-2,1'-cyclobutan]-4-yl)-3-(2-naphthyl)propanamide,
N-[4R-(6-Chloro-3,4-dihydrospiro[chromene-2,1'-cyclobutan]-4-yl)-3-(6-methoxy-2-naphthyl)propanamide,
N-[4S-(6-Chloro-3,4-dihydrospiro[chromene-2,1'-cyclobutan]-4-yl)-3-(6-methoxy-2-naphthyl)propanamide,
N-(6-Chloro-3,4-dihydrospiro[chromene-2,1'-cyclobutan]-4-yl)-3-(quinolin-2-yl)propanamide,
N-(6-Chloro-3,4-dihydrospiro[chromene-2,1'-cyclobutan]-4-yl)-3-(1H-indol-3-yl)propanamide,
N-(6-Chloro-3,4-dihydrospiro[chromene-2,1'-cyclobutan]-4-yl)-3-(2-methyl, 7-methoxy-1-benzofuran-4-yl) propanamide,
N-[(4R)-6-Chloro-3,4-dihydrospiro[chromene-2,1'-cyclobutan]-4-yl]-3-(7-methoxy-2-methyl-1-benzofuran-5-yl)propanamide,
N-[(4S)-6-Chloro-3,4-dihydrospiro[chromene-2,1'-cyclobutan]-4-yl]-3-(7-methoxy-2-methyl-1-benzofuran-5-yl)propanamide,
3-(1,4-Benzodioxin-6-yl)-N-(6-fluoro-3,4-dihydrospiro[chromene-2,1'-cyclobutan]-4-yl)propanamide,
3-(1,3-Benzodioxol-4-yl)-N-[6-chloro-3,4-dihydrospiro[chromene-2,1'-cyclobutan]-4-yl]propanamide,
3-(1,3-Benzodioxol-4-yl)-N-(8-chloro-3,4-dihydrospiro[chromene-2,1'-cyclobutan]-4-yl)propanamide,
3-(1,4-Benzodioxin-5-yl)-N-(6-chloro-3,4-dihydrospiro[chromene-2,1'-cyclobutan]-4-yl)propanamide,
N-(6-Chloro-3,4-dihydrospiro[chromene-2,1'-cyclopentan]-4-yl)-3-(2-cyclopentyloxy-3-methoxy)propanamide,
N-(6-Chloro-3,4-dihydrospiro[chromene-2,1'-cyclohexan]-4-yl)-3-(2-cyclopentyloxy-3-methoxy)phenylpropanamide,
N-(2,2-Dimethyl-3,4-dihydro-2H-chromen-4-yl)-3-(2-cyclopentyloxy-3-methoxy)phenylpropanamide,
N-(6-Chloro-3,4-dihydro-2H-thiochromen-4-yl)-3-(2-cyclopentyloxy-3-methoxyphenyl)propanamide,
N-(6-Chloro-3,4-dihydro-2H-thiochromen-4-yl)-3-(2-methoxy-1-naphthyl)propanamide,
N-(6-Chloro-3,4-dihydrospiro[chromene-2,1'-cyclobutan]-4-yl)-4-(2-cyclopentyloxyphenyl)butanamide,
N-(4R)-6-Chloro-3,4-dihydrospiro[chromene-2,1'-cyclobutan]-4-yl-4-(2-cyclopentyloxy-3-methoxyphenyl)butanamide,
(4R)—N-(8-Chloro-3,4-dihydrospiro[chromene-2,1'-cyclobutan]-4-yl)-4-(2-cyclopentyloxy-3-methoxyphenyl)butanamide,
(4S)—N-(8-Chloro-3,4-dihydrospiro[chromene-2,1'-cyclobutan]-4-yl)-4-(2-cyclopentyloxy-3-methoxyphenyl)butanamide,
N-(8-Chloro-6-fluoro-3,4-dihydrospiro[chromene-2,1'-cyclobutan]-4-yl)-4-(2-cyclopentyloxy-3-methoxyphenyl)butanamide,
N-(6,8-Dichloro-3,4-dihydrospiro[chromene-2,1'-cyclobutan]-4-yl)-4-(2-cyclopentyloxy-3-methoxyphenyl)butanamide,
N-(7-Benzyloxy-3,4-dihydrospiro[chromene-2,1'-cyclobutan]-4-yl)-4-(2-cyclopentyloxy-3-methoxyphenyl)butanamide,
N-(7-Hydroxy-3,4-dihydrospiro[chromene-2,1'-cyclobutan]-4-yl)-4-(2-cyclopentyloxy-3-methoxyphenyl)butanamide,
N-(6-Chloro-3,4-dihydrospiro[chromene-2,1'-cyclobutan]-4-yl)-4-oxo-4-(4-methoxy naphthyl)butanamide,
N-(6-Chloro-3,4-dihydrospiro[chromene-2,1'-cyclobutan]-4-yl)-4-hydroxy-4-(4-methoxynaphthyl)butanamide,
N-(6-Chloro-2,2-dimethyl-3,4-dihydro-2H-chromen-4-yl)-4-(2-cyclopentyloxy-3-methoxy)phenylbutanamide, and
N-(6-Chloro-3,4-dihydro-2H-thiochromen-4-yl)-4-(2-cyclopentyloxy-3-methoxyphenyl)butanamide or
a tautomer, regiomer, stereoisomer, enantiomer, diastereomer or pharmaceutically acceptable salt thereof.

41. A pharmaceutical composition comprising a compound according to claim 1, either as a free base or pharmaceutically acceptable salt form and a pharmaceutically acceptable excipient.

42. The pharmaceutical composition according to claim 41, wherein the pharmaceutically acceptable excipient is a carrier or diluent.

43. A process for the preparation compounds of formula (I):

$$\text{(I)}$$

wherein,
R$^1$ is selected from substituted or unsubstituted aryl, substituted or unsubstituted heteroaryl, substituted or unsubstituted heterocyclic group or substituted or unsubstituted cycloalkyl; in which aryl, heteroaryl and heterocyclic ring are mono, bi or tricyclic; and fully or partially aromatic;

wherein substituents on aryl, heteroaryl, heterocyclic ring and cycloalkyl are independently selected from the group consisting of halogen, hydroxy, nitro, cyano, substituted or unsubstituted amino, substituted or unsubstituted alkyl, linear or branched chain alkyl, linear or branched chain alkoxy, substituted or unsubstituted alkenyl, substituted or unsubstituted alkoxy, substituted or unsubstituted haloalkyl, fully or partially substituted haloalkyl, substituted or unsubstituted haloalkyloxy, fully or partially substituted haloalkyloxy, substituted or unsubstituted cycloalkyl, substituted or unsubstituted cycloalkoxy, substituted or unsubstituted cycloalkylalkyl, substituted or unsubstituted cycloalkylalkoxy, substituted or unsubstituted aryl, substituted or unsubstituted aryloxy, substituted or unsubstituted arylalkyl, substituted or unsubstituted arylalkoxy, substituted or unsubstituted heterocyclic group, substituted or unsubstituted heteroaryl, —S(O)$_p$R$^a$, —NHS(O)$_p$R$^a$, —O(CH$_2$)$_m$NR$^a$R$^b$, —C(O)—R$^a$ or —C(O)NR$^a$R$^b$;

R² is hydrogen;

each occurrence of $R^a$, $R^b$, $R^c$ and $R^d$ are independently selected from hydrogen, nitro, cyano, halogen, —$OR^e$, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, substituted or unsubstituted heteroaryl, substituted or unsubstituted heterocyclic group;

$R^e$ is selected from the group consisting of hydrogen, substituted or unsubstituted alkyl, substituted or unsubstituted alkenyl, substituted or unsubstituted cycloalkyl, substituted or unsubstituted aryl, substituted or unsubstituted heteroaryl, or substituted or unsubstituted heterocyclic group;

$R^3$ and $R^4$ are independently selected from hydrogen, halogen, substituted or unsubstituted amino, substituted or unsubstituted alkyl, linear or branched chain alkyl, linear or branched chain alkoxy, substituted or unsubstituted alkenyl, substituted or unsubstituted alkoxy, substituted or unsubstituted haloalkyl, fully or partially substituted haloalkyl, substituted or unsubstituted haloalkyloxy, fully or partially substituted haloalkyloxy, substituted or unsubstituted cycloalkyl, substituted or unsubstituted cycloalkoxy, substituted or unsubstituted cycloalkylalkyl, substituted or unsubstituted cycloalkylalkoxy, substituted or unsubstituted aryl;

'm' is an integer selected from 1 to 4;
'n' is an integer selected from 0 to 3;
'p' is an integer selected from 0 to 2;

with proviso that $R^b$ is not a group selected from —$OR^e$, —$NR^3R^4$ or $C(O)NR^3R^4$;

the process comprising the step(s) of:

compound of formula (I) (when R² is H) obtained by coupling of compound of formula (1) with compound of formula (2) in presence of suitable coupling agent combination and suitable solvents

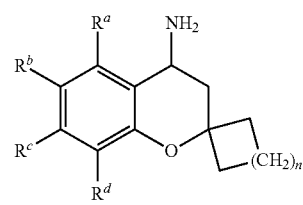

(1)

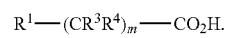

(2)

44. The process according to claim 43, wherein coupling agent combination selected from the group 1-hydroxybenzotriazole (HOBt), 1-(3-dimethylaminopropyl)-3-ethyl-carbodiimide hydrochloride (EDCI) and triethylamine.

45. The process according to claim 43, wherein suitable solvent is dichloromethane.

46. The process according to claim 43, wherein base is triethylamine.

47. A compound selected from:
N-[(4R)-8-Chloro-3,4-dihydrospiro[chromene-2,1'-cyclobutan]-4-yl)]-3-(2-cyclopentyloxy-3-methoxy)phenylpropanamide,
N-(6,8-Dichloro-3,4-dihydrospiro[chromene-2,1'-cyclobutan]-4-yl)-3-(2-cyclopentyloxy-3-methoxy)phenylpropanamide,
N-[4S-(6-Chloro-3,4-dihydrospiro[chromene-2,1'-cyclobutan]-4-yl)-3-(2-methoxy)-1-naphthylpropanamide,
N-(6-Chloro-3,4-dihydrospiro[chromene-2,1'-cyclobutan]-4-yl)-3-(dibenzo[b,d]furan-4-yl)propanamide,
N-(6-Chloro-3,4-dihydrospiro[chromene-2,1'-cyclobutan]-4-yl)-4-[2-(cyclopentyloxy)-3-methoxyphenyl]butanamide, and
N-{(4S)-6-Chloro-3,4-dihydrospiro[chromene-2,1'-cyclobutan]-4-yl}-4-[(2-(cyclopentyloxy)-3-methoxyphenyl]butanamide, or
a tautomer, regiomer, stereoisomer, enantiomer, diastereomer or pharmaceutically acceptable salt thereof.

* * * * *

UNITED STATES PATENT AND TRADEMARK OFFICE
CERTIFICATE OF CORRECTION

PATENT NO. : 8,487,121 B2
APPLICATION NO. : 12/808937
DATED : July 16, 2013
INVENTOR(S) : Lingam et al.

It is certified that error appears in the above-identified patent and that said Letters Patent is hereby corrected as shown below:

In the Specification

Column 1, Lines 4-9, should read:

--This application is a National Stage Application under 35 U.S.C. 371 of PCT International Application No. PCT/IN2008/000838, filed December 16, 2008, which claims the benefit of Indian Patent Application Nos. 2481/MUM/2007 filed on December 18, 2007, and 647/MUM/2008 filed on March 26, 2008, and U.S. Provisional Application Nos. 61/019,995, filed on January 09, 2008, and 61/043,931, filed on April 10, 2008, all of which are hereby incorporated by reference--.

Signed and Sealed this
First Day of July, 2014

Michelle K. Lee
*Deputy Director of the United States Patent and Trademark Office*